(12) United States Patent
Sun et al.

(10) Patent No.: US 9,249,132 B2
(45) Date of Patent: Feb. 2, 2016

(54) SUBSTITUTED BICYCLIC AROMATIC COMPOUNDS AS S-NITROSOGLUTATHIONE REDUCTASE INHIBITORS

(75) Inventors: Xicheng Sun, Broomfield, CO (US); Jian Qiu, Longmont, CO (US); Adam Stout, Denver, CO (US)

(73) Assignee: Nivalis Therapeutics, Inc., Boulder, CO (US)

( * ) Notice: Subject to any disclaimer, the term of this patent is extended or adjusted under 35 U.S.C. 154(b) by 17 days.

(21) Appl. No.: 13/991,973

(22) PCT Filed: Dec. 16, 2011

(86) PCT No.: PCT/US2011/065502
§ 371 (c)(1),
(2), (4) Date: Jun. 6, 2013

(87) PCT Pub. No.: WO2012/083171
PCT Pub. Date: Jun. 21, 2012

(65) Prior Publication Data
US 2013/0261122 A1 Oct. 3, 2013

Related U.S. Application Data

(60) Provisional application No. 61/423,799, filed on Dec. 16, 2010.

(51) Int. Cl.

| | | |
|---|---|---|
| *C07D 417/10* | (2006.01) |
| *C07D 215/20* | (2006.01) |
| *C07D 217/16* | (2006.01) |
| *C07D 239/34* | (2006.01) |
| *C07D 241/42* | (2006.01) |
| *C07D 253/10* | (2006.01) |
| *C07D 401/04* | (2006.01) |
| *C07D 403/10* | (2006.01) |
| *C07D 405/04* | (2006.01) |
| *C07D 409/04* | (2006.01) |
| *C07D 413/10* | (2006.01) |
| *C07C 65/105* | (2006.01) |
| *C07C 65/24* | (2006.01) |
| *C07D 213/79* | (2006.01) |
| *C07D 239/28* | (2006.01) |
| *C07D 241/24* | (2006.01) |
| *C07D 295/155* | (2006.01) |
| *C07D 215/06* | (2006.01) |
| *C07D 239/74* | (2006.01) |
| *C07D 409/14* | (2006.01) |
| *C07D 215/60* | (2006.01) |
| *C07D 239/26* | (2006.01) |
| *C07D 401/10* | (2006.01) |
| *C07D 217/04* | (2006.01) |

(52) U.S. Cl.
CPC ............ *C07D 417/10* (2013.01); *C07C 65/105* (2013.01); *C07C 65/24* (2013.01); *C07D 213/79* (2013.01); *C07D 215/06* (2013.01); *C07D 215/20* (2013.01); *C07D 215/60* (2013.01); *C07D 217/04* (2013.01); *C07D 217/16* (2013.01); *C07D 239/26* (2013.01); *C07D 239/28* (2013.01); *C07D 239/34* (2013.01); *C07D 239/74* (2013.01); *C07D 241/24* (2013.01); *C07D 241/42* (2013.01); *C07D 253/10* (2013.01); *C07D 295/155* (2013.01); *C07D 401/04* (2013.01); *C07D 401/10* (2013.01); *C07D 403/10* (2013.01); *C07D 405/04* (2013.01); *C07D 409/04* (2013.01); *C07D 409/14* (2013.01); *C07D 413/10* (2013.01)

(58) Field of Classification Search
CPC .. C07D 213/79; C07D 215/06; C07D 215/20; C07D 217/16; C07D 239/28; C07D 239/34; C07D 239/74; C07D 241/24; C07D 241/42; C07D 253/10; C07D 295/155; C07D 401/04; C07D 401/10; C07D 403/10; C07D 405/04; C07D 409/04; C07D 409/14; C07D 413/10; C07D 417/10; C07D 239/26
See application file for complete search history.

(56) References Cited

U.S. PATENT DOCUMENTS

| | | | |
|---|---|---|---|
| 5,124,473 | A | 6/1992 | Shroot et al. |
| 8,546,392 | B2 | 10/2013 | Hartmann et al. |
| 2002/0128205 | A1 | 9/2002 | Stamler et al. |
| 2005/0014697 | A1 | 1/2005 | Stamler et al. |
| 2005/0187166 | A1 | 8/2005 | Stamler et al. |
| 2005/0260126 | A1 | 11/2005 | Kudo et al. |
| 2007/0054903 | A1 | 3/2007 | Kim et al. |
| 2010/0204234 | A1 | 8/2010 | Hartmann et al. |
| 2010/0286174 | A1 | 11/2010 | Stamler et al. |
| 2011/0034507 | A1 | 2/2011 | Akwabi-Ameyaw et al. |

(Continued)

FOREIGN PATENT DOCUMENTS

| | | |
|---|---|---|
| DE | 19522167 | 12/1995 |
| DE | 19522195 | 12/1995 |

(Continued)

OTHER PUBLICATIONS

Machine translation of WO 2000031045 A1 obtained Mar. 31, 2015.*

(Continued)

*Primary Examiner* — Kendra D Carter
(74) *Attorney, Agent, or Firm* — Swanson & Bratschun, L.L.C.

(57) ABSTRACT

The present invention is directed to novel substituted bicyclic aromatic compounds useful as S-nitrosoglutathione reductase (GSNOR) inhibitors, pharmaceutical compositions comprising such compounds, and methods of making and using the same.

29 Claims, No Drawings

(56) References Cited

U.S. PATENT DOCUMENTS

| | | |
|---|---|---|
| 2013/0178499 A1 | 7/2013 | Sun et al. |
| 2013/0261122 A1 | 10/2013 | Sun et al. |
| 2013/0261123 A1 | 10/2013 | Sun et al. |

FOREIGN PATENT DOCUMENTS

| | | |
|---|---|---|
| DE | 4427199 | 2/1996 |
| EP | 210929 | 6/1992 |
| EP | 1571142 | 9/2005 |
| WO | WO 92-19583 | 11/1992 |
| WO | WO 95-01426 | 1/1995 |
| WO | WO 97-04039 | 2/1997 |
| WO | WO 0031045 A1 * | 6/2000 |
| WO | WO 2004-016673 | 2/2004 |
| WO | WO 2004-035522 | 4/2004 |
| WO | WO 2004-080170 | 9/2004 |
| WO | WO 2006-023821 | 3/2006 |
| WO | WO 2007-005668 | 1/2007 |
| WO | WO 2007/016525 A2 | 2/2007 |
| WO | WO 2007/035478 A2 | 3/2007 |
| WO | WO 2008-003702 | 1/2008 |
| WO | WO 2008-032105 | 3/2008 |
| WO | WO 2008-116920 | 10/2008 |
| WO | WO 2009-076665 | 6/2009 |
| WO | WO 2010/019903 | 2/2010 |
| WO | WO 2010/019905 A1 | 2/2010 |
| WO | WO 2010/019909 A1 | 2/2010 |
| WO | WO 2010-044405 | 4/2010 |
| WO | WO 2010-080414 | 7/2010 |
| WO | WO 2010-107476 | 9/2010 |
| WO | WO 2012-009227 | 1/2012 |

OTHER PUBLICATIONS

Frotscher et al. (2008) "Design, Synthesis, and Biological Evaluation of (Hydroxyphenyl)naphthalene and—quinoline Derivatives: Potent and Selective Nonsteroidal Inhibitors of 17β-Hydroxysteroid Dehydrogenase Type 1 (17β-HSD1) for the Treatment of Estrogen-Dependent Diseases ", J. Med. Che. 51(7):2158-2169.
Bateman et al. (Sep. 29, 2008) "Human carbonyl reductase is an S-nitrosoglutathione reductase" J Biol Chem, 283 p. 35756-35762.
de Belder et al. (May 1994) "Effects of S-nitroso-glutathione in the human forearm circulation; evidence for selective inhibition of platelet activation", Cardiovasc Res., 28(5):691-694.
de Jesus-Berrios et al. (Nov. 2003) "Enzymes that Counteract Nitrosative Stress Promot Fungal Virulence", Curr. Biol., 13:1963-1968.
Foster et al. (Apr. 2003) "S-nitrosylation in health and disease", Trends in Molecular Medicine, 9(4):160-168.
Gaston et al. (Dec. 1993) "Endogenous nitrogen oxides and bronchodilator S-nitrosolthiols in human airways", Proc. Natl. Acad. Sci. USA, 90:10957-10961.
Georgii et al. (2011) "Topical S-nitrosoglutathione-Releasing Hydrogel Improves Healing of Rat Ischaemic Wounds", J Tissue Eng Regen Med, 5:612-619.
Haq et al. (2007) "S-nitrosoglutathione Prevents Interphotoreceptor Retinoid-Binding Protein (IRBP$^{161-180}$)-Induced Experimental Autoimmune Uveitis" J Ocular Pharm and Therapeutics, 23(3):221-231.
International Preliminary Report on Patentability mailed in PCT/US2011/065502 on Jun. 27, 2013.
International Search Report and Written Opinion mailed in PCT/US2011/065502 on Apr. 20, 2012.
Jensen et al. (1998) "S-Nitrosoglutathione is a substrate for rat alcohol dehydrognease class III isoenzyme", Biochem J., 331:659-668.
Kaposzta et al. (2002) "S-Nitrosoglutathione Reduces Asymptomatic Embolization After Carotid Angioplasty", Circulation,106(24):3057-3062.
Lee (2008), "Acetaminophen-related Acute Liver Failure in the United States" Hepatology Research, 38 (Suppl. 1): S3-S8.
Lima et al. (2010), "S-Nitrosylation in Cardiovascular Signaling", Circ Res. 106(4):633-646.
Lipton et al. (Sep. 2001) "S-Nitrosothiols signal the ventilatory response to hypoxia", Nature, 413:171-174.
Liu et al. (Feb. 2004) "Essential Roles of S-Nitrosothiols in Vascular Homeostatsis and Endotoxic Shock", Cell, 116(4):617-628.
Liu et al. (Mar. 2001) "A metabolic enzyme for S-nitrosothiol conserved from bacterial to humans", Nature, 410:490-494.
Marchais-Oberwinkler (2008) "Substituted 6-Phenyl-2-naphthols. Potent and Selective Nonsteroidal Inhibitors of 17β-Hydroxysteroid Dehydrogenase Type 1 (17β-HSD1): Design, Synthesis, Biological Evaluation, and Pharmacokinetics", J Med Chem , 51(7), 4685-4698.
Prince et al. (2010) "The Nitric Oxide Donor S-Nitrosoglutathione Reduces Apoptotic Primary Liver Cell Loss in a Three-Dimensional Perfusion Bioreactor Culture Model Developed for Liver Support" Tissue Eng 16(3):861-866.
Que et al. (Jun. 2005) "Protection from Experimental Asthma by an Endogenous Bronchodilator", Science, 308(5728):1618-1621.
Sanghani et al. (2000) "Kinetic Mechanism of Human Glutathioone-Dependent Formaldehyde Dehydrogenase", Biochemistry,39:10720-10729.
Sanghani et al. (2002) "Human Glutathione-Dependent Formaldehyde Dehydrognease. Structures of Apo, Binary, and Inhibitory Ternary Complexes", Biochemistry,41:10778-10786.
Sanghani et al. (Jul. 11, 2009) Kinetic and Cellular Characterization of Novel Inhibitors of S-Nitrosogluthathione Reductase, J. Biol. Chem. 284:24354-24362.
Stamler et al. (Aug. 1992) "Nitric oxide circulates in mammalian plasma primarily as an S-nitrose adduct of serium albumin", Proc. Natl. Acad. Sci. USA, 89:7674-7677.
Uotila and Koivusalo (1989) Coenzymes and Cofactors vol. 3: Glutathione, part A., D. Dolphin, ed. pp. 517-551 (New York, John Wiley & Sons).
Zaman et al. (2001) "S-Nitrosoglutathione Increases Cystic Fibrosis Transmembrane Regulator Maturation", Biochem Biophys Res Commun., 284:65-70.
Nozaki, M. et al. (1995), "Souyaku Kagaku (Medicinal Chemistry)", Kagaku-Dojin Publishing Company, Inc., pp. 98 to 99.
Wermuth, C. G. (ed.), (Aug. 15, 1998) ,"Saishin Souyaku Kagaku (The Practice of Medicinal Chemistry)", Technomics, Inc., pp. 235 to 271, Chapter 13—Molecular Variations Based on Isosteric Replacements.
Office Action issued on Jul. 23, 2015 in corresponding Japanese application serial No. 2013-544827 (portion showing reievance of the references above).
Mewshaw et al. (2005) J. Med. Chem. 48:3953-3979, " Erβ Ligands. 3. Exploiting Two Binding Orientations of the 2-Phenylnaphthalene Scaffold to Achieve Erβ Selectivity".
EP Search Report issued Jun. 24, 2015 in EP 11849550.6.

* cited by examiner

SUBSTITUTED BICYCLIC AROMATIC COMPOUNDS AS S-NITROSOGLUTATHIONE REDUCTASE INHIBITORS

RELATED APPLICATIONS

This application is a 35 U.S.C. §371 national phase application of PCT/US2011/065502, filed Dec. 16, 2011 (WO 2012/083171). PCT/US2011/065502 claims priority to U.S. Provisional Application Serial No. 61/423,799, filed Dec. 16, 2010, which is incorporated herein by reference in its entirety.

FIELD OF THE INVENTION

The present invention is directed to novel substituted bicyclic aromatic compounds, pharmaceutical compositions comprising such compounds, and methods of making and using the same. These compounds are useful as inhibitors of S-nitrosoglutathione reductase (GSNOR).

BACKGROUND

The chemical compound nitric oxide is a gas with chemical formula NO. NO is one of the few gaseous signaling molecules known in biological systems, and plays an important role in controlling various biological events. For example, the endothelium uses NO to signal surrounding smooth muscle in the walls of arterioles to relax, resulting in vasodilation and increased blood flow to hypoxic tissues. NO is also involved in regulating smooth muscle proliferation, platelet function, and neurotransmission, and plays a role in host defense. Although NO is highly reactive and has a lifetime of a few seconds, it can both diffuse freely across membranes and bind to many molecular targets. These attributes make NO an ideal signaling molecule capable of controlling biological events between adjacent cells and within cells.

NO is a free radical gas, which makes it reactive and unstable, thus NO is short lived in vivo, having a half life of 3-5 seconds under physiologic conditions. In the presence of oxygen, NO can combine with thiols to generate a biologically important class of stable NO adducts called S-nitrosothiols (SNO's). This stable pool of NO has been postulated to act as a source of bioactive NO and as such appears to be critically important in health and disease, given the centrality of NO in cellular homeostasis (Stamler et al., Proc. Natl. Acad. Sci. USA, 89:7674-7677 (1992)). Protein SNO's play broad roles in the function of cardiovascular, respiratory, metabolic, gastrointestinal, immune, and central nervous system (Foster et al., Trends in Molecular Medicine, 9 (4):160-168, (2003)). One of the most studied SNO's in biological systems is S-nitrosoglutathione (GSNO) (Gaston et al., Proc. Natl. Acad. Sci. USA 90:10957-10961 (1993)), an emerging key regulator in NO signaling since it is an efficient trans-nitrosating agent and appears to maintain an equilibrium with other S-nitrosated proteins (Liu et al., Nature, 410:490-494 (2001)) within cells. Given this pivotal position in the NO—SNO continuum, GSNO provides a therapeutically promising target to consider when NO modulation is pharmacologically warranted.

In light of this understanding of GSNO as a key regulator of NO homeostasis and cellular SNO levels, studies have focused on examining endogenous production of GSNO and SNO proteins, which occurs downstream from the production of the NO radical by the nitric oxide synthetase (NOS) enzymes. More recently there has been an increasing understanding of enzymatic catabolism of GSNO which has an important role in governing available concentrations of GSNO and consequently available NO and SNO's.

Central to this understanding of GSNO catabolism, researchers have recently identified a highly conserved S-nitrosoglutathione reductase (GSNOR) (Jensen et al., Biochem J., 331:659-668 (1998); Liu et al., (2001)). GSNOR is also known as glutathione-dependent formaldehyde dehydrogenase (GSH-FDH), alcohol dehydrogenase 3 (ADH-3) (Uotila and Koivusalo, Coenzymes and Cofactors., D. Dolphin, ed. pp. 517-551 (New York, John Wiley & Sons, (1989)), and alcohol dehydrogenase 5 (ADH-5). Importantly GSNOR shows greater activity toward GSNO than other substrates (Jensen et al., (1998); Liu et al., (2001)) and appears to mediate important protein and peptide denitrosating activity in bacteria, plants, and animals. GSNOR appears to be the major GSNO-metabolizing enzyme in eukaryotes (Liu et al., (2001)). Thus, GSNO can accumulate in biological compartments where GSNOR activity is low or absent (e.g., airway lining fluid) (Gaston et al., (1993)).

Yeast deficient in GSNOR accumulate S-nitrosylated proteins which are not substrates of the enzyme, which is strongly suggestive that GSNO exists in equilibrium with SNO-proteins (Liu et al., (2001)). Precise enzymatic control over ambient levels of GSNO and thus SNO-proteins raises the possibility that GSNO/GSNOR may play roles across a host of physiological and pathological functions including protection against nitrosative stress wherein NO is produced in excess of physiologic needs. Indeed, GSNO specifically has been implicated in physiologic processes ranging from the drive to breathe (Lipton et al., Nature, 413:171-174 (2001)) to regulation of the cystic fibrosis transmembrane regulator (Zaman et al., Biochem Biophys Res Commun, 284: 65-70 (2001)), to regulation of vascular tone, thrombosis, and platelet function (de Belder et al., Cardiovasc Res.; 28(5): 691-4 (1994)), Z. Kaposzta, et al., Circulation; 106(24): 3057-3062, (2002)) as well as host defense (de Jesus-Berrios et al., Curr. Biol., 13:1963-1968 (2003)). Other studies have found that GSNOR protects yeast cells against nitrosative stress both in vitro (Liu et al., (2001)) and in vivo (de Jesus-Berrios et al., (2003)).

Collectively, data suggest GSNO as a primary physiological ligand for the enzyme S-nitrosoglutathione reductase (GSNOR), which catabolizes GSNO and consequently reduces available SNO's and NO in biological systems (Liu et al., (2001)), (Liu et al., Cell, 116(4), 617-628 (2004)), and (Que et al., Science, 308, (5728):1618-1621 (2005)). As such, this enzyme plays a central role in regulating local and systemic bioactive NO. Since perturbations in NO bioavailability has been linked to the pathogenesis of numerous disease states, including hypertension, atherosclerosis, thrombosis, asthma, gastrointestinal disorders, inflammation, and cancer, agents that regulate GSNOR activity are candidate therapeutic agents for treating diseases associated with NO imbalance.

Nitric oxide (NO), S-nitrosoglutathione (GSNO), and S-nitrosoglutathione reductase (GSNOR) regulate normal lung physiology and contribute to lung pathophysiology. Under normal conditions, NO and GSNO maintain normal lung physiology and function via their anti-inflammatory and bronchodilatory actions. Lowered levels of these mediators in pulmonary diseases such as asthma, chronic obstructive pulmonary disease (COPD) may occur via up-regulation of GSNOR enzyme activity. These lowered levels of NO and GSNO, and thus lowered anti-inflammatory capabilities, are key events that contribute to pulmonary diseases and which can potentially be reversed via GSNOR inhibition.

S-nitrosoglutathione (GSNO) has been shown to promote repair and/or regeneration of mammalian organs, such as the heart (Lima et al., 2010), blood vessels (Lima et al., 2010) skin (Georgii et al., 2010), eye or ocular structures (Haq et al., 2007) and liver (Prince et al., 2010). S-nitrosoglutathione reductase (GSNOR) is the major catabolic enzyme of GSNO. Inhibition of GSNOR is thought to increase endogenous GSNO.

Inflammatory bowel diseases (IBD's), including Crohn's and ulcerative colitis, are chronic inflammatory disorders of the gastrointestinal (GI) tract, in which NO, GSNO, and GSNOR can exert influences. Under normal conditions, NO and GSNO function to maintain normal intestinal physiology via anti-inflammatory actions and maintenance of the intestinal epithelial cell barrier. In IBD, reduced levels of GSNO and NO are evident and likely occur via up-regulation of GSNOR activity. The lowered levels of these mediators contribute to the pathophysiology of IBD via disruption of the epithelial barrier via dysregulation of proteins involved in maintaining epithelial tight junctions. This epithelial barrier dysfunction, with the ensuing entry of micro-organisms from the lumen, and the overall lowered anti-inflammatory capabilities in the presence of lowered NO and GSNO, are key events in IBD progression that can be potentially influenced by targeting GSNOR.

Cell death is the crucial event leading to clinical manifestation of hepatotoxicity from drugs, viruses and alcohol. Glutathione (GSH) is the most abundant redox molecule in cells and thus the most important determinant of cellular redox status. Thiols in proteins undergo a wide range of reversible redox modifications during times of exposure to reactive oxygen and reactive nitrogen species, which can affect protein activity. The maintenance of hepatic GSH is a dynamic process achieved by a balance between rates of GSH synthesis, GSH and GSSG efflux, GSH reactions with reactive oxygen species and reactive nitrogen species and utilization by GSH peroxidase. Both GSNO and GSNOR play roles in the regulation of protein redox status by GSH.

Acetaminophen overdoses are the leading cause of acute liver failure (ALF) in the United States, Great Britain and most of Europe. More than 100,000 calls to the U.S. Poison Control Centers, 56,000 emergency room visits, 2600 hospitalizations, nearly 500 deaths are attributed to acetaminophen in this country annually. Approximately, 60% recover without needing a liver transplant, 9% are transplanted and 30% of patients succumb to the illness. The acetaminophen-related death rate exceeds by at least three-fold the number of deaths due to all other idiosyncratic drug reactions combined (Lee, Hepatol Res 2008; 38 (Suppl. 1):S3-S8).

Liver transplantation has become the primary treatment for patients with fulminant hepatic failure and end—stage chronic liver disease, as well as certain metabolic liver diseases. Thus, the demand for transplantation now greatly exceeds the availability of donor organs. It has been estimated that more than 18,000 patients are currently registered with the United Network for Organ Sharing (UNOS) and that an additional 9000 patients are added to the liver transplant waiting list each year, yet less than 5000 cadaveric donors are available for transplantation.

Currently, there is a great need in the art for diagnostics, prophylaxis, ameliorations, and treatments for medical conditions relating to increased NO synthesis and/or increased NO bioactivity. In addition, there is a significant need for novel compounds, compositions, and methods for preventing, ameliorating, or reversing other NO-associated disorders. The present invention satisfies these needs.

SUMMARY

The present invention provides novel substituted bicyclic aromatic compounds. These compounds are useful as S-nitrosoglutathione reductase ("GSNOR") inhibitors. The invention encompasses pharmaceutically acceptable salts, stereoisomers, prodrugs, metabolites, and N-oxides of the described compounds. Also encompassed by the invention are pharmaceutical compositions comprising at least one compound of the invention and at least one pharmaceutically acceptable carrier.

The compositions of the present invention can be prepared in any suitable pharmaceutically acceptable dosage form.

The present invention provides a method for inhibiting GSNOR in a subject in need thereof. Such a method comprises administering a therapeutically effective amount of a pharmaceutical composition comprising at least one GSNOR inhibitor or a pharmaceutically acceptable salt, stereoisomer, prodrug, metabolite or N-oxide thereof, in combination with at least one pharmaceutically acceptable carrier. The GSNOR inhibitor can be a novel compound according to the invention, or it can be a known compound which previously was not known to be an inhibitor of GSNOR.

The present invention also provides a method of treating a disorder ameliorated by NO donor therapy in a subject in need thereof. Such a method comprises administering a therapeutically effective amount of a pharmaceutical composition comprising at least one GSNOR inhibitor or a pharmaceutically acceptable salt, stereoisomer, prodrug, metabolite, or N-oxide thereof, in combination with at least one pharmaceutically acceptable carrier. The GSNOR inhibitor can be a novel compound according to the invention, or it can be a known compound which previously was not known to be an inhibitor of GSNOR.

The present invention also provides a method of treating a cell proliferative disorder in a subject in need thereof. Such a method comprises administering a therapeutically effective amount of a pharmaceutical composition comprising at least one GSNOR inhibitor or a pharmaceutically acceptable salt, stereoisomer, prodrug, metabolite, or N-oxide thereof, in combination with at least one pharmaceutically acceptable carrier. The GSNOR inhibitor can be a novel compound according to the invention, or it can be a known compound which previously was not known to be an inhibitor of GSNOR.

The methods of the invention encompass administration with one or more secondary active agents. Such administration can be sequential or in a combination composition.

Although methods and materials similar or equivalent to those described herein can be used in the practice or testing of the present invention, suitable methods and materials are described below. All publicly available publications, patent applications, patents, and other references mentioned herein are incorporated by reference in their entirety. In the case of conflict, the present specification, including definitions, will control.

Both the foregoing summary and the following detailed description are exemplary and explanatory and are intended to provide further details of the compositions and methods as claimed. Other objects, advantages, and novel features will be readily apparent to those skilled in the art from the following detailed description.

DETAILED DESCRIPTION

A. Overview of the Invention

Until recently, S-nitrosoglutathione reductase (GSNOR) was known to oxidize the formaldehyde glutathione adduct, S-hydroxymethylglutathione. GSNOR has since been identified in a variety of bacteria, yeasts, plants, and animals and is well conserved. The proteins from *E. coli, S. cerevisiae* and mouse macrophages share over 60% amino acid sequence identity. GSNOR activity (i.e., decomposition of GSNO when NADH is present as a required cofactor) has been detected in *E. coli*, in mouse macrophages, in mouse endothelial cells, in mouse smooth muscle cells, in yeasts, and in human HeLa, epithelial, and monocyte cells. Human GSNOR nucleotide and amino acid sequence information can be obtained from the National Center for Biotechnology Information (NCBI) databases under Accession Nos. M29872, NM_000671. Mouse GSNOR nucleotide and amino acid sequence information can be obtained from NCBI databases under Accession Nos. NM_007410. In the nucleotide sequence, the start site and stop site are underlined. CDS designates coding sequence. SNP designates single nucleotide polymorphism. Other related GSNOR nucleotide and amino acid sequences, including those of other species, can be found in U.S. Patent Application 2005/0014697.

In accord with the present invention, GSNOR has been shown to function in vivo and in vitro to metabolize S-nitrosoglutathione (GSNO) and protein S-nitrosothiols (SNOs) to modulate NO bioactivity, by controlling the intracellular levels of low mass NO donor compounds and preventing protein nitrosylation from reaching toxic levels.

Based on this, it follows that inhibition of this enzyme potentiates bioactivity in diseases in which NO donor therapy is indicated, inhibits the proliferation of pathologically proliferating cells, and increases NO bioactivity in diseases where this is beneficial.

The present invention provides pharmaceutical agents that are potent inhibitors of GSNOR. In particular, provided are substituted bicyclic aromatic analogs having the structure depicted below (Formula 1), or a pharmaceutically acceptable salt, stereoisomer, prodrug, metabolite, or N-oxide thereof.

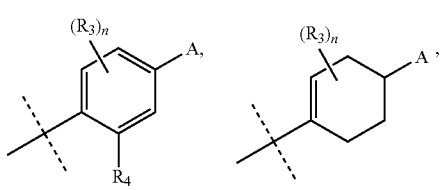

Formula 1

Wherein $R_1$ is selected from the group consisting of H, F, and Cl;

$R_{2a}$ and $R_{2b}$ are independently selected from the group consisting of H, F, Cl, Br, Me, $OCH_3$, and cyano;

$R_{2c}$ is selected from the group consisting of H, F, Cl, Br, Me, and $OCH_3$;

X is selected from the group consisting of

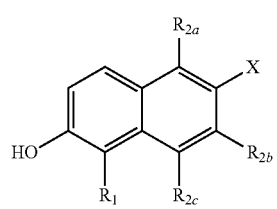

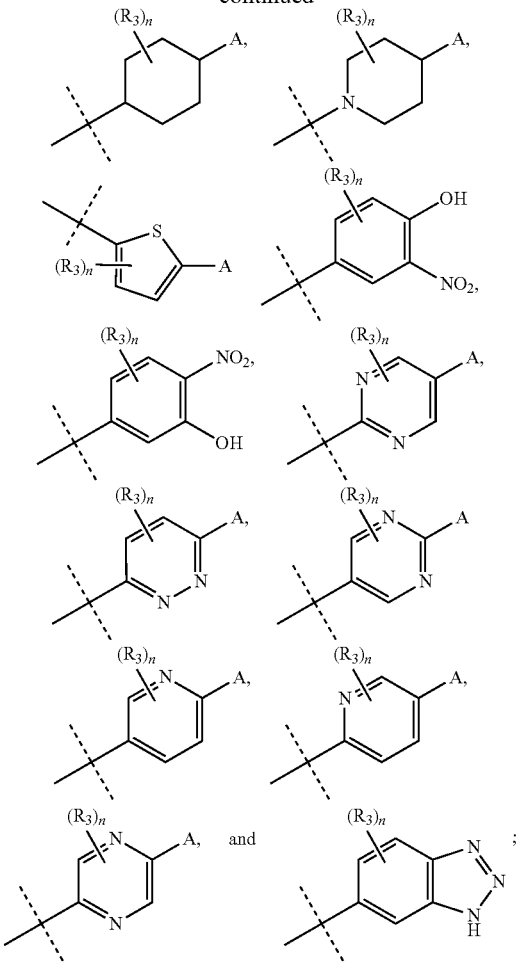

A is selected from the group consisting of

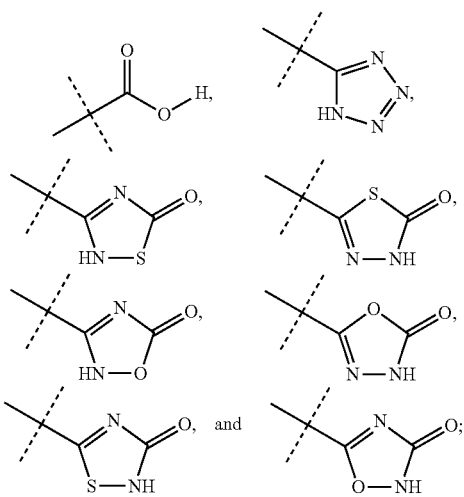

$R_3$ is selected from the group consisting of F, Cl, Br, $CH_3$, $CF_3$, $OCH_3$, cyano, $N(CH_3)_2$, and morpholino;

n is selected from the group consisting of 0, 1, and 2;

$R_4$ is selected from the group consisting of H, F, Cl, Br, $CH_3$, $CF_3$, $OCH_3$, cyano, $N(CH_3)_2$, and morpholino; and with the proviso that when X is

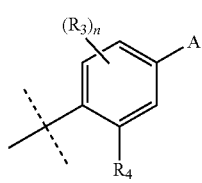

and A is COOH, then at least one of $R_1$, $R_{2a}$, $R_{2b}$, $R_{2c}$, and $R_4$ is not hydrogen, or n must be >0, and $R_3$ when meta to naphthalene, cannot be $CH_3$.

As used in this context, the term "analog" refers to a compound having similar chemical structure and function as compounds of Formula I that retains the substituted bicyclic aromatic ring system.

Some analogs of the invention can also exist in various isomeric forms, including configurational, geometric, and conformational isomers, as well as existing in various tautomeric forms, particularly those that differ in the point of attachment of a hydrogen atom. As used herein, the term "isomer" is intended to encompass all isomeric forms of a compound including tautomeric forms of the compound.

Illustrative compounds having asymmetric centers can exist in different enantiomeric and diastereomeric forms. A compound can exist in the form of an optical isomer or a diastereomer. Accordingly, the invention encompasses compounds in the forms of their optical isomers, diastereomers and mixtures thereof, including racemic mixtures.

It should be noted that if there is a discrepancy between a depicted structure and a name given to that structure, the depicted structure controls. In addition, if the stereochemistry of a structure or a portion of a structure is not indicated with, for example, bold, wedged, or dashed lines, the structure or portion of the structure is to be interpreted as encompassing all stereoisomers of the described compound.

B. S-Nitrosoglutathione Reductase Inhibitors
1. Inventive Compounds

In one of its aspects the present invention provides a compound having a structure shown in Formula 1, or a pharmaceutically acceptable salt, stereoisomer, prodrug, metabolite, or N-oxide thereof:

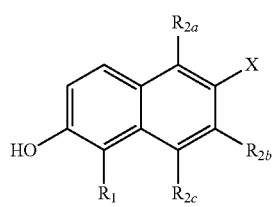

Formula 1

Wherein
$R_1$ is selected from the group consisting of H, F, and Cl;
$R_{2a}$ and $R_{2b}$ are independently selected from the group consisting of H, F, Cl, Br, Me, $OCH_3$, and cyano;
$R_{2c}$ is selected from the group consisting of H, F, Cl, Br, Me, and $OCH_3$;
X is selected from the group consisting of

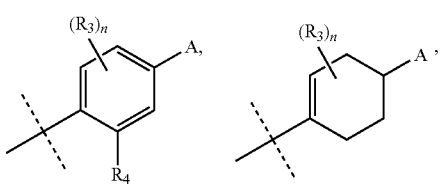

-continued

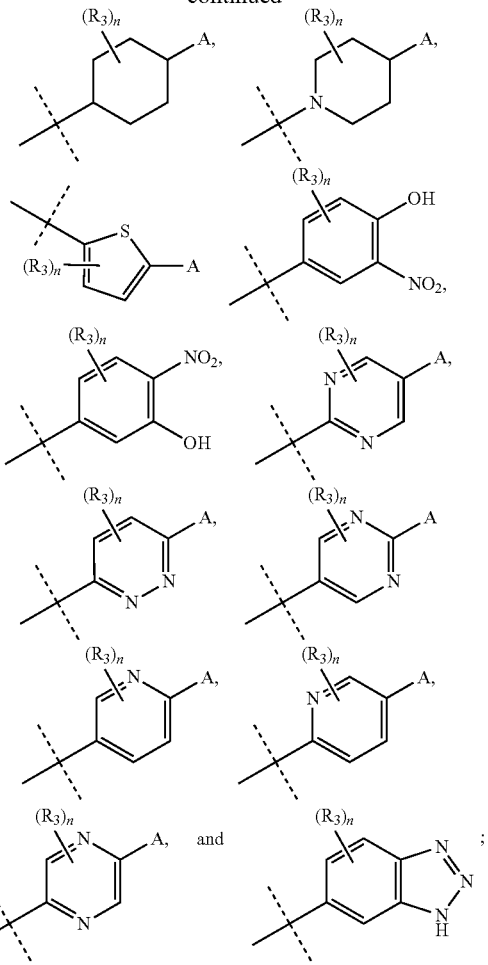

A is selected from the group consisting of

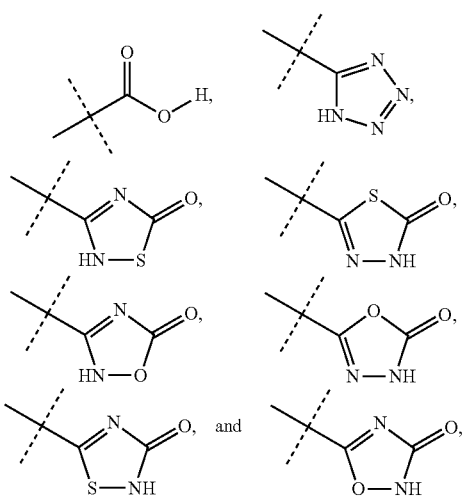

$R_3$ is selected from the group consisting of F, Cl, Br, $CH_3$, $CF_3$, $OCH_3$, cyano, $N(CH_3)_2$, and morpholino;
n is selected from the group consisting of 0, 1, and 2;
$R_4$ is selected from the group consisting of H, F, Cl, Br, $CH_3$, $CF_3$, $OCH_3$, cyano, $N(CH_3)_2$, and morpholino; and with the proviso that when X is

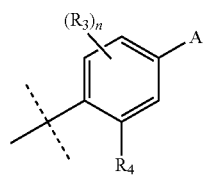

and A is COOH, then at least one of $R_1$, $R_{2a}$, $R_{2b}$, $R_{2c}$, $R_4$ is not hydrogen, or n must be >0, and $R_3$ when meta to naphthalene, cannot be $CH_3$.

In a further aspect of the invention, X is selected from the group consisting of

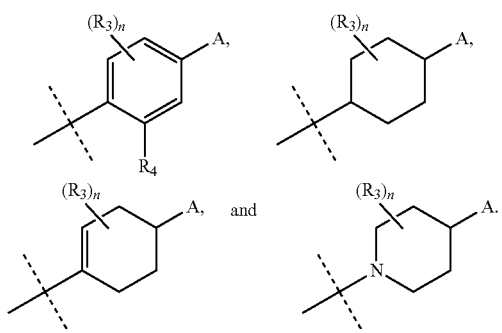

In a further aspect of the invention, X is

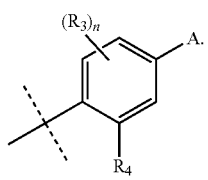

In a further aspect of the invention, $R_{2c}$ is hydrogen.
In a further aspect of the invention, $R_{2b}$ is hydrogen.
In a further aspect of the invention, the compound of Formula 1 has the structure shown in Formula 2:

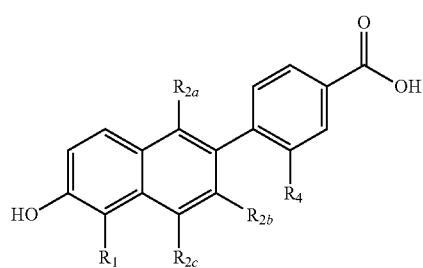

Formula 2

In a further aspect of the invention, $R_1$ of Formula 2 is selected from the group consisting of H and F;
In a further aspect of the invention, $R_{2a}$ of Formula 2 is selected from the group consisting of H, F, Cl, Br, and cyano;
In a further aspect of the invention, $R_{2b}$ of Formula 2 is selected from the group consisting of H, F, and Cl;

In a further aspect of the invention, $R_{2c}$ of Formula 2 is H;
In a further aspect of the invention, $R_4$ of Formula 2 is selected from the group consisting of H, F, Cl, and cyano.
In a further aspect of the invention, $R_1$ of Formula 2 is selected from the group consisting of F and Cl.
In a further aspect of the invention, $R_{2a}$ of Formula 2 is selected from the group consisting of F, Cl, Br, Me, $OCH_3$, and cyano.
In a further aspect of the invention, $R_{2b}$ of Formula 2 is selected from the group consisting of F, Cl, Br, Me, $OCH_3$, and cyano.
In a further aspect of the invention, $R_2$, of Formula 2 is selected from the group consisting of F, Cl, Br, Me, and $OCH_3$;
In a further aspect of the invention, $R_4$ of Formula 2 is selected from the group consisting of F, Cl, Br, $CH_3$, $CF_3$, $OCH_3$, cyano, $N(CH_3)_2$, and morpholino;
In a further aspect of the invention, the compound of Formula 1 has the structure shown in Formula 3

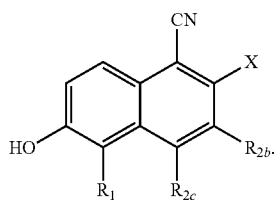

Formula 3

In a further aspect of the invention, X of Formula 3 is

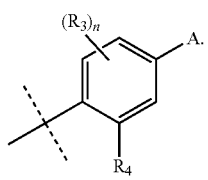

In a further aspect of the invention, A of Formula 3 is COOH.
In a further aspect of the invention, the compound of Formula 3 has the structure shown in Formula 4:

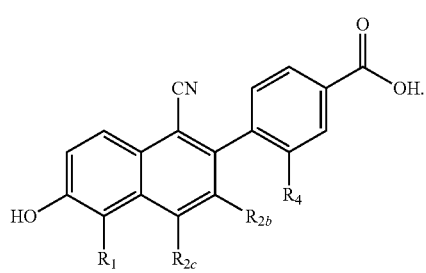

Formula 4

In a further aspect of the invention, $R_{2c}$ of Formula 4 is H.
In a further aspect of the invention, $R_{2b}$ of Formula 4 is H.
In a further aspect of the invention, $R_1$ of Formula 4 is selected from the group consisting of H and F.
In a further aspect of the invention, $R_{2b}$ of Formula 4 is selected from the group consisting of H, F, and Cl.

In a further aspect of the invention, $R_{2c}$ of Formula 4 is H;

In a further aspect of the invention, $R_4$ of Formula 4 is selected from the group consisting of H, F, Cl, and cyano.

In a further aspect of the invention, the compound of Formula 1 has the structure shown in Formula 5

Formula 5

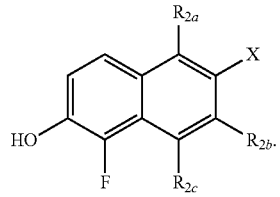

In a further aspect of the invention, X of Formula 5 is

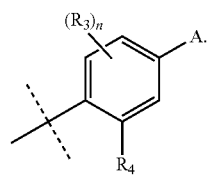

In a further aspect of the invention, A of Formula 5 is COOH.

In a further aspect of the invention, the compound of Formula 5 has the structure shown in Formula 6:

Formula 6

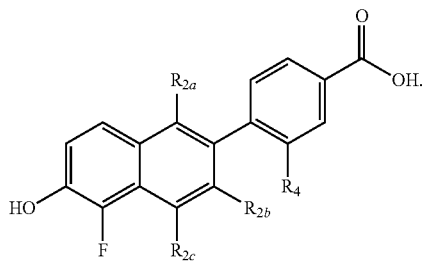

In a further aspect of the invention, $R_{2c}$ of Formula 6 is H.

In a further aspect of the invention, $R_{2b}$ of Formula 6 is H.

In a further aspect of the invention, $R_{2a}$ of Formula 6 is selected from the group consisting of H, F, Cl, Br, and cyano.

In a further aspect of the invention, $R_{2b}$ of Formula 6 is selected from the group consisting of H, F, and Cl.

In a further aspect of the invention, $R_{2c}$ of Formula 6 is H;

In a further aspect of the invention, $R_4$ of Formula 6 is selected from the group consisting of H, F, Cl, and cyano.

In one of its aspects the present invention provides a compound having a structure shown in Formula 7, or a pharmaceutically acceptable salt, stereoisomer, prodrug, metabolite, or N-oxide thereof:

Formula 7

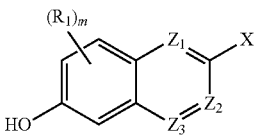

wherein $Z_1$ is selected from the group consisting of $CR_{2a}$ and N;
$Z_2$ is selected from the group consisting of $CR_{2b}$ and N;
$Z_3$ is selected from the group consisting of $CR_{2c}$ and N;
with the proviso that at least 1 of $Z_1$, $Z_2$, or $Z_3$ must be N;
m is selected from the group consisting of 0, 1, 2, or 3;
$R_1$ is independently selected from the group consisting of chloro, fluoro, and bromo;
$R_{2a}$, $R_{2b}$, and $R_{2c}$, are independently selected from the group consisting of hydrogen, halogen, $C_1$-$C_3$ alkyl, fluorinated $C_1$-$C_3$ alkyl, cyano, $C_1$-$C_3$ alkoxy, and $N(CH_3)_2$;
X is selected from the group consisting of

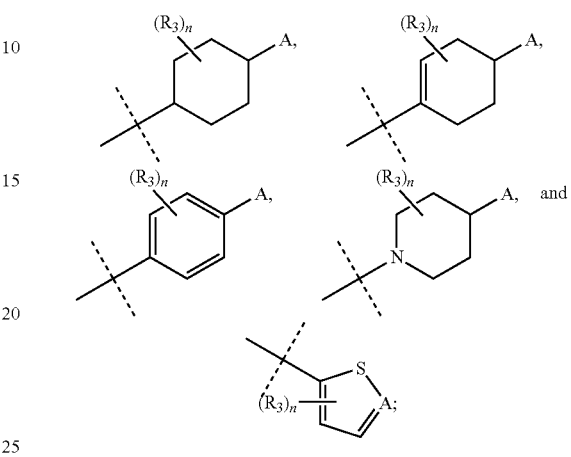

n is selected from 0, 1, and 2;
$R_3$ is independently selected from the group consisting of halogen, $C_1$-$C_3$ alkyl, fluorinated $C_1$-$C_3$ alkyl, cyano, $C_1$-$C_3$ alkoxy, and $NR_4R_{4'}$ where $R_4$ and $R_{4'}$ are independently selected from the group consisting of $C_1$-$C_3$ alkyl, or $R_4$ when taken together with $R_{4'}$ form a ring with 3 to 6 members;
A is selected from the group consisting of

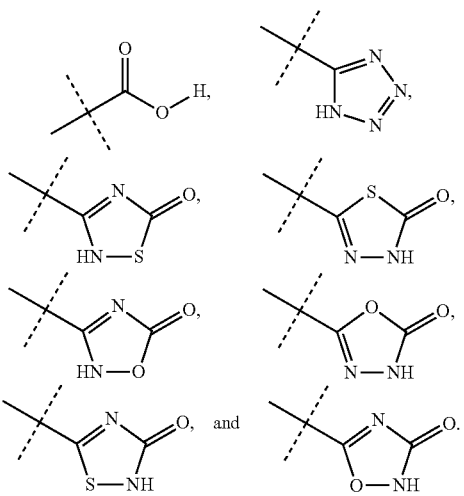

One aspect of the invention includes compounds of Formula 7 wherein $Z_1$, $Z_2$, and $Z_3$ are all $CR_{2a\text{-}c}$.

One aspect of the invention includes compounds of Formula 7 wherein $Z_1$, $Z_2$, and $Z_3$ are all $CR_{2a\text{-}c}$ and wherein X has an expanded definition to include nitrogen containing 6-membered aromatic rings.

In a further aspect of the invention, compounds of Formula 1 include but are not limited to:
3-chloro-4-(6-hydroxynaphthalen-2-yl)benzoic acid;
3-fluoro-4-(6-hydroxynaphthalen-2-yl)benzoic acid;
4-(6-hydroxynaphthalen-2-yl)-3-methoxybenzoic acid;

3-(dimethylamino)-4-(6-hydroxynaphthalen-2-yl)benzoic acid;
3-cyano-4-(6-hydroxynaphthalen-2-yl)benzoic acid;
4-(6-hydroxynaphthalen-2-yl)-3-morpholinobenzoic acid;
4-(1-bromo-6-hydroxynaphthalen-2-yl)benzoic acid;
4-(6-hydroxy-1-methylnaphthalen-2-yl)benzoic acid;
4-(1-cyano-6-hydroxynaphthalen-2-yl)benzoic acid;
4-(6-hydroxy-3-methoxynaphthalen-2-yl)benzoic acid;
4-(1-chloro-6-hydroxynaphthalen-2-yl)benzoic acid;
6-(4-(1H-tetrazol-5-yl)phenyl)naphthalen-2-ol;
5-(6-hydroxynaphthalen-2-yl)picolinic acid;
6-(6-hydroxynaphthalen-2-yl)nicotinic acid;
5-(6-hydroxynaphthalen-2-yl)pyrazine-2-carboxylic acid;
2-(6-hydroxynaphthalen-2-yl)pyrimidine-5-carboxylic acid;
6-(6-hydroxynaphthalen-2-yl)pyridazine-3-carboxylic acid;
5-(6-hydroxynaphthalen-2-yl)pyrimidine-2-carboxylic acid;
6-(1H-benzo[d][1,2,3]triazol-6-yl)naphthalen-2-ol;
4-(6-hydroxynaphthalen-2-yl)-3-(trifluoromethyl)benzoic acid;
3-chloro-4-(3-fluoro-6-hydroxynaphthalen-2-yl)benzoic acid;
4-(3-chloro-6-hydroxynaphthalen-2-yl)benzoic acid;
4-(3-fluoro-6-hydroxynaphthalen-2-yl)benzoic acid;
4-(6-hydroxy-1-methoxynaphthalen-2-yl)benzoic acid;
4-(1-fluoro-6-hydroxynaphthalen-2-yl)benzoic acid;
4-(6-hydroxy-3-methylnaphthalen-2-yl)benzoic acid;
4-(1-cyano-5-fluoro-6-hydroxynaphthalen-2-yl)benzoic acid;
4-(1-cyano-6-hydroxynaphthalen-2-yl)-3-fluorobenzoic acid;
3-chloro-4-(5-fluoro-6-hydroxynaphthalen-2-yl)benzoic acid;
4-(5-fluoro-6-hydroxynaphthalen-2-yl)benzoic acid;
3-fluoro-4-(5-fluoro-6-hydroxynaphthalen-2-yl)benzoic acid; and
4-(5-fluoro-6-hydroxynaphthalen-2-yl)-3-methylbenzoic acid.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such substituent. Combinations of substituents and/or variables are permissible, but only if such combinations result in stable compounds.

The compounds described herein may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic, and geometric isomeric forms of a structure are intended, unless the specific stereochemistry or isomeric form is specifically indicated. All tautomers of shown or described compounds are also considered to be part of the present invention.

It is to be understood that isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate.

2. Representative Compounds

Examples 1-32 list representative substituted bicyclic aromatic compounds analogs of Formula I. The synthetic methods that can be used to prepare each compound are detailed in Examples 1-32. Supporting mass spectrometry data and/or proton NMR data for each compound is also included in Examples 1-32. GSNOR inhibitor activity was determined by the assay described in Example 34 and $IC_{50}$ values were obtained. GSNOR inhibitor compounds in Examples 1-33 had an $IC_{50}$ of about <5 µM. GSNOR inhibitor compounds in Examples 1-3, 5, 6, 12, 15, 17, 18, 20-33 had an $IC_{50}$ of about <0.1 µM. GSNOR inhibitor compounds in Examples 1, 2, 6, 12, 15, 17, 21-23, 25, 27-32 had an $IC_{50}$ of about <0.05 µM.

C. Definitions

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

The term "acyl" includes compounds and moieties that contain the acetyl radical ($CH_3CO$—) or a carbonyl group to which a straight or branched chain lower alkyl residue is attached.

The term "alkyl" as used herein refers to a straight or branched chain, saturated hydrocarbon having the indicated number of carbon atoms. For example, ($C_1$-$C_6$) alkyl is meant to include, but is not limited to methyl, ethyl, propyl, isopropyl, butyl, sec-butyl, tert-butyl, pentyl, isopentyl, neopentyl, hexyl, isohexyl, and neohexyl. An alkyl group can be unsubstituted or optionally substituted with one or more substituents as described herein.

The term "alkenyl" as used herein refers to a straight or branched chain unsaturated hydrocarbon having the indicated number of carbon atoms and at least one double bond. Examples of a ($C_2$-$C_8$) alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, isoheptene, 1-octene, 2-octene, 3-octene, 4-octene, and isooctene. An alkenyl group can be unsubstituted or optionally substituted with one or more substituents as described herein.

The term "alkynyl" as used herein refers to a straight or branched chain unsaturated hydrocarbon having the indicated number of carbon atoms and at least one triple bond. Examples of a ($C_2$-$C_8$) alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne, and 4-octyne. An alkynyl group can be unsubstituted or optionally substituted with one or more substituents as described herein.

The term "alkoxy" as used herein refers to an —O-alkyl group having the indicated number of carbon atoms. For example, a ($C_1$-$C_6$) alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl.

The term "aminoalkyl" as used herein, refers to an alkyl group (typically one to six carbon atoms) wherein one or more of the $C_1$-$C_6$ alkyl group's hydrogen atoms is replaced with an amine of formula —$N(R^c)_2$, wherein each occurrence of $R^c$ is independently —H or ($C_1$-$C_6$) alkyl. Examples of aminoalkyl groups include, but are not limited to, —$CH_2NH_2$, —$CH_2CH_2NH_2$, —$CH_2CH_2CH_2NH_2$, —$CH_2CH_2CH_2CH_2NH_2$, —$CH_2CH_2CH_2CH_2CH_2NH_2$, —$CH_2CH_2CH_2CH_2CH_2CH_2NH_2$, —$CH_2CH_2CH_2N(CH_3)_2$, t-butylaminomethyl, isopropylaminomethyl, and the like.

The term "aryl" as used herein refers to a 5- to 14-membered monocyclic, bicyclic, or tricyclic aromatic ring system. Examples of an aryl group include phenyl and naphthyl. An aryl group can be unsubstituted or optionally substituted with one or more substituents as described herein below. Examples of aryl groups include phenyl or aryl heterocycles such as, pyrrole, furan, thiophene, thiazole, isothiazole, imidazole, triazole, tetrazole, pyrazole, oxazole, isoxazole, pyridine, pyrazine, pyridazine, and pyrimidine, and the like.

As used herein, the term "bioactivity" indicates an effect on one or more cellular or extracellular process (e.g., via binding, signaling, etc.) which can impact physiological or pathophysiological processes.

The term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "carboxy" or "carboxyl" means a —COOH group or carboxylic acid.

"Acidic moiety" as used herein is defined as a carboxylic acid or a carboxylic acid bioisostere. Bioisosteres are substituents or groups with similar physical or chemical properties which produce broadly similar biological properties to a chemical compound. For a review of bioisosteres, see *J. Med. Chem.*, 2011, 54, 2529-2591. Examples of "acidic moiety" include but are not limited to

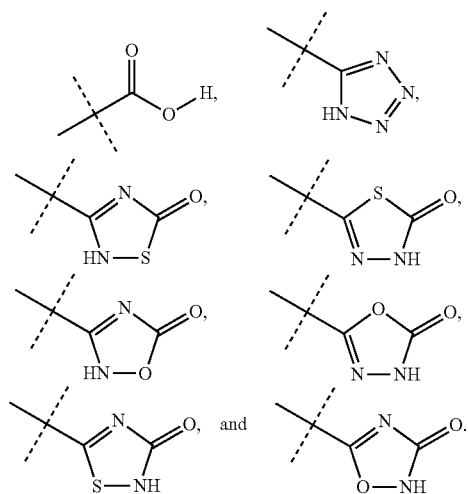

"Pharmacophore" is defined as "a set of structural features in a molecule that is recognized at a receptor site and is responsible for that molecule's biological activity" (Gund, *Prog. Mol. Subcell. Biol.*, 5: pp 117-143 (1977)).

The term "$C_m$-$C_n$" means "m" number of carbon atoms to "n" number of carbon atoms. For example, the term "$C_1$-$C_6$" means one to six carbon atoms ($C_1$, $C_2$, $C_3$, $C_4$, $C_5$, or $C_6$). The term "$C_2$-$C_6$" includes two to six carbon atoms ($C_2$, $C_3$, $C_4$, $C_5$, or $C_6$). The term "$C_3$-$C_6$" includes three to six carbon atoms ($C_3$, $C_4$, $C_5$, or $C_6$).

The term "cycloalkyl" as used herein refers to a 3- to 14-membered saturated or unsaturated non-aromatic monocyclic, bicyclic, or tricyclic hydrocarbon ring system. Included in this class are cycloalkyl groups which are fused to a benzene ring. Representative cycloalkyl groups include, but are not limited to, cyclopropyl, cyclobutyl, cyclobutenyl, cyclopentyl, cyclopentenyl, cyclopentadienyl, cyclohexyl, cyclohexenyl, 1,3-cyclohexadienyl, cycloheptyl, cycloheptenyl, 1,3-cycloheptadienyl, 1,4-cycloheptadienyl, -1,3,5-cycloheptatrienyl, cyclooctyl, cyclooctenyl, 1,3-cyclooctadienyl, 1,4-cyclooctadienyl, -1,3,5-cyclooctatrienyl, decahydronaphthalene, octahydronaphthalene, hexahydronaphthalene, octahydroindene, hexahydroindene, tetrahydroinden, decahydrobenzocycloheptene, octahydrobenzocycloheptene, hexahydrobenzocycloheptene, tetrahydrobenzocycloheptene, dodecahydroheptalene, decahydroheptalene, octahydroheptalene, hexahydroheptalene, tetrahydroheptalene, (1s,3s)-bicyclo[1.1.0]butane, bicyclo[1.1.1]pentane, bicyclo[2.1.1]hexane, Bicyclo[2.2.1]heptane, bicyclo[2.2.2]octane, bicyclo[3.1.1]heptane, bicyclo[3.2.1]octane, bicyclo[3.3.1]nonane, bicyclo[3.3.2]decane, bicyclo[3.3.]undecane, bicyclo[4.2.2]decane, and bicyclo[4.3.1]decane. A cycloalkyl group can be unsubstituted or optionally substituted with one or more substituents as described herein below.

The term "halogen" includes fluorine, bromine, chlorine, iodine, etc.

The term "haloalkyl," as used herein, refers to a $C_1$-$C_6$ alkyl group wherein from one or more of the $C_1$-$C_6$ alkyl group's hydrogen atom is replaced with a halogen atom, which can be the same or different. Examples of haloalkyl groups include, but are not limited to, trifluoromethyl, 2,2,2-trifluoroethyl, 4-chlorobutyl, 3-bromopropyl, pentachloroethyl, and 1,1,1-trifluoro-2-bromo-2-chloroethyl.

The term "heteroalkyl," by itself or in combination with another term, means, unless otherwise stated, a stable straight or branched chain alkyl, or combinations thereof, consisting of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N, and S can be placed at any position of the heteroalkyl group. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, and —$CH_2$—CH=N—$OCH_3$. Up to two heteroatoms can be consecutive, for example, —$CH_2$—NH—$OCH_3$. When a prefix such as ($C_2$-$C_8$) is used to refer to a heteroalkyl group, the number of carbons (2 to 8, in this example) is meant to include the heteroatoms as well. For example, a $C_2$-heteroalkyl group is meant to include, for example, —$CH_2OH$ (one carbon atom and one heteroatom replacing a carbon atom) and —$CH_2SH$.

To further illustrate the definition of a heteroalkyl group, where the heteroatom is oxygen, a heteroalkyl group can be an oxyalkyl group. For instance, ($C_2$-$C_5$) oxyalkyl is meant to include, for example —$CH_2$—O—$CH_3$ (a $C_3$-oxyalkyl group with two carbon atoms and one oxygen replacing a carbon atom), —$CH_2CH_2CH_2CH_2OH$, —$OCH_2CH_2OCH_2CH_2OH$, —$OCH_2CH(OH)CH_2OH$, and the like.

The term "heteroaryl" as used herein refers to an aromatic heterocycle ring of 5 to 14 members and having at least one heteroatom selected from nitrogen, oxygen, and sulfur, and containing at least 1 carbon atom, including monocyclic, bicyclic, and tricyclic ring systems. Representative heteroaryls are triazolyl, tetrazolyl, oxadiazolyl, pyridyl, furyl, benzofuranyl, thienyl, benzothienyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, azepinyl, oxepinyl, quinoxalinyl and oxazolyl. A heteroaryl group can be unsubstituted or optionally substituted with one or more substituents as described herein below.

As used herein, the term "heteroatom" is meant to include oxygen (O), nitrogen (N), and sulfur (S).

As used herein, the term "heterocycle" refers to 3- to 14-membered ring systems which are either saturated, unsaturated, or aromatic, and which contains from 1 to 4 heteroatoms independently selected from nitrogen, oxygen, and sulfur, and wherein the nitrogen and sulfur heteroatoms can be optionally oxidized, and the nitrogen heteroatom can be optionally quaternized, including monocyclic, bicyclic, and tricyclic ring systems. The bicyclic and tricyclic ring systems may encompass a heterocycle or heteroaryl fused to a benzene ring. The heterocycle can be attached via any heteroatom or carbon atom, where chemically acceptable. Heterocycles include heteroaryls as defined above. Representative examples of heterocycles include, but are not limited to, aziridinyl, oxiranyl, thiiranyl, triazolyl, tetrazolyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, dioxanyl, triazinyl, tetrazinyl, imidazolyl, tetrazolyl, pyrrolidinyl, isoxazolyl, furanyl, furazanyl, pyridinyl, oxazolyl, benzoxazolyl, benzisoxazolyl, thiazolyl, benzthiazolyl, thienyl, pyrazolyl, triazolyl, pyrimidinyl, benzimidazolyl, isoindolyl, indazolyl, benzodiazolyl, benzotriazolyl, benzoxazolyl, benzisoxazolyl, purinyl, indolyl, isoquinolinyl, quinolinyl, and quinazolinyl. A heterocycle group can be unsubstituted or optionally substituted with one or more substituents as described herein below.

The term "heterocycloalkyl," by itself or in combination with other terms, represents, unless otherwise stated, cyclic versions of "heteroalkyl." Additionally, a heteroatom can occupy the position at which the heterocycle is attached to the remainder of the molecule. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "hydroxyalkyl," as used herein, refers to an alkyl group having the indicated number of carbon atoms wherein one or more of the hydrogen atoms in the alkyl group is replaced with an —OH group. Examples of hydroxyalkyl groups include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, —CH$_2$CH$_2$CH$_2$CH$_2$CH$_2$CH$_2$OH, and branched versions thereof.

The term "hydroxy" or "hydroxyl" includes groups with an —OH or —O$^-$.

As used herein, N-oxide, or amine oxide, refers to a compound derived from a tertiary amine by the attachment of one oxygen atom to the nitrogen atom, $R_3N^+$—$O^-$. By extension the term includes the analogous derivatives of primary and secondary amines.

As used herein and unless otherwise indicated, the term "stereoisomer" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. In some embodiments, a stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

As used herein, "protein" is used synonymously with "peptide," "polypeptide," or "peptide fragment". A "purified" polypeptide, protein, peptide, or peptide fragment is substantially free of cellular material or other contaminating proteins from the cell, tissue, or cell-free source from which the amino acid sequence is obtained, or substantially free from chemical precursors or other chemicals when chemically synthesized.

As used herein, "modulate" is meant to refer to an increase or decrease in the levels of a peptide or a polypeptide, or to increase or decrease the stability or activity of a peptide or a polypeptide. The term "inhibit" is meant to refer to a decrease in the levels of a peptide or a polypeptide or to a decrease in the stability or activity of a peptide or a polypeptide. In preferred embodiments, the peptide which is modulated or inhibited is S-nitrosoglutathione (GSNO) or protein S-nitrosothiols (SNOs).

As used here, the terms "nitric oxide" and "NO" encompass uncharged nitric oxide and charged nitric oxide species, particularly including nitrosonium ion (NO$^+$) and nitroxyl ion (NO$^-$). The reactive form of nitric oxide can be provided by gaseous nitric oxide. Compounds having the structure X—NO$_y$, wherein X is a nitric oxide releasing, delivering, or transferring moiety, including any and all such compounds which provide nitric oxide to its intended site of action in a form active for their intended purpose, and Y is 1 or 2.

Repair" means recovering of structural integrity and normal physiologic function. By way of example, the oral and upper airway respiratory epithelium can repair damage done by thermal injury or viral infection.

"Regeneration" means the ability of an organ to enter nonmalignant cellular, vascular and stromal growth to restore functional organ tissue. By way of example, wound healing involves regeneration of tissue and organs (e.g. skin, gastric and intestinal mucosa), as does bone following fracture, and the liver following partial surgical removal and exposure to infectious or toxic insult.

As utilized herein, the term "pharmaceutically acceptable" means approved by a regulatory agency of a federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to such sterile liquids as water and oils.

A "pharmaceutically acceptable salt" or "salt" of a compound of the invention is a product of the disclosed compound that contains an ionic bond, and is typically produced by reacting the disclosed compound with either an acid or a base, suitable for administering to a subject. A pharmaceutically acceptable salt can include, but is not limited to, acid addition salts including hydrochlorides, hydrobromides, phosphates, sulphates, hydrogen sulphates, alkylsulphonates, arylsulphonates, arylalkylsulfonates, acetates, benzoates, citrates, maleates, fumarates, succinates, lactates, and tartrates; alkali metal cations such as Li, Na, and K, alkali earth metal salts such as Mg or Ca, or organic amine salts.

A "pharmaceutical composition" is a formulation comprising the disclosed compounds in a form suitable for administration to a subject. A pharmaceutical composition of the invention is preferably formulated to be compatible with its intended route of administration. Examples of routes of administration include, but are not limited to, oral and parenteral, e.g., intravenous, intradermal, subcutaneous, inhalation, topical, transdermal, transmucosal, and rectal administration.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Ring double bonds, as used herein, are double bonds that are formed between two adjacent ring atoms (e.g., C=C, C=N, or N=N).

Substituents for the groups referred to as alkyl, heteroalkyl, alkylene, alkenyl, alkynyl, cycloalkyl, heterocycloalkyl, cycloalkenyl, and heterocycloalkenyl can be selected from a variety of groups including —$OR^d$, =O, =$NR^{d\prime}$, =N—$OR^{d\prime}$, —$NR^{d\prime}R^{d\prime\prime\prime}$, —$SR^{d\prime}$, -halo, —$SiR^{d\prime}R^{d\prime\prime}R^{d\prime\prime\prime}$, —OC(O)$R^{d\prime}$, —C(O)$R^{d\prime}$, —$CO_2R^{d\prime}$, —CONR$^{d\prime}R^{d\prime\prime}$, —OC(O)NR$^{d\prime}R^{d\prime\prime}$, —$NR^{d\prime\prime}$C(O)$R^{d\prime}$, —$NR^{d\prime\prime\prime}$C(O)NR$^{d\prime}R^{d\prime\prime}$, —$NR^{d\prime\prime\prime}SO_2NR^{d\prime}R^{d\prime\prime}$, —$NR^{d\prime\prime}CO_2R^{d\prime}$, —NHC(NH$_2$)=NH, —$NR^{a\prime}$C(NH$_2$)=NH, —NHC(NH$_2$)=$NR^{d\prime}$, —S(O)$R^{d\prime}$, —$SO_2R^{d\prime}$, —$SO_2NR^{d\prime}R^{d\prime\prime}$, —$NR^{d\prime\prime}SO_2R^{d\prime}$, —CN, and —$NO_2$, in a number ranging from zero to three, with those groups having zero, one or two substituents being exemplary.

$R^{d\prime}$, $R^{d\prime\prime}$, and $R^{d\prime\prime\prime}$ each independently refer to hydrogen, unsubstituted ($C_1$-$C_8$)alkyl, unsubstituted hetero($C_1$-$C_8$) alkyl, unsubstituted aryl, and aryl substituted with one to three substituents selected from -halo, unsubstituted alkyl, unsubstituted alkoxy, unsubstituted thioalkoxy, and unsubstituted aryl ($C_1$-$C_4$)alkyl. When $R^{d\prime}$ and $R^{d\prime\prime}$ are attached to the same nitrogen atom, they can be combined with the nitrogen atom to form a 5-, 6-, or 7-membered ring. For example, —$NR^{d\prime}R^{d\prime\prime}$ can represent 1-pyrrolidinyl or 4-morpholinyl.

Typically, an alkyl or heteroalkyl group will have from zero to three substituents, with those groups having two or fewer substituents being exemplary of the present invention. An alkyl or heteroalkyl radical can be unsubstituted or monosubstituted. In some embodiments, an alkyl or heteroalkyl radical will be unsubstituted.

Exemplary substituents for the alkyl and heteroalkyl radicals include, but are not limited to —$OR^{d\prime}$, =O, =$NR^{d\prime}$, =N—$OR^{d\prime}$, —$NR^{d\prime}R^{d\prime\prime}$, —$SR^{d\prime}$, -halo, —$SiR^{d\prime}R^{d\prime\prime}R^{d\prime\prime\prime}$, —OC(O)$R^{d\prime}$, —C(O)$R^{d\prime}$, —$CO_2R^{d\prime}$, —CONR$^{d\prime}R^{d\prime\prime}$, —OC(O)NR$^{d\prime}R^{d\prime\prime}$, —$NR^{d\prime\prime}$C(O)$R^{d\prime}$, —$NR^{d\prime\prime\prime}$C(O)NR$^{d\prime}R^{d\prime\prime}$, —$NR^{d\prime\prime\prime}SO_2NR^{d\prime}R^{d\prime\prime}$, —$NR^{d\prime\prime}CO_2R^{d\prime}$, —NHC(NH$_2$)=NH, —$NR^{a\prime}$C(NH$_2$)=NH, —NHC(NH$_2$)=$NR^{d\prime}$, —S(O)$R^{d\prime}$, —$SO_2R^{d\prime}$, —$SO_2NR^{d\prime}R^{d\prime\prime}$, —$NR^{d\prime\prime}SO_2R^{d\prime}$, —CN, and —$NO_2$, where $R^{d\prime}$, $R^{d\prime\prime}$, and $R^{d\prime\prime\prime}$ are as defined above. Typical substituents can be selected from: —OR", =O, —$NR^{d\prime}R^{d\prime\prime}$, -halo, —OC(O)$R^{d\prime}$, —$CO_2R^{d\prime}$, —C(O)NR$^{d\prime}R^{d\prime\prime}$, —OC(O)NR$^{d\prime}R^{d\prime\prime}$, —$NR^{d\prime\prime}$C(O)$R^{d\prime}$, —$NR^{d\prime\prime}CO_2R^{d\prime}$, —$NR^{d\prime\prime\prime}SO_2NR^{d\prime}R^{d\prime\prime}$, —$SO_2R^{d\prime}$, —$SO_2NR^{d\prime}R^{d\prime\prime}$, —$NR^{d\prime\prime}SO_2R^{d\prime}$, —CN, and —$NO_2$.

Similarly, substituents for the aryl and heteroaryl groups are varied and selected from: -halo, —$OR^{e\prime}$, —OC(O)$R^{e\prime}$, —$NR^{e\prime}R^{e\prime\prime}$, —$SR^{e\prime}$, —$R^{e\prime}$, —CN, —$NO_2$, —$CO_2R^{e\prime}$, —C(O)NR$^{e\prime}R^{e\prime\prime}$, —C(O)$R^{e\prime}$, —OC(O)NR$^{e\prime}R^{e\prime\prime}$, —$NR^{e\prime\prime}$C(O)$R^{e\prime}$, —$NR^{e\prime\prime}CO_2R^{e\prime}$, —$NR^{e\prime\prime\prime}$C(O)NR$^{e\prime}R^{e\prime\prime}$, —$NR^{e\prime\prime\prime}SO_2NR^{e\prime}R^{e\prime\prime}$, —NHC(NH$_2$)=NH, —$NR^{e\prime}$C(NH$_2$)=NH, —NH—C(NH$_2$)=$NR^{e\prime}$, —S(O)$R^{e\prime}$, —$SO_2R^{e\prime}$, —$SO_2NR^{e\prime}R^{e\prime\prime}$, —$NR^{e\prime\prime}SO_2R^{e\prime}$, —$N_3$, —CH(Ph)$_2$, perfluoroalkoxy, and perfluoro($C_1$-$C_4$)alkyl, in a number ranging from zero to the total number of open valences on the aromatic ring system.

$R^{e\prime}$, $R^{e\prime\prime}$ and $R^{e\prime\prime\prime}$ are independently selected from hydrogen, unsubstituted ($C_1$-$C_8$) alkyl, unsubstituted hetero($C_1$-$C_8$) alkyl, unsubstituted aryl, unsubstituted heteroaryl, unsubstituted aryl($C_1$-$C_4$) alkyl, and unsubstituted aryloxy ($C_1$-$C_4$) alkyl. Typically, an aryl or heteroaryl group will have from zero to three substituents, with those groups having two or fewer substituents being exemplary in the present invention. In one embodiment of the invention, an aryl or heteroaryl group will be unsubstituted or monosubstituted. In another embodiment, an aryl or heteroaryl group will be unsubstituted.

Two of the substituents on adjacent atoms of an aryl or heteroaryl ring in an aryl or heteroaryl group as described herein may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -J-(CH$_2$)$_r$—K—, wherein J and K are independently —CH$_2$—, —O—, —NH—, —S—, —S(O)—, —S(O)$_2$—, —S(O)$_2$NR$^{f\prime}$—, or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR$^{f\prime}$—, —S—, —S(O)—, —S(O)$_2$—, or —S(O)$_2$NR$^{a\prime}$—. The substituent R$^{f\prime}$ in —NW'— and —S(O)$_2$NR$^{f\prime}$— is selected from hydrogen or unsubstituted ($C_1$-$C_6$) alkyl.

"Stable compound" and "stable structure" are meant to indicate a compound that is sufficiently robust to survive isolation to a useful degree of purity from a reaction mixture, and formulation into an efficacious therapeutic agent.

As used herein the term "therapeutically effective amount" generally means the amount necessary to ameliorate at least one symptom of a disorder to be prevented, reduced, or treated as described herein. The phrase "therapeutically effective amount" as it relates to the GSNOR inhibitors of the present invention shall mean the GSNOR inhibitor dosage that provides the specific pharmacological response for which the GSNOR inhibitor is administered in a significant number of subjects in need of such treatment. It is emphasized that a therapeutically effective amount of a GSNOR inhibitor that is administered to a particular subject in a particular instance will not always be effective in treating the conditions/diseases described herein, even though such dosage is deemed to be a therapeutically effective amount by those of skill in the art.

The term "biological sample" includes, but is not limited to, samples of blood (e.g., serum, plasma, or whole blood), urine, saliva, sweat, breast milk, vaginal secretions, semen, hair follicles, skin, teeth, bones, nails, or other secretions, body fluids, tissues, or cells. In accordance with the invention, the levels of the GSNOR in the biological sample can be determined by the methods described in U.S. Patent Application Publication No. 2005/0014697.

D. Pharmaceutical Compositions

The invention encompasses pharmaceutical compositions comprising at least one compound of the invention described herein and at least one pharmaceutically acceptable carrier.

Suitable carriers are described in "Remington: The Science and Practice, Twentieth Edition," published by Lippincott Williams & Wilkins, which is incorporated herein by reference. Pharmaceutical compositions according to the invention may also comprise one or more non-inventive compound active agents.

The pharmaceutical compositions of the invention can comprise novel compounds described herein, the pharmaceutical compositions can comprise known compounds which previously were not known to have GSNOR inhibitor activity, or a combination thereof.

The compounds of the invention can be utilized in any pharmaceutically acceptable dosage form, including, but not limited to injectable dosage forms, liquid dispersions, gels, aerosols, ointments, creams, lyophilized formulations, dry powders, tablets, capsules, controlled release formulations, fast melt formulations, delayed release formulations, extended release formulations, pulsatile release formulations, mixed immediate release and controlled release formulations, etc. Specifically, the compounds of the invention described herein can be formulated: (a) for administration selected from the group consisting of oral, pulmonary, intravenous, intra-arterial, intrathecal, intra-articular, rectal, ophthalmic, colonic, parenteral, otic, intracisternal, intravaginal, intraperitoneal, local, buccal, nasal, and topical administration; (b) into a dosage form selected from the group consisting of liquid dispersions, gels, aerosols, ointments, creams, tablets, sachets, and capsules; (c) into a dosage form selected from the group consisting of lyophilized formulations, dry powders, fast melt formulations, controlled release formulations, delayed release formulations, extended release formulations, pulsatile release formulations, and mixed immediate release and controlled release formulations; or (d) any combination thereof.

For respiratory infections, an inhalation formulation can be used to achieve high local concentrations. Formulations suitable for inhalation include dry power or aerosolized or vaporized solutions, dispersions, or suspensions capable of being dispensed by an inhaler or nebulizer into the endobronchial or nasal cavity of infected patients to treat upper and lower respiratory bacterial infections.

Solutions or suspensions used for parenteral, intradermal, or subcutaneous application can comprise one or more of the following components: (1) a sterile diluent such as water for injection, saline solution, fixed oils, polyethylene glycols, glycerine, propylene glycol, or other synthetic solvents; (2) antibacterial agents such as benzyl alcohol or methyl parabens; (3) antioxidants such as ascorbic acid or sodium bisulfite; (4) chelating agents such as ethylenediaminetetraacetic acid; (5) buffers such as acetates, citrates, or phosphates; and (5) agents for the adjustment of tonicity such as sodium chloride or dextrose. The pH can be adjusted with acids or bases, such as hydrochloric acid or sodium hydroxide. A parenteral preparation can be enclosed in ampoules, disposable syringes, or multiple dose vials made of glass or plastic.

Pharmaceutical compositions suitable for injectable use may comprise sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.), or phosphate buffered saline (PBS). In all cases, the composition must be sterile and should be fluid to the extent that easy syringability exists. The pharmaceutical composition should be stable under the conditions of manufacture and storage and should be preserved against the contaminating action of microorganisms such as bacteria and fungi.

The carrier can be a solvent or dispersion medium comprising, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol or sorbitol, and inorganic salts such as sodium chloride in the composition. Prolonged absorption of the injectable compositions can be brought about by including in the composition an agent which delays absorption, for example, aluminum monostearate and gelatin.

Sterile injectable solutions can be prepared by incorporating the active reagent in the required amount in an appropriate solvent with one or a combination of ingredients enumerated above, as required, followed by filtered sterilization. Generally, dispersions are prepared by incorporating at least one compound of the invention into a sterile vehicle that contains a basic dispersion medium and any other required ingredients. In the case of sterile powders for the preparation of sterile injectable solutions, exemplary methods of preparation include vacuum drying and freeze-drying, both of which yield a powder of a compound of the invention plus any additional desired ingredient from a previously sterile-filtered solution thereof.

Oral compositions generally include an inert diluent or an edible carrier. They can be enclosed, for example, in gelatin capsules or compressed into tablets. For the purpose of oral therapeutic administration, the compound of the invention can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition.

For administration by inhalation, the compounds are delivered in the form of an aerosol spray from pressured container or dispenser that contains a suitable propellant, e.g., a gas such as carbon dioxide, a nebulized liquid, or a dry powder from a suitable device. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active reagents are formulated into ointments, salves, gels, or creams as generally known in the art. The reagents can also be prepared in the form of suppositories (e.g., with conventional suppository bases such as cocoa butter and other glycerides) or retention enemas for rectal delivery.

In one embodiment, the compounds of the invention are prepared with carriers that will protect against rapid elimination from the body. For example, a controlled release formulation can be used, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, suspensions of the compounds of the invention may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also include suitable stabilizers or agents to increase the solubility of the compounds and allow for the preparation of highly concentrated solutions.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of the compound of the invention calculated to produce the desired therapeutic effect in association with the required pharmaceutical carrier. The specification for the dosage unit forms of the invention are dictated by and directly dependent on the unique characteristics of the compound of the invention and the particular therapeutic effect to be achieved, and the limitations inherent in the art of compounding such an active agent for the treatment of individuals.

Pharmaceutical compositions according to the invention comprising at least one compound of the invention can comprise one or more pharmaceutical excipients. Examples of such excipients include, but are not limited to binding agents, filling agents, lubricating agents, suspending agents, sweeteners, flavoring agents, preservatives, buffers, wetting agents, disintegrants, effervescent agents, and other excipients. Such excipients are known in the art. Exemplary excipients include: (1) binding agents which include various celluloses and cross-linked polyvinylpyrrolidone, microcrystalline cellulose, such as Avicel® PH101 and Avicel® PH102, silicified microcrystalline cellulose (ProSolv SMCC™), gum tragacanth and gelatin; (2) filling agents such as various starches, lactose, lactose monohydrate, and lactose anhydrous; (3) disintegrating agents such as alginic acid, Primogel, corn starch, lightly crosslinked polyvinyl pyrrolidone, potato starch, maize starch, and modified starches, croscarmellose sodium, cross-povidone, sodium starch glycolate, and mixtures thereof; (4) lubricants, including agents that act on the flowability of a powder to be compressed, include magnesium stearate, colloidal silicon dioxide, such as Aerosil® 200, talc, stearic acid, calcium stearate, and silica gel; (5) glidants such as colloidal silicon dioxide; (6) preservatives, such as potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride; (7) diluents such as pharmaceutically acceptable inert fillers, such as microcrystalline cellulose, lactose, dibasic calcium phosphate, saccharides, and/or mixtures of any of the foregoing; examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose; (8) sweetening agents, including any natural or artificial sweetener, such as sucrose, saccharin sucrose, xylitol, sodium saccharin, cyclamate, aspartame, and acesulfame; (9) flavoring agents, such as peppermint, methyl salicylate, orange flavoring, Magnasweet® (trademark of MAFCO), bubble gum flavor, fruit flavors, and the like; and (10) effervescent agents, including effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

E. Kits Comprising the Compositions of the Invention

The present invention also encompasses kits comprising the compositions of the invention. Such kits can comprise, for example, (1) at least one compound of the invention; and (2) at least one pharmaceutically acceptable carrier, such as a solvent or solution. Additional kit components can optionally include, for example: (1) any of the pharmaceutically acceptable excipients identified herein, such as stabilizers, buffers, etc., (2) at least one container, vial, or similar apparatus for holding and/or mixing the kit components; and (3) delivery apparatus, such as an inhaler, nebulizer, syringe, etc.

F. Methods of Preparing Compounds of the Invention

The compounds of the invention can readily be synthesized using known synthetic methodologies or via a modification of known synthetic methodologies. As would be readily recognized by a skilled artisan, the methodologies described below allow the synthesis of substituted bicyclic aromatic compoundss having a variety of substituents. Exemplary synthetic methods are described in the Examples section below.

If needed, further purification and separation of enantiomers and diastereomers can be achieved by routine procedures known in the art. Thus, for example, the separation of enantiomers of a compound can be achieved by the use of chiral HPLC and related chromatographic techniques. Diastereomers can be similarly separated. In some instances, however, diastereomers can simply be separated physically, such as, for example, by controlled precipitation or crystallization.

The process of the invention, when carried out as prescribed herein, can be conveniently performed at temperatures that are routinely accessible in the art. In one embodiment, the process is performed at a temperature in the range of about 25° C. to about 110° C. In another embodiment, the temperature is in the range of about 40° C. to about 100° C. In yet another embodiment, the temperature is in the range of about 50° C. to about 95° C.

Synthetic steps that require a base are carried out using any convenient organic or inorganic base. Typically, the base is not nucleophilic. Thus, in one embodiment, the base is selected from carbonates, phosphates, hydroxides, alkoxides, salts of disilazanes, and tertiary amines.

The process of the invention, when performed as described herein, can be substantially complete after several minutes to after several hours depending upon the nature and quantity of reactants and reaction temperature. The determination of when the reaction is substantially complete can be conveniently evaluated by ordinary techniques known in the art such as, for example, HPLC, LCMS, TLC, and $^1$H NMR.

G. Methods of Treatment

The invention encompasses methods of preventing or treating (e.g., alleviating one or more symptoms of) medical conditions through use of one or more of the disclosed compounds. The methods comprise administering a therapeutically effective amount of a compound of the invention to a patient in need. The compositions of the invention can also be used for prophylactic therapy.

The compound of the invention used in the methods of treatment according to the invention can be: (1) a novel compound described herein, or a pharmaceutically acceptable salt thereof, a stereoisomer thereof, a prodrug thereof, a metabolite thereof, or an N-oxide thereof; (2) a compound which was known prior to the present invention, but wherein it was not known that the compound is a GSNOR inhibitor, or a pharmaceutically acceptable salt thereof, a stereoisomer thereof, a prodrug thereof, a metabolite thereof, or an N-oxide thereof; or (3) a compound which was known prior to the present invention, and wherein it was known that the compound is a GSNOR inhibitor, but wherein it was not known that the compound is useful for the methods of treatment described herein, or a pharmaceutically acceptable salt, a stereoisomer, a prodrug, a metabolite, or an N-oxide thereof.

The patient can be any animal, domestic, livestock, or wild, including, but not limited to cats, dogs, horses, pigs, and cattle, and preferably human patients. As used herein, the terms patient and subject may be used interchangeably.

As used herein, "treating" describes the management and care of a patient for the purpose of combating a disease, condition, or disorder and includes the administration of a compound of the present invention to prevent the onset of the symptoms or complications, alleviating the symptoms or complications, or eliminating the disease, condition, or disorder. More specifically, "treating" includes reversing, attenuating, alleviating, minimizing, suppressing, or halting at least one deleterious symptom or effect of a disease (disorder) state, disease progression, disease causative agent (e.g., bacteria or viruses), or other abnormal condition. Treatment is continued as long as symptoms and/or pathology ameliorate.

In general, the dosage, i.e., the therapeutically effective amount, ranges from 1 µg/kg to 10 g/kg and often ranges from 10 µg/kg to 1 g/kg or 10 µg/kg to 100 mg/kg body weight of the subject being treated, per day.

H. GSNOR Uses

In subjects with deleteriously high levels of GSNOR or GSNOR activity, modulation may be achieved, for example, by administering one or more of the disclosed compounds that disrupts or down-regulates GSNOR function, or decreases GSNOR levels. These compounds may be administered with other GSNOR inhibitor agents, such as anti-GSNOR antibodies or antibody fragments, GSNOR antisense, iRNA, or small molecules, or other inhibitors, alone or in combination with other agents as described in detail herein.

The present invention provides a method of treating a subject afflicted with a disorder ameliorated by NO donor therapy. Such a method comprises administering to a subject a therapeutically effective amount of a GSNOR inhibitor.

The disorders can include pulmonary disorders associated with hypoxemia and/or smooth muscle constriction in the lungs and airways and/or lung infection and/or lung inflammation and/or lung injury (e.g., pulmonary hypertension, ARDS, asthma, pneumonia, pulmonary fibrosis/interstitial lung diseases, cystic fibrosis, COPD); cardiovascular disease and heart disease (e.g., hypertension, ischemic coronary syndromes, atherosclerosis, heart failure, glaucoma); diseases characterized by angiogenesis (e.g., coronary artery disease); disorders where there is risk of thrombosis occurring; disorders where there is risk of restenosis occurring; inflammatory diseases (e.g., AIDS related dementia, inflammatory bowel disease (IBD), Crohn's disease, colitis, and psoriasis); functional bowel disorders (e.g., irritable bowel syndrome (IBS)); diseases where there is risk of apoptosis occurring (e.g., heart failure, atherosclerosis, degenerative neurologic disorders, arthritis, and liver injury (e.g., drug induced, ischemic or alcoholic)); impotence; sleep apnea; diabetic wound healing; cutaneous infections; treatment of psoriasis; obesity caused by eating in response to craving for food; stroke; reperfusion injury (e.g., traumatic muscle injury in heart or lung or crush injury); and disorders where preconditioning of heart or brain for NO protection against subsequent ischemic events is beneficial, central nervous system (CNS) disorders (e.g., anxiety, depression, psychosis, and schizophrenia); and infections caused by bacteria (e.g., tuberculosis, C. difficile infections, among others).

In one embodiment, the disorder is liver injury. Liver injury can include, for example, acute liver toxicity. Acute liver toxicity can result in acute liver failure. Acute liver failure (ALF) is an uncommon but potentially lethal drug-related adverse effect that often leads to liver transplantation (LT) or death. Acetoaminophen is the most common cause of acute liver toxicity and acute liver failure, although acute liver toxicity can be due to other agents, such as alcohol and other drugs. Regardless of whether it occurs as a result of a single overdose or after repeated supratherapeutic ingestion, the progression of acetaminophen poisoning can be categorized into four stages: preclinical toxic effects (a normal serum alanine aminotransferase concentration), hepatic injury (an elevated alanine aminotransferase concentration), hepatic failure (hepatic injury with hepatic encephalopathy), and recovery. As long as sufficient glutathione is present, the liver is protected from injury. Overdoses of acetaminophen (either a single large ingestion or repeated supratherapeutic ingestion) can deplete hepatic glutathione stores and allow liver injury to occur. Compounds of the invention are capable of treating and/or preventing liver injury and/or acute liver toxicity. In this embodiment, appropriate amounts of compounds of the present invention are an amount sufficient to treat and/or prevent liver injury and can be determined without undue experimentation by preclinical and/or clinical trials. In one embodiment, the amount to treat is at least 0.001 mg/kg, at least 0.002 mg/kg, at least 0.003 mg/kg, at least 0.004 mg/kg, at least 0.005 mg/kg, at least 0.006 mg/kg, at least 0.007 mg/kg, at least 0.008 mg/kg, at least 0.009 mg/kg, at least 0.01 mg/kg, at least 0.02 mg/kg, at least 0.03 mg/kg, at least 0.04 mg/kg, at least 0.05 mg/kg, at least at least 0.06 mg/kg, at least 0.07 mg/kg, at least 0.08 mg/kg, at least 0.09 mg/kg, at least 0.1 mg/kg, at least 0.2 mg/kg, at least 0.3 mg/kg, at least 0.4 mg/kg, at least 0.5 mg/kg, at least 0.6 mg/kg, at least 0.7 mg/kg, at least 0.8 mg/kg, at least 0.9 mg/kg, at least 1 mg/kg, at least 1.5 mg/kg, at least 2 mg/kg, at least 2.5 mg/kg, at least 3 mg/kg, at least 3.5 mg/kg, at least 4 mg/kg, at least 4.5 mg/kg, at least 5 mg/kg, at least 6 mg/kg, at least 7 mg/kg, at least 8 mg/kg, at least 9 mg/kg, at least 10 mg/kg, at least 15 mg/kg, at least 20 mg/kg, at least 30 mg/kg, at least 40 mg/kg, at least 50 mg/kg, at least 60 mg/kg, at least 70 mg/kg, at least 80 mg/kg, at least 90 mg/kg, at least 100 mg/kg. The dosing can be hourly, four times, twice, or once daily, or four times, twice, or once per week, or weekly, or every other week, every third week, or monthly.

In one embodiment, the disorder is trauma (including surgery and thermal), infectious, toxic, aging, and ischemic damage to organs of known regenerative capacity, such as skin, gastric mucosa, airway epithelial and cartilaginous structures, liver, neuronal structures such as the spinal cord, bone marrow and bone. We have shown that inhibition of GSNOR by the use of highly specific small molecules treats, repairs, and promotes regeneration of mammalian tissue. By way of example, small molecule inhibitors are effective in treating, and promoting repair and regeneration of mammalian lung tissue damaged by instillation of a chemical agent known to cause severe lung injury (porcine pancreatic elastase) (Blonder et al., ATS 2011 abstract reference). In this embodiment, appropriate amounts of compounds of the present invention are an amount sufficient to regenerate tissue/organs and can be determined without undue experimentation by preclinical and/or clinical trials.

In one embodiment the disorder is trauma (including surgery and thermal), infectious, toxic, aging, and ischemic damage to organs of not commonly known to have regenerative capacity. Examples include regeneration of: the heart, the lung, the kidney, the central nervous system, the peripheral nervous system, peripheral vascular tissue, liver, pancreas, adrenal gland, thyroid, testes, ovary, retina, tongue, bone, bladder, esophagus, larynx, thymus, spleen, cartilaginous structures of the head, and cartilaginous structures of the joints. In this embodiment, appropriate amounts of compounds of the present invention are an amount sufficient to regenerate tissue/organs and can be determined without undue experimentation by preclinical and/or clinical trials.

In one embodiment ex and in vivo implantation and regeneration of organs and structures, including stem cells. In this embodiment, appropriate amounts of compounds of the present invention are an amount sufficient to regenerate tissue/organs and can be determined without undue experimentation by preclinical and/or clinical trials.

In one embodiment, the compounds of the present invention or a pharmaceutically acceptable salt thereof, or a prodrug, stereoisomer, metabolite, or N-oxide thereof, can be administered in combination with an NO donor. An NO donor donates nitric oxide or a related redox species and more generally provides nitric oxide bioactivity, that is activity which is identified with nitric oxide, e.g., vasorelaxation or stimulation or inhibition of a receptor protein, e.g., ras protein, adrenergic receptor, NFκB. NO donors including S-nitroso, O-nitroso, C-nitroso, and N-nitroso compounds and nitro derivatives thereof and metal NO complexes, but not excluding other NO bioactivity generating compounds, useful herein are described in "Methods in Nitric Oxide Research," Feelisch et al. eds., pages 71-115 (J. S., John Wiley & Sons, New York, 1996), which is incorporated herein by reference. NO donors which are C-nitroso compounds where nitroso is attached to a tertiary carbon which are useful herein include those described in U.S. Pat. No. 6,359,182 and in WO 02/34705. Examples of S-nitroso compounds, including S-nitrosothiols useful herein, include, for example, S-nitrosoglutathione, S-nitroso-N-acetylpenicillamine, S-nitroso-cysteine and ethyl ester thereof, S-nitroso cysteinyl glycine, S-nitroso-gamma-methyl-L-homocysteine, S-nitroso-L-homocysteine, S-nitroso-gamma-thio-L-leucine, S-nitroso-delta-thio-L-leucine, and S-nitrosoalbumin. Examples of other NO donors useful herein are sodium nitroprusside (nipride), ethyl nitrite, isosorbide, nitroglycerin, SIN 1 which is molsidomine, furoxamines, N-hydroxy (N-nitrosamine), and perfluorocarbons that have been saturated with NO or a hydrophobic NO donor.

The combination of a GSNOR inhibitor with R(+) enantiomer of amlodipine, a known NO releaser (Zhang at al., *J. Cardiovasc. Pharm.* 39: 208-214 (2002)) is also an embodiment of the present invention.

The present invention also provides a method of treating a subject afflicted with pathologically proliferating cells where the method comprises administering to said subject a therapeutically effective amount of an inhibitor of GSNOR. The inhibitors of GSNOR are the compounds as defined above, or a pharmaceutically acceptable salt thereof, or a stereoisomer, prodrug, metabolite, or N-oxide thereof, in combination with a pharmaceutically acceptable carrier. Treatment is continued as long as symptoms and/or pathology ameliorate.

In another embodiment, the pathologically proliferating cells can be pathologically proliferating microbes. The microbes involved can be those where GSNOR is expressed to protect the microbe from nitrosative stress or where a host cell infected with the microbe expresses the enzyme, thereby protecting the microbe from nitrosative stress. The term "pathologically proliferating microbes" is used herein to mean pathologic microorganisms including, but not limited to, pathologic bacteria, pathologic viruses, pathologic *Chlamydia*, pathologic protozoa, pathologic *Rickettsia*, pathologic fungi, and pathologic mycoplasmata. More detail on the applicable microbes is set forth at columns 11 and 12 of U.S. Pat. No. 6,057,367. The term "host cells infected with pathologic microbes" includes not only mammalian cells infected with pathologic viruses but also mammalian cells containing intracellular bacteria or protozoa, e.g., macrophages containing *Mycobacterium tuberculosis, Mycobacterium* leper (leprosy), or *Salmonella typhi* (typhoid fever).

In another embodiment, the pathologically proliferating cells can be pathologic helminths. The term "pathologic helminths" is used herein to refer to pathologic nematodes, pathologic trematodes and pathologic cestodes. More detail on the applicable helminths is set forth at column 12 of U.S. Pat. No. 6,057,367.

In another embodiment, the pathologically proliferating cells can be pathologically proliferating mammalian cells. The term "pathologically proliferating mammalian cells" as used herein means cells of the mammal that grow in size or number in said mammal so as to cause a deleterious effect in the mammal or its organs. The term includes, for example, the pathologically proliferating or enlarging cells causing restenosis, the pathologically proliferating or enlarging cells causing benign prostatic hypertrophy, the pathologically proliferating cells causing myocardial hypertrophy, and proliferating cells at inflammatory sites such as synovial cells in arthritis or cells associated with a cell proliferation disorder.

As used herein, the term "cell proliferative disorder" refers to conditions in which the unregulated and/or abnormal growth of cells can lead to the development of an unwanted condition or disease, which can be cancerous or non-cancerous, for example a psoriatic condition. As used herein, the term "psoriatic condition" refers to disorders involving keratinocyte hyperproliferation, inflammatory cell infiltration, and cytokine alteration. The cell proliferative disorder can be a precancerous condition or cancer. The cancer can be primary cancer or metastatic cancer, or both.

As used herein, the term "cancer" includes solid tumors, such as lung, breast, colon, ovarian, pancreas, prostate, adenocarcinoma, squamous carcinoma, sarcoma, malignant glioma, leiomyosarcoma, hepatoma, head and neck cancer, malignant melanoma, non-melanoma skin cancers, as well as hematologic tumors and/or malignancies, such as leukemia, childhood leukemia and lymphomas, multiple myeloma, Hodgkin's disease, lymphomas of lymphocytic and cutaneous origin, acute and chronic leukemia such as acute lymphoblastic, acute myelocytic, or chronic myelocytic leukemia, plasma cell neoplasm, lymphoid neoplasm, and cancers associated with AIDS.

In addition to psoriatic conditions, the types of proliferative diseases which may be treated using the compositions of the present invention are epidermic and dermoid cysts, lipomas, adenomas, capillary and cutaneous hemangiomas, lymphangiomas, nevi lesions, teratomas, nephromas, myofibromatosis, osteoplastic tumors, and other dysplastic masses, and the like. In one embodiment, proliferative diseases include dysplasias and disorders of the like.

In one embodiment, treating cancer comprises a reduction in tumor size, decrease in tumor number, a delay of tumor growth, decrease in metastatic lesions in other tissues or organs distant from the primary tumor site, an improvement in the survival of patients, or an improvement in the quality of patient life, or at least two of the above.

In another embodiment, treating a cell proliferative disorder comprises a reduction in the rate of cellular proliferation, reduction in the proportion of proliferating cells, a decrease in size of an area or zone of cellular proliferation, or a decrease in the number or proportion of cells having an abnormal appearance or morphology, or at least two of the above.

In yet another embodiment, the compounds of the present invention or a pharmaceutically acceptable salt thereof, a stereoisomer thereof, a prodrug thereof, a metabolite thereof, or an N-oxide thereof can be administered in combination with a second chemotherapeutic agent. In a further embodiment, the second chemotherapeutic agent is selected from the group consisting of tamoxifen, raloxifene, anastrozole, exemestane, letrozole, cisplatin, carboplatin, paclitaxel, cyclophosphamide, lovastatin, minosine, gemcitabine, araC, 5-fluorouracil, methotrexate, docetaxel, goserelin, vincristin, vinblastin, nocodazole, teniposide, etoposide, epothilone, navelbine, camptothecin, daunonibicin, dactinomycin, mitoxantrone, amsacrine, doxorubicin, epirubicin, idarubicin imatanib, gefitinib, erlotinib, sorafenib, sunitinib malate, trastuzumab, rituximab, cetuximab, and bevacizumab.

In one embodiment, the compounds of the present invention or a pharmaceutically acceptable salt thereof, a stereoisomer thereof, a prodrug thereof, a metabolite thereof, or an N-oxide thereof, can be administered in combination with an agent that imposes nitrosative or oxidative stress. Agents for selectively imposing nitrosative stress to inhibit proliferation of pathologically proliferating cells in combination therapy with GSNOR inhibitors herein and dosages and routes of administration therefor include those disclosed in U.S. Pat. No. 6,057,367, which is incorporated herein. Supplemental agents for imposing oxidative stress (i.e., agents that increase GSSG (oxidized glutathione) over GSH (glutathione) ratio or NAD(P) over NAD(P)H ratio or increase thiobarbituric acid derivatives) in combination therapy with GSNOR inhibitors herein include, for example, L-buthionine-5-sulfoximine (BSO), glutathione reductase inhibitors (e.g., BCNU), inhibitors or uncouplers of mitochondrial respiration, and drugs that increase reactive oxygen species (ROS), e.g., adriamycin, in standard dosages with standard routes of administration.

GSNOR inhibitors may also be co-administered with a phosphodiesterase inhibitor (e.g., rolipram, cilomilast, roflumilast, Viagra® (sildenifil citrate), Clalis® (tadalafil), Levitra® (vardenifil), etc.), a β-agonist, a steroid, an anti-muscarinics, or a leukotriene antagonist (LTD-4). Those skilled in the art can readily determine the appropriate therapeutically effective amount depending on the disorder to be ameliorated.

GSNOR inhibitors may be used as a means to improve β-adrenergic signaling. In particular, inhibitors of GSNOR alone or in combination with β-agonists could be used to treat or protect against heart failure, or other vascular disorders such as hypertension and asthma. GSNOR inhibitors can also be used to modulate G protein coupled receptors (GPCRs) by potentiating Gs G-protein, leading to smooth muscle relaxation (e.g., airway and blood vessels), and by attenuating Gq G-protein, and thereby preventing smooth muscle contraction (e.g., in airway and blood vessels).

The therapeutically effective amount for the treatment of a subject afflicted with a disorder ameliorated by NO donor therapy is the GSNOR inhibiting amount in vivo that causes amelioration of the disorder being treated or protects against a risk associated with the disorder. For example, for asthma, a therapeutically effective amount is a bronchodilating effective amount; for cystic fibrosis, a therapeutically effective amount is an airway obstruction ameliorating effective amount; for ARDS, a therapeutically effective amount is a hypoxemia ameliorating effective amount; for heart disease, a therapeutically effective amount is an angina relieving or angiogenesis inducing effective amount; for hypertension, a therapeutically effective amount is a blood pressure reducing effective amount; for ischemic coronary disorders, a therapeutic amount is a blood flow increasing effective amount; for atherosclerosis, a therapeutically effective amount is an endothelial dysfunction reversing effective amount; for glaucoma, a therapeutic amount is an intraocular pressure reducing effective amount; for diseases characterized by angiogenesis, a therapeutically effective amount is an angiogenesis inhibiting effective amount; for disorders where there is risk of thrombosis occurring, a therapeutically effective amount is a thrombosis preventing effective amount; for disorders where there is risk of restenosis occurring, a therapeutically effective amount is a restenosis inhibiting effective amount; for chronic inflammatory diseases, a therapeutically effective amount is an inflammation reducing effective amount; for disorders where there is risk of apoptosis occurring, a therapeutically effective amount is an apoptosis preventing effective amount; for impotence, a therapeutically effective amount is an erection attaining or sustaining effective amount; for obesity, a therapeutically effective amount is a satiety causing effective amount; for stroke, a therapeutically effective amount is a blood flow increasing or a TIA protecting effective amount; for reperfusion injury, a therapeutically effective amount is a function increasing effective amount; and for preconditioning of heart and brain, a therapeutically effective amount is a cell protective effective amount, e.g., as measured by troponin or CPK.

The therapeutically effective amount for the treatment of a subject afflicted with pathologically proliferating cells means a GSNOR inhibiting amount in vivo which is an antiproliferative effective amount. Such antiproliferative effective amount as used herein means an amount causing reduction in rate of proliferation of at least about 20%, at least about 10%, at least about 5%, or at least about 1%.

I. Uses in an Apparatus

The compounds of the present invention or a pharmaceutically acceptable salt thereof, or a stereoisomer, prodrug, metabolite, or N-oxide thereof, can be applied to various apparatus in circumstances when the presence of such compounds would be beneficial. Such apparatus can be any device or container, for example, implantable devices in which a compound of the invention can be used to coat a surgical mesh or cardiovascular stent prior to implantation in a patient. The compounds of the invention can also be applied to various apparatus for in vitro assay purposes or for culturing cells.

The compounds of the present invention or a pharmaceutically acceptable salt thereof, or a stereoisomer, a prodrug, a metabolite, or an N-oxide thereof, can also be used as an agent for the development, isolation or purification of binding partners to compounds of the invention, such as antibodies, natural ligands, and the like. Those skilled in the art can readily determine related uses for the compounds of the present invention.

EXAMPLES

The following examples are given to illustrate the present invention. It should be understood, however, that the invention is not to be limited to the specific conditions or details described in these examples. Throughout the specification, any and all references to a publicly available document, including a U.S. patent, are specifically incorporated by reference.

Example 1-32 list representative novel napthalene analogs of Formula 1 useful as GSNOR inhibitors of the invention. Synthetic methods that can be used to prepare each compound are described in Examples 1-32. Supporting mass spectrometry data and/or proton NMR data for each compound is also included in the Examples. Synthetic details for corresponding Intermediates are detailed in Example 34.

Example 1

3-chloro-4-(6-hydroxynaphthalen-2-yl)benzoic acid

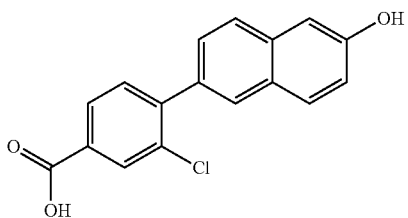 [SMILES: O=C(O)c1ccc(-c2ccc3cc(O)ccc3c2)c(Cl)c1]

A mixture of 6-bromonaphthalen-2-ol (500 mg, 2.20 mmol), 4-borono-3-chlorobenzoic acid (449 mg, 2.20 mmol), $K_3PO_4$ (1.40 g, 6.60 mmol) and $Pd(PPh_3)_4$ (200 mg, 0.170 mmol) in DMF (15 mL) and water (3 mL) was stirred under $N_2$ atmosphere at 80° C. for 3 hours. The resulting mixture was cooled to room temperature and diluted with water (50 mL) and extracted with ethyl acetate (50 mL×3). The aqueous phase was acidified with aqueous HCl until pH=2 and extracted with ethyl acetate (50 mL×3). The combined organic layers were dried over anhydrous $Na_2SO_4$ and concentrated under reduced pressure. The residue was purified by prep. HPLC (0.1% TFA as additive) to give compound Example 1 (59 mg, yield 9%) as an off-white solid. $^1$H NMR ($CD_3OD$ 400 MHz): δ 8.15 (d, J=1.6 Hz, 1H), 8.04 (dd, J=8.0, 1.6 Hz, 1H), 7.85 (s, 1H), 7.80 (d, J=8.8 Hz, 1H), 7.74 (d, J=8.4 Hz, 1H), 7.59 (d, J=8.0 Hz, 1H), 7.51 (dd, J=8.4, 1.6 Hz, 1H), 7.18 (d, J=2.0 Hz, 1H), 7.14 (dd, J=8.8, 2.4 Hz, 1H). MS (ESI): m/z 297.0 [M-1]$^-$.

Example 2

3-fluoro-4-(6-hydroxynaphthalen-2-yl)benzoic acid

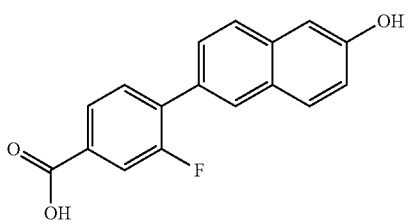 [SMILES: O=C(O)c1ccc(-c2ccc3cc(O)ccc3c2)c(F)c1]

6-Bromonaphthalen-2-ol (1 g, 4.48 mmol) was mixed with 880 mg of 2-fluoro-4-(methoxycarbonyl)phenylboronic acid (4.48 mmol), 1.2 g of $K_2CO_3$ (9.23 mmol), 120 mg of $Pd(PPh_3)_4$ (2.5 mol %), and then suspended in 17 mL of 1,4-Dioxane and 4 mL of $H_2O$. The mixture was degassed 3× with argon and then heated to reflux while stirring for 1 hour. 4N NaOH (5 mL) was then added and stirred at room temperature for 2 hours, back extracted with EtOAc, and filtered through Celite. The basic aqueous solution was then acidified to pH=4.3 and the solids were filtered to give about 950 mg of off-white solid. This was triturated in 8 mL DCM and 2 mL EtOAc and filtered to yield about 830 mg of off-white Example 2 (65.8% overall yield). $^1$H-NMR (DMSO-d6 500 MHz): δ 13.31 (bs, 1H), 9.97 (bs, 1H), 8.05 (s, 1H), 7.90 (m, 2H), 7.80 (m, 3H), 7.64 (dt, 1H), 7.19 (m, 2H); MS (ESI): m/z 281.53 [MA]$^-$.

Example 3

4-(6-hydroxynaphthalen-2-yl)-3-methoxybenzoic acid

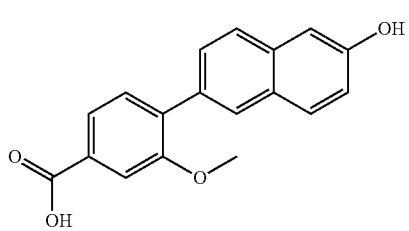 [SMILES: COc1cc(C(=O)O)ccc1-c1ccc2cc(O)ccc2c1]

A mixture of 6-bromonaphthalen-2-ol (124 mg, 0.559 mmol), 4-(dihydroxyboryl)-3-methoxybenzoic acid (100 mg, 0.510 mmol) and $K_2CO_3$ (211 mg, 1.53 mmol) in DME/$H_2O$ (7 mL/2 mL) was degassed three times under $N_2$. Then $PdCl_2$(dppf) (37 mg, 0.0559 mmol) was added and the mixture was heated to 110° C. for 3 hours. Followed the workup/purification procedure described in Example 1 to give Example 3 (60 mg, yield 37%) as a yellow solid. $^1$H NMR (DMSO 400 MHz): δ 13.00 (brs, 1H), 9.78 (brs, 1H), 7.89 (s, 1H), 7.80 (d, J=8.8 Hz, 1H) 7.70 (d, J=8.4 Hz, 1H), 7.65-7.57 (m, 2H), 7.55-7.45 (m, 2H), 7.10-7.02 (m, 2H), 3.85 (s, 3H). MS (ESI): m/z 293.0 [M–H]$^-$.

Example 4

5-(6-hydroxynaphthalen-2-yl)picolinic acid

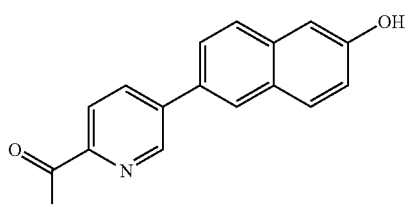

Step 1: Synthesis of methyl 5-(6-hydroxynaphthalen-2-yl)picolinate: A mixture of 6-bromonaphthalen-2-ol (250 mg, 1.13 mmol), methyl 5-(4,4,5,5-tetramethyl-1,3,2-dioxaborolan-2-yl)picolinate (355 mg, 1.35 mmol), Pd(dppf)Cl$_2$ (82 mg, 0.112 mmol) and sodium carbonate (263 mg, 2.48 mmol) in DME/water (3 mL/1 mL) was heated to 100° C. by microwave for 1 h. Then the mixture was partitioned with water (10 mL) and EA (20 mL). The precipitate was filtered off. The organic phase was separated, washed with brine (15 mL), dried over Na$_2$SO$_4$ and concentrated to give the product (180 mg, 57%) as a brown solid.

Step 2: Synthesis of Example 4: Methyl 5-(6-hydroxynaphthalen-2-yl)picolinate (180 mg, 0.66 mmol) was dissolved in THF/water (3 mL/1 mL), then sodium hydroxide (78 mg, 1.9 mmol) was added. The mixture was refluxed for 3 hours, concentrated and purified by prep-HPLC to afford Example 4 (55 mg, 31.4%) as a yellow powder. $^1$H NMR (DMSO-d$_6$ 500 MHz TMS): 9.95 (s, 1H), 9.13 (s, 1H), 8.36 (dd, J=2.0 Hz, J=8.0 Hz, 1H), 8.29 (s, 1H), 8.13 (d, J=8.5 Hz, 1H), 7.89 (d, J=8.5 Hz, 1H), 7.85 (s, 2H), 7.18-7.14 (m, 2H); MS (ESI): m/z 266.1 [M+1]$^+$.

Example 5

3-(dimethylamino)-4-(6-hydroxynaphthalen-2-yl)benzoic acid

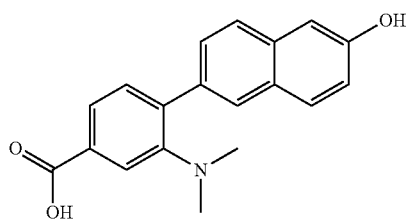 [SMILES: CN(C)c1cc(C(=O)O)ccc1-c1ccc2cc(O)ccc2c1]

Step 1: Synthesis of methyl 3-amino-4-(6-methoxynaphthalen-2-yl)benzoate A mixture of 2-bromo-6-methoxynaphthalene (10.0 g, 51.3 mmol). 2-amino-4-(methoxycarbonyl)phenylboronic acid (10 g) and K$_2$CO$_3$ (18.0 g, 133 mmol) in CH$_3$OCH$_2$CH$_2$OH/H$_2$O (140 mL/40 mL) was degassed three times under N$_2$. Then Pd(dppf)Cl$_2$ (3.10 g, 4.23 mmol) was added quickly and the mixture was heated to 60° C. for 1 hour. The mixture was diluted with H$_2$O (200 mL) and EtOAc (500 mL) and filtered. The filtrate was separated and the aqueous layer was extracted with EtOAc (100 mL×3), the combined organic layers were washed with brine (200 mL), dried over anhydrous Na$_2$SO$_4$ and concentrated under reduced pressure. The residue was purified by column chromatography on silica gel (PE/EtOAc=10/1) to give the product (4.20 g) as an off-white solid.

Step 2: Synthesis of methyl 3-(dimethylamino)-4-(6-methoxynaphthalen-2-yl)benzoate: To a solution of the above product (1.00 g, 3.30 mmol) in MeOH/CH$_2$Cl$_2$ (10 mL/20 mL) was added aqueous HCHO (37% aqueous, 5 mL), followed by NaBH$_3$CN (820 mg, 13.0 mmol) and ZnCl$_2$ (900 mg, 6.50 mmol) at 0° C. The mixture was stirred at 30° C. for 10 hours. The mixture was quenched with ice water (50 mL), the aqueous layer was extracted with CH$_2$Cl$_2$ (30 mL×3), the combined organic layer was washed with brine (50 mL), dried over anhydrous Na$_2$SO$_4$ and concentrated in vacuo to give the product (1.00 g, yield 90%).

Step 3: Synthesis of methyl 3-(dimethylamino)-4-(6-hydroxynaphthalen-2-yl)benzoate: To a solution of the above product (450 mg, 1.34 mmol) in anhydrous CH$_2$Cl$_2$ (10 mL) was added BBr$_3$ (0.6 mL 6.7 mmol) dropwise at 0° C. The mixture was stirred at 0° C. for 3 hours, then quenched with ice water (20 mL). The aqueous layer was extracted with EtOAc (20 mL×3), the combined organic layers washed with brine (50 mL), dried over anhydrous Na$_2$SO$_4$ and concentrated in vacuo to give the product (340 mg, yield 79%) as an off-white solid.

Step 4: Synthesis of 3-(dimethylamino)-4-(6-hydroxynaphthalen-2-yl)benzoic acid: To a solution of the above product (340 mg, 1.10 mmol) in THF/MeOH (8 mL/4 mL) was added aqueous LiOH (1 M, 4 mL). The mixture was stirred at 30° C. for 16 hours. The mixture was acidified with HCl (10%) to pH 6 and extracted with EtOAc (30 mL×3). The combined organic layers were washed with brine (20 mL), dried over anhydrous Na$_2$SO$_4$ and concentrated under reduced pressure. The residue was purified by prep-TLC (PE/EtOAc=1/1) to give Example 5 (25 mg, yield 8%) as a yellow solid. $^1$H NMR (MeOD 400 MHz): δ 7.91 (s, 1H), 7.80-7.70 (m, 2H), 7.70-7.63 (m, 3H), 7.15 (d, J=2.4 Hz, 1H), 7.10 (dd, J=8.8, 2.4 Hz, 2H), 2.65 (s, 6H). MS (ESI): m/z 308.1 [M+H]$^+$.

Example 6

3-cyano-4-(6-hydroxynaphthalen-2-yl)benzoic acid

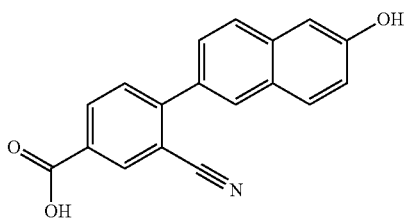 [SMILES: N#Cc1cc(C(=O)O)ccc1-c1ccc2cc(O)ccc2c1]

Step 1: Synthesis of methyl 3-cyano-4-(6-methoxynaphthalen-2-yl)benzoate: A mixture of methyl 3-cyano-4-(trifluoromethylsulfonyloxy)benzoate (Intermediate 1) (550 mg, 1.78 mmol), 6-methoxy-2-naphthaleneboronic acid (720 mg, 3.56 mmol), KOAc (700 mg, 7.12 mmol) and Pd(dppf)Cl$_2$ (100 mg, 0.122 mmol) in DME (10 mL), EtOH (10 mL) and water (10 mL) was stirred at 90° C. for 2 hours under N$_2$ atmosphere. The resulting mixture was cooled to room temperature, suspended in water (50 mL) and extracted with ethyl acetate (50 mL×3). The combined organic layers were dried over anhydrous Na$_2$SO$_4$ and concentrated in vacuo, then purified by column chromatography on silica gel (PE/EtOAc=20/1) to give the product (500 mg, yield: 89%) as an off-white solid.

Step 2: Synthesis of 3-cyano-4-(6-hydroxynaphthalen-2-yl)benzoic acid: A mixture of the above product (200 mg, 0.631 mmol) and BBr$_3$ (2 mL, 21.2 mmol) in anhydrous DCM (20 mL) was stirred at 25° C. overnight. The resulting mixture was quenched with water (50 mL) and extracted with ethyl acetate (50 mL×3). The combined organic layers were dried over anhydrous Na$_2$SO$_4$ and concentrated in vacuo. The residue was purified by prep-HPLC (0.1% TFA as additive) to give Example 6 (55 mg, yield 30%) as a off-white solid. $^1$H NMR (DMSO-d$_6$ 400 MHz): δ 13.54 (brs, 1H), 10.00 (brs, 1H), 8.37 (d, J=1.6 Hz, 1H), 8.26 (dd, J=8.4, 2.0 Hz, 1H), 8.06 (d, J=1.2 Hz, 1H), 7.92-7.82 (m, 3H), 7.63 (dd, J=8.4, 2.0 Hz, 1H), 7.22-7.12 (m, 2H). MS (ESI): m/z 290.0 [M+H]$^+$, 312.1 [M+Na]$^+$.

Example 7

6-(6-hydroxynaphthalen-2-yl)nicotinic acid

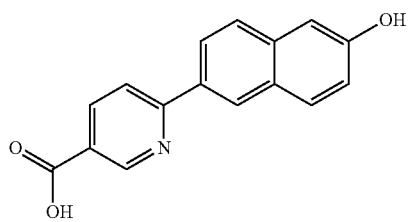 [SMILES: O=C(O)c1ccc(-c2ccc3cc(O)ccc3c2)nc1]

Step 1: Synthesis of methyl 6-(6-hydroxynaphthalen-2-yl)nicotinate: A mixture of 6-hydroxynaphthalen-2-ylboronic acid (250 mg, 1.33 mmol), methyl 6-bromonicotinate (260 mg, 1.21 mmol), Pd(dppf)Cl$_2$ (90 mg, 0.12 mmol) and sodium carbonate (205 mg, 2.41 mmol) in DME/water (3 mL/1 mL) was heated to 120° C. by microwave for 1 h. Then the mixture was partitioned with water (10 mL) and EA (20 mL). The precipitate was filtered off. The organic phase was separated, washed with brine (15 mL), dried over Na$_2$SO$_4$ and concentrated to afford product (crude, 380 mg) as a brown oil.

Step 2: Synthesis of 6-(6-hydroxynaphthalen-2-yl)nicotinic acid: methyl 6-(6-hydroxynaphthalen-2-yl)nicotinate (380 mg, 1.36 mmol) was dissolved in THF/water (6 mL/2 mL), then sodium hydroxide (164 mg, 4.09 mmol) was added. The mixture solution was heated to reflux for 3 hours, concentrated and purified by prep-HPLC to afford Example 7 (20 mg, 5.5%) as a powder. $^1$H NMR (MeOD-d$_4$ 500 MHz): 9.21 (s, 1H), 8.55 (dd, J=2.0 Hz, J=8.5 Hz, 1H), 8.51 (s, 1H), 8.19 (d, J=8.0 Hz, 1H), 8.09 (dd, J=2.0 Hz, J=9.0 Hz, 1H), 7.91 (d, J=8.0 Hz, 1H), 7.82 (d, J=9.0 Hz, 1H), 7.19-7.17 (m, 2H); MS (ESI): m/z 266.1 [M–H]$^+$.

Example 8

5-(6-hydroxynaphthalen-2-yl)pyrazine-2-carboxylic acid

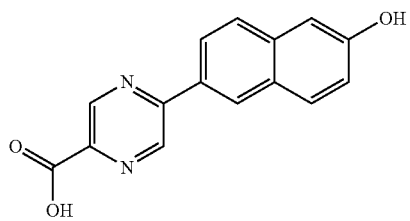 [SMILES: O=C(O)c1cnc(-c2ccc3cc(O)ccc3c2)cn1]

Followed the two step procedure described for Example 7 starting from 6-hydroxynaphthalen-2-ylboronic acid and methyl 5-chloropyrazine-2-carboxylate. $^1$H-NMR (MeOD-d$_4$ 500 MHz): 9.31 (s, 2H), 8.64 (s, 1H), 8.19-8.21 (d, J=9.0 Hz, 1H), 7.90-7.91 (d, J=8.5 Hz, 1H), 7.80-7.82 (d, J=8.5 Hz, 1H), 7.15-7.18 (t, J=2.0, 10.0 Hz, 2H). MS (ESI): m/z=267.0 [M+1]$^+$.

Example 9

2-(6-hydroxynaphthalen-2-yl)pyrimidine-5-carboxylic acid

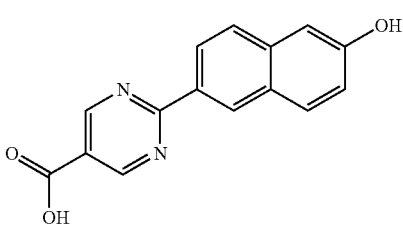 [SMILES: O=C(O)c1cnc(-c2ccc3cc(O)ccc3c2)nc1]

Followed procedure described in Step 1 of Example 7 starting from 6-hydroxynaphthalen-2-ylboronic acid and 2-chloropyrimidine-5-carboxylic acid with modifications: the solvent was dioxane/water (6/1), and the reaction was heated to 120° C. by microwave for 0.5 h. Purified by prep-HPLC. $^1$H-NMR (DMSO-d$_6$ 500 MHz): 13.70 (brs, 1H), 10.12 (s, 1H), 9.29 (s, 2H), 8.97 (s, 1H), 8.42-8.44 (d, J=9.0 Hz, 1H), 8.00-8.01 (d, J=8.5 Hz, 1H), 7.82-7.84 (d, J=9.0 Hz, 1H), 7.20 (s, 1H), 7.15-7.18 (dd, J=2.0, 9.0 Hz, 2H). MS (ESI): m/z=267.0 [M+1]$^+$.

Example 10

4-(6-hydroxynaphthalen-2-yl)-3-morpholinobenzoic acid

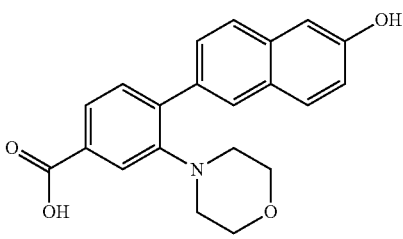 [SMILES: O=C(O)c1ccc(-c2ccc3cc(O)ccc3c2)c(N2CCOCC2)c1]

Step 1: Synthesis of methyl 4-(6-methoxynaphthalen-2-yl)-3-morpholinobenzoate: To a solution of methyl 3-amino-4-(6-methoxynaphthalen-2-yl)benzoate (1.00 g, 3.30 mmol) (see Step 1 of Example 5) and DIPEA (1.70 g, 13.2 mmol) in anhydrous toluene (20 mL) containing catalytic amount of KI (100 mg, 0.660 mmol) was added 2,2'-dibromodiethyl ether (1.50 g, 6.60 mmol). The mixture was heated to 110° C. for 3 days. The mixture was concentrated in vacuo and the residue was purified by column chromatography on silica gel (PE/EtOAc=10/1) to give the product (1.00 g, yield 81%).

Step 2: Synthesis of methyl 4-(6-hydroxynaphthalen-2-yl)-3-morpholinobenzoate: Followed the BBr$_3$ deprotection procedure described in Step 3 of Example 5.

Step 3: 4-(6-hydroxynaphthalen-2-yl)-3-morpholinobenzoic acid: Followed procedure described in Step 4 of Example 5, where reaction was run for 20 h at 25° C. The prep-HPLC purification (0.1% TFA as additive) gave Example 10 (54 mg, two-step yield 5.8%) as an off-white solid. $^1$H NMR (DMSO 400 MHz): δ 9.82 (brs, 1H), 8.00 (s, 1H) 7.80 (m, 2H), 7.74-7.60 (m, 3H), 7.39 (d, J=8.0 Hz, 1H), 7.13 (d, J=2.0 Hz, 1H), 7.08 (dd, J=8.8, 2.4 Hz, 1H), 3.52-3.47 (m, 4H), 2.80-2.72 (m, 4H). MS (ESI): m/z 349.9 [M+H]$^+$.

Example 11

6-(6-hydroxynaphthalen-2-yl)pyridazine-3-carboxylic acid

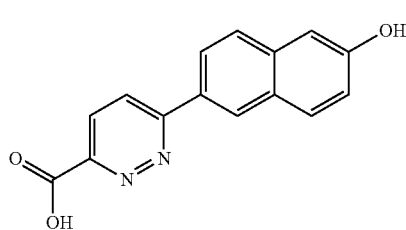 [SMILES: O=C(O)c1ccc(-c2ccc3cc(O)ccc3c2)nn1]

Followed the two step procedure described for Example 7 starting from 6-hydroxynaphthalen-2-ylboronic acid and methyl 6-chloropyridazine-3-carboxylate. $^1$H-NMR (DMSO-$d_6$ 500 MHz): 10.16 (s, 1H), 8.71 (d, J=5.0 Hz, 1H), 8.51-8.48 (m, 1H), 8.30-8.23 (m, 2H), 7.97-7.86 (m, 2H), 7.23-7.19 (m, 2H). MS (ESI): m/z 267.0 [M+1]$^+$.

Example 12

4-(1-bromo-6-hydroxynaphthalen-2-yl)benzoic acid

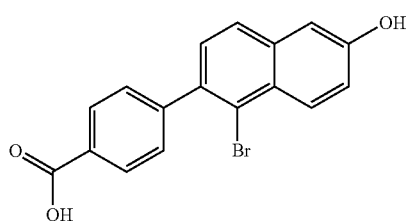 [SMILES: O=C(O)c1ccc(-c2ccc3cc(O)ccc3c2Br)cc1]

Step 1: Synthesis of methyl 4-(1-bromo-6-methoxynaphthalen-2-yl)benzoate: Followed the coupling procedure described for Example 1, starting from 1-bromo-6-methoxynaphthalen-2-yl trifluoromethanesulfonate (Intermediate 2) and 4-(methoxycarbonyl)phenylboronic acid with modifications: the base used was Na$_2$CO$_3$, the solvent was toluene/EtOH (4/1), and the reaction was heated to 80° C. for 3 h. The crude product was purified by silica gel column (PE/EtOAc=300/1 to 100/1), then washed with EtOAc (10 mL×5) to give the product (980 mg, yield 45%) as a white solid.

Step 2: Synthesis of 4-(1-bromo-6-hydroxynaphthalen-2-yl)benzoic acid: To a solution of above product (200 mg, 0.539 mmol) in anhydrous DCM (10 mL) was added BBr$_3$ (0.26 mL, 2.70 mmol, d=2.64 g/mL) dropwise at 0° C. The resulting mixture was stirred at 25° C. for 2 hours. The reaction mixture was quenched with H$_2$O (30 mL), then extracted with DCM (20 mL×3). The combined organic layers were washed with brine (20 mL), dried over anhydrous Na$_2$SO$_4$, filtered and concentrated. The crude product was purified by prep-HPLC (0.1% TFA as additive). Most of CH$_3$CN was removed under reduced pressure and the remaining solvent was removed by lyophilization to give Example 12 (70 mg, yield: 39%) as a white solid. $^1$H NMR (DMSO-$d_6$ 400 MHz): δ 13.05 (brs, 1H), 10.16 (brs, 1H), 8.16 (d, J=9.2 Hz, 1H), 8.04 (d, J=8.4 Hz, 2H), 7.82 (d, J=8.4 Hz, 1H), 7.57 (d, J=8.4 Hz, 2H), 7.37 (d, J=8.4 Hz, 1H), 7.32-7.21 (m, 2H). MS (ESI): m/z 341.0 [M−H]$^−$.

Example 13

4-(6-hydroxy-1-methylnaphthalen-2-yl)benzoic acid

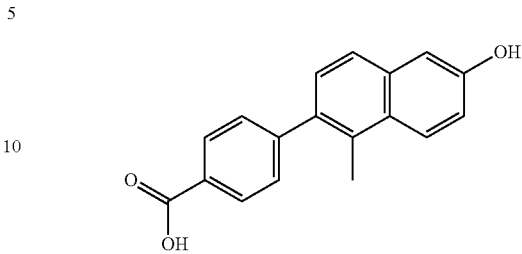

Step 1: Synthesis of methyl 4-(6-methoxy-1-methylnaphthalen-2-yl)benzoate: A mixture of methyl 4-(1-bromo-6-methoxynaphthalen-2-yl)benzoate (300 mg, 0.811 mmol) (see Example 12 step 1), MeZnCl (1.2 mL, 2.40 mmol, 2M in THF) and Pd(PPh$_3$)$_4$ (93.8 mg, 0.0811 mmol) in anhydrous THF (10 mL) was stirred at 60° C. under N$_2$ atmosphere for 16 hours. After cooling to room temperature, the mixture was quenched with saturated aqueous NH$_4$Cl (20 mL), extracted with EtOAc (20 mL×3). The combined organic layers were washed with H$_2$O (20 mL) and brine (20 mL), dried over anhydrous Na$_2$SO$_4$, filtered and concentrated under reduced pressure to give the crude product. The crude product was purified by silica gel column (PE/EtOAc=300/1 to 200/1) to give the product (210 mg, yield 85%) as a solid.

Step 2: Synthesis of methyl 4-(6-hydroxy-1-methylnaphthalen-2-yl)benzoate: Followed the BBr$_3$ deprotection procedure described for Step 2 of Example 12, except the crude product was taken forward without purification.

Step 3: Synthesis of Example 13: To a solution of the above product (200 mg, crude from above) in MeOH (8 mL) was added aqueous NaOH (8 mL, 2M). The mixture was stirred at 25° C. for 16 hours. To the reaction mixture was added H$_2$O (30 mL), extracted with EtOAc (15 mL×2) and discarded; the aqueous layer was acidified with 1N HCl to pH=1-2, extracted with EtOAc (15 mL×3). The combined organic layers were washed with brine (20 mL), dried over anhydrous Na$_2$SO$_4$, filtered and concentrated. Purification by prep-HPLC (0.1% TFA as additive); then most of CH$_3$CN was removed in vacuo followed by lyophilization to give Example 13 (25 mg, 2-step yield 13%) as an off-white solid. $^1$H NMR (MeOD 400 MHz): δ 8.09 (d, J=8.0 Hz, 2H), 7.99 (d, J=8.8 Hz, 1H), 7.55 (d, J=8.4 Hz, 1H), 7.45 (d, J=8.0 Hz, 2H), 7.25 (d, J=8.4 Hz, 1H), 7.20-7.10 (m, 2H), 2.53 (s, 3H). MS (ESI): m/z 300.9 [M+Na]$^+$.

Example 14

5-(6-hydroxynaphthalen-2-yl)pyrimidine-2-carboxylic acid

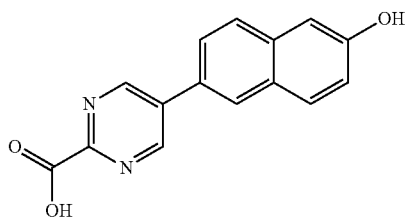 [SMILES: O=C(O)c1ncc(-c2ccc3cc(O)ccc3c2)cn1]

Followed the two step procedure described for Example 7 starting from 6-hydroxynaphthalen-2-yl boronic acid and methyl 5-bromopyrimidine-2-carboxylate. $^1$H-NMR (DMSO-$d_6$ 500 MHz): 9.39 (s, 2H), 8.38 (s, 1H), 7.87-7.91 (t, J=8.5, 12.0 Hz, 3H), 7.17-7.20 (t, J=5.5, 10.5 Hz, 2H). MS (ESI): m/z=267.0 [M+1]$^+$.

Example 15

4-(1-cyano-6-hydroxynaphthalen-2-yl)benzoic acid

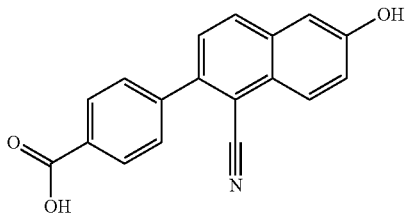 [SMILES: N#Cc1c(-c2ccc(C(=O)O)cc2)ccc2cc(O)ccc12]

Step 1: Synthesis of methyl 4-(1-cyano-6-methoxynaphthalen-2-yl)benzoate: To a solution of methyl 4-(1-bromo-6-methoxynaphthalen-2-yl)benzoate (300 mg, 0.811 mmol) (see Example 12 step 1) in DMF (10 mL) was added Zn(CN)$_2$ (191 mg, 1.62 mmol) and Pd(PPh$_3$)$_4$ (93.8 mg, 0.0811 mmol). The resulting mixture was stirred at 120° C. under N$_2$ atmosphere for 16 hours. After cooling to room temperature, the mixture was filtered and the filtrate was diluted with EtOAc (60 mL), washed with H$_2$O (20 mL×3) and brine (20 mL), dried over anhydrous Na$_2$SO$_4$, filtered and concentrated in vacuo. Purification by silica gel column (PE/EtOAc=200/1 to 50/1) gave the product (210 mg, yield 82%) as a solid.

Step 2: Synthesis of methyl 4-(1-cyano-6-hydroxynaphthalen-2-yl)benzoate: Followed the BBr$_3$ deprotection procedure described for Step 2 of Example 12, except the crude product was taken forward without purification.

Step 3: Synthesis of Example 15: To a solution of above product (160 mg, crude from above) in THF (16 mL) was added aqueous LiOH (4 mL, 2M). The mixture was stirred at 25° C. for 16 hours. To the reaction mixture was added H$_2$O (30 mL), extracted with EtOAc and discarded; then aqueous layer acidified with 1N HCl to pH=5-6, extracted with EtOAc (15 mL×3), washed with brine, dried over anhydrous Na$_2$SO$_4$, filtered and concentrated. The crude product was washed with EtOAc (10 mL) to give Example 15 (65 mg, 2-step yield 34%) as a pale-yellow solid. $^1$H NMR (DMSO-d$_6$ 400 MHz): δ 8.17 (d, J=8.8 Hz, 1H), 8.12-8.05 (m, 3H), 7.79 (d, J=8.4 Hz, 2H), 7.65 (d, J=8.8 Hz, 1H), 7.42 (dd, J=8.8 Hz, 2.4 Hz, 1H), 7.37 (d, J=2.4 Hz, 1H). MS (ESI): m/z 288.0 [M–H]$^-$.

Example 16

4-(6-hydroxy-3-methoxynaphthalen-2-yl)benzoic acid

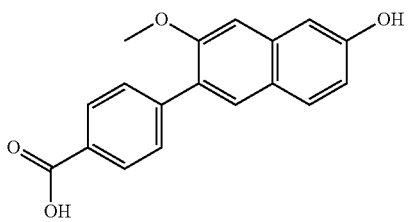 [SMILES: COc1cc2cc(O)ccc2cc1-c1ccc(C(=O)O)cc1]

Followed the coupling procedure described for Example 3, starting from 6-bromo-7-methoxynaphthalen-2-ol (Intermediate 3) and 4-boronobenzoic acid with a purification by prep-HPLC (0.1% TFA as additive) to give Example 16 (93 mg, yield 36%) as an off-white solid. $^1$H NMR (DMSO 400 MHZ): δ 9.72 (brs, 1H), 7.92 (d, J=8.4 Hz, 2H), 7.68-7.63 (m, 2H), 7.60 (d, J=8.4 Hz, 2H), 7.17 (s, 1H), 7.02 (d, J=2.0 Hz, 1H), 6.87 (dd, J=8.8, 2.0 Hz, 1H), 3.79 (s, 3H). MS (ESI): m/z 293.1 [M+H]$^+$.

Example 17

4-(1-chloro-6-hydroxynaphthalen-2-yl)benzoic acid

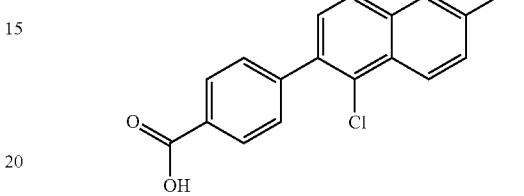

Step 1: Synthesis of 4-(1-chloro-6-methoxynaphthalen-2-yl)benzoic acid: Followed the coupling procedure described for Example 3, starting from 1-chloro-6-methoxynaphthalen-2-yl trifluoromethanesulfonate (Intermediate 4, 1 equiv) and 4-boronobenzoic acid (1.2 equiv), where the mixture was stirred at 80° C. for 2 hours. The crude product was obtained after workup and was taken on without purification.

Step 2: Synthesis of Example 17: Followed the deprotection method described in Step 2 of Example 12 to give Example 17 (50 mg, yield 28%) as an off-white solid. $^1$H NMR (MeOD 400 MHz): δ 8.22 (d, J=9.2 Hz, 1H), 8.10 (d, J=8.4 Hz, 2H), 7.68 (d, J=8.4 Hz, 1H), 7.58 (d, J=8.4 Hz, 2H), 7.36 (d, J=8.4 Hz, 1H), 7.23 (dd, J=9.2 Hz, 2.4 Hz, 1H), 7.18 (d, J=2.4 Hz, 1H). MS (ESI): m/z 297.0 [M–H]$^-$.

Example 18

6-(4-(1H-tetrazol-5-yl)phenyl)naphthalen-2-ol

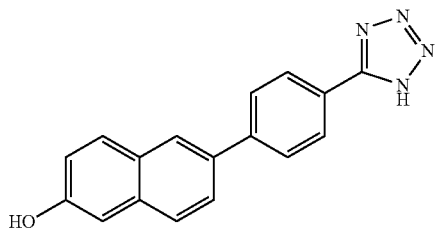 [SMILES: Oc1ccc2cc(-c3ccc(-c4nnn[nH]4)cc3)ccc2c1]

Followed the coupling procedure described in step 1 of Example 7, starting from 6-bromonaphthalen-2-ol and 4-(1H-tetrazol-5-yl)phenylboronic acid where the reaction was run (EtOH as a co-solvent and K$_2$CO$_3$ as the base) for 1.5 h at 150° C. The reaction mixture was filtered through Celite and washed with 1N NaOH. The mother liquor was then acidified to a pH of about 4 with conc. HCl. The resulting solid was filtered, washed with H$_2$O, and dried in vacuo to yield the crude product. This was taken up in hot ethanol, treated with activated charcoal, and allowed to recrystallize from the EtOH. Isolated Example 18 by filtration (108 mg, 17%). $^1$H NMR (DMSO-d$_6$ 500 MHz): δ 9.90 (s, 1H), 8.23 (s, 1H), 8.14 (d, 2H), 8.05 (d, 2H), 7.90 (d, 1H), 7.82 (s, 2H), 7.17 (m, 2H). MS (ESI): m/z 289.02 [M+1]+.

Example 19

6-(1H-benzo[d][1,2,3]triazol-6-yl)naphthalen-2-ol

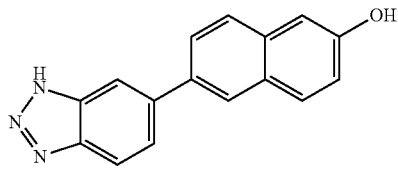 [SMILES: Oc1ccc2cc(-c3ccc4nn[nH]c4c3)ccc2c1]

Followed the coupling procedure described for Step 1 of Example 7, starting from 6-bromonaphthalen-2-ol and 1H-benzo[d][1,2,3]triazol-6-ylboronic acid where the base used was K₂CO₃ and the reaction was run in the microwave for 2 h at 150° C. Purification by flash chromatography with a mobile phase gradient of 0% to 75% EtOAc in hexanes gave Example 19 as an off-white powder (7.5 mg, 6.4% yield). ¹H NMR (DMSO-d₆ 500 MHz): δ 9.84 (s, 1H), 8.20 (s, 2H), 8.03 (d, 1H), 7.90 (m, 4H), 7.17 (m, 2H); MS (ESI): m/z 262.06 [M+1]+.

Example 20

4-(6-hydroxynaphthalen-2-yl)-3-(trifluoromethyl) benzoic acid

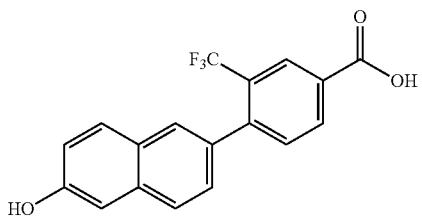 [SMILES: O=C(O)c1ccc(-c2ccc3cc(O)ccc3c2)c(C(F)(F)F)c1]

Step 1: Synthesis of 4-(6-methoxynaphthalen-2-yl)-3-(trifluoromethyl)benzoic acid: To a mixture of methyl 4-bromo-3-(trifluoromethyl)benzoate (Intermediate 5) (5.20 g), 2-bromo-6-methoxy-naphthalene (1.50 g, 6.33 mmol), and K₂CO₃ (1.75 g, 12.7 mmol) in DEGME/H₂O (70 mL/10 mL) was added Pd(dppf)Cl₂ (114 mg, 0.139 mmol) under N₂ atmosphere. The mixture was heated to 120° C. for 3 hours. H₂O (150 mL) was added, extracted with EtOAc (50 mL×2). The aqueous layer was acidified with 1N aqueous HCl to pH=3-4, extracted with EtOAc (50 mL×3), washed with brine (50 mL), dried over anhydrous Na₂SO₄, filtered and concentrated. The crude product was purified by silica gel column (PE/EtOAc=10/1 to 1/1) to give the product (1.10 g) as a brown solid.

Step 2: Synthesis of Example 20: To a solution of the above product (1.10 g, from above crude) in anhydrous DCM (15 mL) was added BBr₃ (2.0 mL, 21.1 mmol, d=2.64 g/mL) dropwise at 0° C. The mixture was stirred at 25° C. for 16 hours, then quenched with H₂O (90 mL) and extracted with DCM (30 mL×3). The combined organic layers were washed with brine (30 mL), dried over anhydrous Na₂SO₄, filtered and concentrated to give the crude product which was purified by prep-HPLC (0.1% TFA as additive). Most of CH₃CN was removed under reduced pressure and the remaining solvent was removed by lyophilization to give Example 20 (21 mg) as an off-white solid. ¹H NMR (MeOD 400 MHz): δ 8.40 (s, 1H), 8.27 (d, J=8.0 Hz, 1H), 7.74 (d, J=8.8 Hz, 1H), 7.72-7.68 (m, 2H), 7.56 (d, J=8.0 Hz, 1H), 7.34 (d, J=8.8 Hz, 1H), 7.19-7.08 (m, 2H). MS (ESI): m/z 331.0 [M–H]−.

Example 21

3-chloro-4-(3-fluoro-6-hydroxynaphthalen-2-yl)benzoic acid

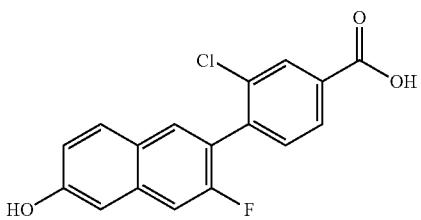 [SMILES: O=C(O)c1ccc(-c2cc3ccc(O)cc3cc2F)c(Cl)c1]

Step 1: Synthesis of 3-chloro-4-(3-fluoro-6-methoxynaphthalen-2-yl)benzoic acid: Followed the coupling procedure described in Step 1 of Example 20, where the starting materials were 3-fluoro-2-iodo-6-methoxynaphthalene (Intermediate 6) and 4-carboxy-2-chlorophenylboronic acid and wherein the reaction was heated to 90° C. for 3 hours. The desired product (380 mg, yield 70%) was isolated as a solid after workup.

Step 2: Synthesis of Example 21: Followed the BBr₃ deprotection described for Example 20, Step 2. Example 21 was isolated (45 mg, yield 12%) as an off-white solid. ¹H NMR (DMSO-d₆ 400 MHz): δ 13.41 (brs, 1H), 10.05 (brs, 1H), 8.06 (d, J=1.6 Hz, 1H), 7.99 (dd, J=8.0, 1.6 Hz, 1H), 7.85 (d, J=8.0 Hz, 2H), 7.68-7.56 (m, 2H), 7.17 (d, J=2.4 Hz, 1H), 7.10 (dd, J=8.8, 2.4 Hz, 1H). MS (ESI): m/z 315.0 [M–H]−.

Example 22

4-(3-chloro-6-hydroxynaphthalen-2-yl)benzoic acid

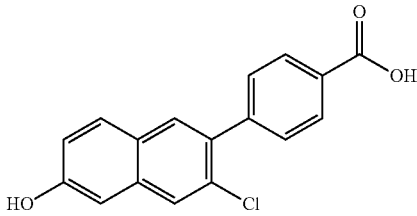 [SMILES: O=C(O)c1ccc(-c2cc3ccc(O)cc3cc2Cl)cc1]

Step 1: Synthesis of 4-(3-chloro-6-methoxynaphthalen-2-yl)benzoic acid: Followed the coupling procedure described in Step 1 of Example 20, starting from 3-chloro-2-iodo-6-methoxynaphthalene (Intermediate 7) and 4-carboxyphenylboronic acid, where the reaction was stirred under N₂ atmosphere at 90° C. for 4 hours. After workup, the residue was triturated with DCM (50 mL) to give the product (220 mg, yield: 75%) as an off-white solid.

Step 2: Synthesis of Example 22: A mixture of the above product (100 mg, 0.320 mmol) and BBr₃ (0.4 mL, 4.2 mmol) in anhydrous DCM (2.5 mL) was stirred at 15° C. for 2 days. Followed the workup/purification procedure described in Step 2 of Example 20 to give Example 22 (24 mg, yield 25%) as off-white solid. ¹H NMR (DMSO-d₆ 400 MHz): δ 13.02 (brs, 1H), 10.04 (brs, 1H), 8.02 (d, J=8.0 Hz, 2H), 7.96 (s, 1H), 7.87 (s, 1H), 7.84 (d, J=8.8 Hz, 1H), 7.61 (d, J=8.0 Hz, 2H), 7.16-7.08 (m, 2H). MS (ESI): m/z 297.0 [M–H]⁻.

Example 23

4-(3-fluoro-6-hydroxynaphthalen-2-yl)benzoic acid

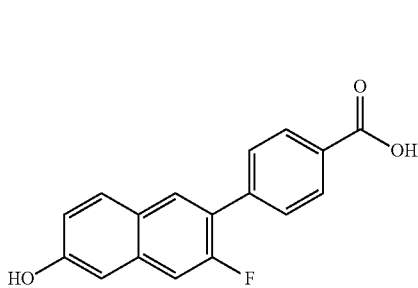 [SMILES: O=C(O)c1ccc(-c2cc3ccc(O)cc3cc2F)cc1]

Step 1: Synthesis of 4-(3-fluoro-6-methoxynaphthalen-2-yl)benzoic acid: Followed the coupling procedure described in Step 1 of Example 20, starting from 3-fluoro-2-iodo-6-methoxynaphthalene (Intermediate 6) and 4-carboxyphenylboronic acid. The reaction was heated to 90° C. for 3 hours. The product was isolated after workup (80 mg, crude).

Step 2: Synthesis of Example 23: Followed the BBr₃ deprotection described for Example 20, Step 2. Example 23 (11 mg, 2-step yield 2%) was isolated as an off-white solid. ¹H NMR (MeOD 400 MHz): δ 8.10 (d, J=8.4 Hz, 2H), 7.89 (d, J=8.0 Hz, 1H), 7.78 (d, J=8.8 Hz, 1H), 7.71 (d, J=6.8 Hz, 2H), 7.40 (d, J=12.4 Hz, 1H), 7.09 (d, J=2.0 Hz, 1H), 7.05 (dd, J=8.8, 2.0 Hz, 1H). MS (ESI): m/z 281.0 [M–H]⁻.

Example 24

4-(6-hydroxy-1-methoxynaphthalen-2-yl)benzoic acid

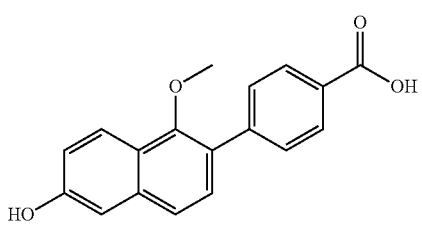 [SMILES: COc1c(-c2ccc(C(=O)O)cc2)ccc2cc(O)ccc12]

Step 1: Synthesis of 4-(6-(benzyloxy)-1-methoxynaphthalen-2-yl)benzoic acid: Followed the coupling procedure described in Step 1 of Example 20, where the starting materials were 6-(benzyloxy)-2-bromo-1-methoxynaphthalene (Intermediate 9) and 4-carboxyphenylboronic acid and where the reaction was stirred at 130° C. for 5 hours. The product (96 mg, yield 43%) was isolated as a yellow solid.

Step 2: Synthesis of Example 24: A mixture of the above product (96 mg, 0.25 mmol) and 10% Pd/C (100 mg, 50% wet) in EtOAc (10 mL) was stirred under H₂ (15 psi) at 30° C. for 18 hours. The mixture was filtered and the filtrate was concentrated in vacuo. The residue was purified by prep-TLC (PE/EtOAc=2/1) to give Example 24 (13.5 mg, yield 19%) as an off-white solid. ¹H NMR (CD₃OD 400 MHz TMS): δ 8.18-8.06 (m, 3H), 7.78 (d, J=8.4 Hz, 2H), 7.51 (d, J=8.8 Hz, 1H), 7.42 (d, J=8.4 Hz, 1H), 7.14 (s, 1H), 7.13 (d, J=7.6 Hz, 1H), 3.55 (s, 3H). MS (ESI): m/z 293.0 [M–H]⁻.

Example 25

4-(1-fluoro-6-hydroxynaphthalen-2-yl)benzoic acid

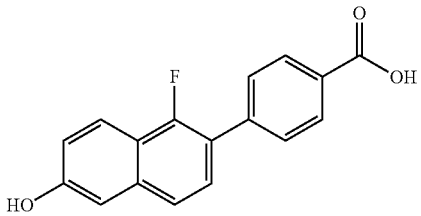 [SMILES: O=C(O)c1ccc(-c2ccc3cc(O)ccc3c2F)cc1]

Step 1: Synthesis of methyl 4-(1-fluoro-6-methoxynaphthalen-2-yl)benzoate: A mixture of 1-fluoro-6-methoxynaphthalen-2-yltrifluoromethanesulfonate (Intermediate 10) (80.0 mg, 0.247 mmol), 4-methoxycarbonylphenylboronic acid (44.5 mg, 0.247 mmol) and aqueous Na₂CO₃ (2M, 0.27 mL, 0.54 mmol) in toluene/EtOH (4 mL/1 mL) was degassed three times under N₂ atmosphere. Then Pd(PPh₃)₄ (28.6 mg, 0.0247 mmol) was added and the mixture was stirred at 80° C. for 5 hours under N₂ atmosphere. An aqueous/EtOAc workup was followed by silica gel column chromatography (PE/EtOAc=200/1 to 100/1) to give the product (50 mg, yield 65%) as an off-white solid.

Step 2: Synthesis of methyl 4-(1-fluoro-6-hydroxynaphthalen-2-yl)benzoate: To a solution of the above product (50.0 mg, 0.161 mmol) in anhydrous DCM (5 mL) was added BBr₃ (0.20 mL, 2.1 mmol, d=2.64 g/mL) dropwise at 0° C. The resulting mixture was stirred at 25° C. for 16 hours. An aqueous/DCM workup gave the product (50 mg, crude) as an off-white solid, which was used for next step directly. MS (ESI): m/z 295.0 [M–H]⁻.

Step 3: Synthesis of Example 25: Followed the hydrolysis procedure described for Step 3 of Example 13 to give Example 25 (5 mg, 2-step yield: 11%) as a white solid. ¹H NMR (MeOD 400 MHz): δ 8.12 (d, J=8.4 Hz, 2H), 8.02 (d, J=8.8 Hz, 1H), 7.75 (d, J=7.6 Hz, 2H), 7.58-7.47 (m, 2H), 7.21-7.12 (m, 2H). MS (ESI): m/z 281.0 [M–H]⁻.

Example 26

4-(6-hydroxy-3-methylnaphthalen-2-yl)benzoic acid

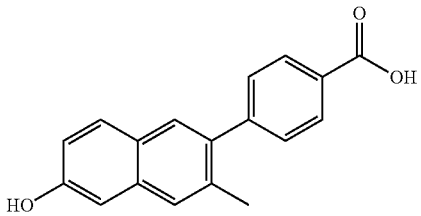

Step 1: Synthesis of 4-(6-(benzyloxy)-3-(methoxymethoxy)naphthalen-2-yl)benzoic acid: Followed the coupling procedure described in Step 1 of Example 20, where the starting materials were 6-(benzyloxy)-2-bromo-3-(methoxymethoxy)naphthalene (Intermediate 11) and 4-methoxycarbonylphenylboronic acid and where the reaction was stirred at 90° C. for 3 hours. The desired product (1.30 g, yield 72%) was obtained as an off-white solid.

Step 2: Synthesis of methyl 4-(6-(benzyloxy)-3-(methoxymethoxy) naphthalen-2-yl)benzoate: A mixture of the above product (1.20 g, 2.90 mmol), K₂CO₃ (800 mg, 5.80 mmol) and CH₃I (824 mg, 5.80 mmol) in DMF (15 mL) was stirred at 10° C. for 4 hours. The mixture was neutralized with aqueous HCl (0.1M) until pH=7 and extracted with EtOAc (50 mL×3). The combined organic layers were washed with brine (100 mL), dried over Na₂SO₄ and concentrated in vacuo to give the product (1.10 g, yield 89%) as an off-white solid.

Step 3: Synthesis of methyl 4-(6-(benzyloxy)-3-hydroxynaphthalen-2-yl)benzoate: To a solution of the above product (1.10 g, 2.57 mmol) in THF/MeOH (8 mL/2 mL) was added conc. HCl (0.2 mL). The mixture was refluxed for 3 hours. The mixture was concentrated under reduced pressure to give the crude product, which was washed with PE (50 mL) and EtOAc (30 mL) to give the product (900 mg, yield 91%) as white solid.

Step 4: Synthesis of methyl 4-(6-(benzyloxy)-3-(((trifluoromethyl)sulfonyl)oxy)naphthalen-2-yl)benzoate: To a solution of the above product (615 mg, 1.60 mmol) and Et₃N (1.30 g, 12.9 mmol) in DCM (20 mL) was added Tf₂O (903 mg, 3.20 mmol) dropwise and then the mixture was stirred at 10° C. for 30 minutes. After an aqueous/EtOAc workup, the residue was purified by silica gel column (PE/EtOAc=40/1) to give the product (450 mg, yield: 54%) as an off-white solid.

Step 5: Synthesis of methyl 4-(6-(benzyloxy)-3-methylnaphthalen-2-yl)benzoate: To a solution of ZnCl₂ (1.32 g, 9.68 mmol) in anhydrous THF (20 mL) was added MeMgCl (1.6 mL, 4.80 mmol, 3M in THF) and the mixture was stirred at under N₂ atmosphere at 10° C. for 1 hour. Then methyl 4-(6-(benzyloxy)-3-(((trifluoromethyl)sulfonyl)oxy)naphthalen-2-yl)benzoate (500 mg, 0.968 mmol) and Pd(PPh₃)₄ (100 mg, 0.0865 mmol) was added and the mixture was stirred at 60° C. under N₂ atmosphere for 3 hours. After an aqueous/EtOAc workup, the residue was purified by silica gel column (PE/EtOAc=40/1) to give the product (250 mg, yield 68%) as an off-white solid.

Step 6: Synthesis of 4-(6-(benzyloxy)-3-methylnaphthalen-2-yl)benzoic acid: A mixture of the above product (150 mg, 0.392 mmol) and aqueous NaOH (10 mL, 2M) in MeOH (10 mL) was refluxed overnight. The mixture was cooled to room temperature, acidified with aqueous HCl (2M) until pH=5 and extracted with EtOAc (50 mL×3), dried over Na₂SO₄ and concentrated in vacuo to give the product (100 mg, yield 69%) as off-white solid.

Step 7: Synthesis of Example 26: A mixture of the above product (100 mg, 0.271 mmol) and 10% Pd/C (50 mg, 50% wet) in EtOAc (10 mL) was stirred at 20° C. for 2 days. The mixture was filtered and the filtrate was concentrated under reduced pressure. The residue was purified by prep-HPLC (0.1% TFA as additive) to give Example 26 (60 mg, yield 79%) as off-white solid. $^1$H NMR (CD₃OD 400 MHz TMS): δ 8.09 (d, J=8.0 Hz, 2H), 7.69 (d, J=8.8 Hz, 1H), 7.58 (s, 1H), 7.54 (s, 1H), 7.49 (d, J=8.0 Hz, 2H), 7.06 (d, J=2.4 Hz, 1H), 7.02 (dd, J=8.4, 2.4 Hz, 1H), 2.35 (s, 3H). MS (ESI): m/z 277.0 [M−H]⁻.

Example 27

4-(1-cyano-5-fluoro-6-hydroxynaphthalen-2-yl)benzoic acid

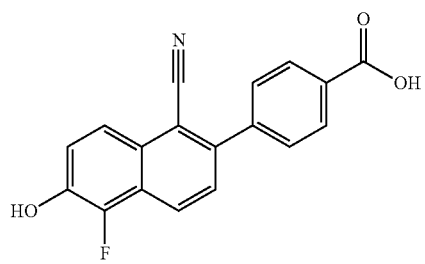 [SMILES: N#Cc1c(-c2ccc(C(=O)O)cc2)ccc2c(F)c(O)ccc12]

Step 1: Synthesis of methyl 4-(1-cyano-5-fluoro-6-methoxynaphthalen-2-yl)benzoate: To a solution of methyl 4-(1-cyano-6-methoxynaphthalen-2-yl)benzoate (1.66 g, 5.23 mmol) (described in step 1 of Example 15) in CH₃CN (30 mL) was added Selectfluor (2.04 g, 5.75 mmol). The reaction mixture was heated at 60° C. for 3 h and concentrated. The residue was partitioned between water (20 mL) and EtOAc (50 mL). The aqueous phase was separated and extracted with EtOAc. The combined organic layers were washed with brine, dried over MgSO₄, filtered and concentrated. The residue was purified by silica gel chromatography (PE/EA=4/1) to give the product (1.1 g, crude).

Step 2: Synthesis of Example 27: To an ice cooled solution of the above product (1.1 g, 3.3 mmol) in DCM (2 mL) was added BBr₃ (3 M in DCM, 10 mL, 30 mmol). The reaction mixture was stirred at room temperature overnight and slowly quenched with water and extracted with EtOAc. The combined organic layers were dried over MgSO₄, filtered and concentrated. The residue was washed with a mixture of DMF and CH₃CN. The solid was washed by CH₃CN, dried in high vacuum to give Example 27 (0.31 g, 31%) as white powder. $^1$H-NMR (DMSO-d₆, 500 MHz, TMS): δ 13.19 (s, 1H), 10.75 (s, 1H), 8.31 (d, J=9.0 Hz, 1H), 8.12 (d, J=8.0 Hz, 2H), 7.93 (d, J=9.0 Hz, 1H), 7.83 (d, J=8.0 Hz, 2H), 7.78 (d, J=9.0 Hz, 1H), 7.60 (t, J=8.5 Hz, 1H). MS (ESI): m/z=306.0 [M−1]⁺.

Example 28

4-(1-cyano-6-hydroxynaphthalen-2-yl)-3-fluorobenzoic acid

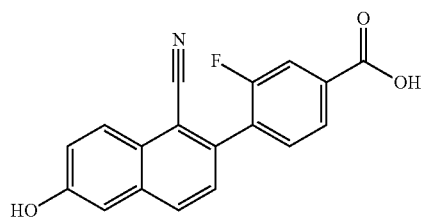 [SMILES: N#Cc1c(-c2ccc(C(=O)O)cc2F)ccc2cc(O)ccc12]

Step 1: Synthesis of methyl 4-(1-cyano-6-methoxynaphthalen-2-yl)-3-fluorobenzoate: Followed procedure described for Example 6, step 1 with modification: Pd(PPh₃)₄ was the catalyst, sodium carbonate was the base, and solvent used was toluene/EtOH/water (5/2/1). Purification by silica gel chromatography (PE/EA=2/1) gave the desired product (430 mg, 85%) as white solid.

Step 2: Synthesis of Example 28: To an ice cooled solution of the above product (280 mg, 0.83 mmol) in DCM (2 mL) was added BBr$_3$ (3 M in DCM, 3 mL, 9 mmol). The reaction mixture was stirred at room temperature overnight and slowly quenched with water (40 mL). The precipitate was collected by filtration and purified by prep-HPLC to give Example 28 (132 mg, 51%) as yellow solid. $^1$H-NMR (DMSO-d$_6$, 500 MHz, TMS): δ 13.48 (s, 1H), 10.41 (s, 1H), 8.20 (d, J=8.5 Hz, 1H), 8.07 (d, J=8.5 Hz, 1H), 7.94 (dd, J=9.0 Hz, 1H), 7.87 (dd, J=11.0 Hz, 1H), 7.76 (t, J=7.5 Hz, 1H), 7.61 (d, J=8.5 Hz, 1H), 7.43 (dd, J=9.5 Hz, 1H), 7.39 (d, J=2.0 Hz, 1H). MS (ESI): m/z=308.1 [M+1]$^+$.

Example 29

3-chloro-4-(5-fluoro-6-hydroxynaphthalen-2-yl)benzoic acid

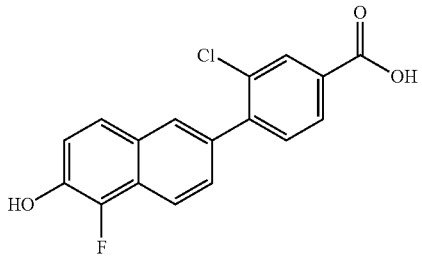 [SMILES: O=C(O)c1ccc(-c2ccc3c(F)c(O)ccc3c2)c(Cl)c1]

6-Bromo-1-fluoronaphthalen-2-ol (Intermediate 13, 1.0 mmol) and 4-borono-3-chlorobenzoic acid (2.0 mmol) were mixed with 5% (Ph$_3$P)$_4$Pd and NaHCO$_3$ (4.0 mmol) in 20 ml of 50% dioxane/water. The mixture was degassed three times by evacuation and argon filling and heated at 95° C. overnight. The reaction was diluted with 20 ml of water and filtered. The filtrate was acidified with 1N HCl to pH=4. The precipitate was filtered and washed with water, dried. The crude was purified by column using AcOH/MeOH/EtOAC (1/5/94) as solvent B and hexanes as solvent A with gradient 2 to 100% B to give a white solid. The solid was triturated with diisopropyl ether to give Example 29 (50 mg). $^1$H-NMR (DMSO-d$_6$, 300 MHz, TMS): δ 13.40 (b, 1H), 10.25 (b, 1H), 8.06 (s, 1H), 7.91-7.97 (m, 3H), 7.62-7.71 (m, 3H), 7.32 (t, 1H), MS (ESI): m/z=315.3 [M−1]$^−$.

Example 30

4-(5-fluoro-6-hydroxynaphthalen-2-yl)benzoic acid

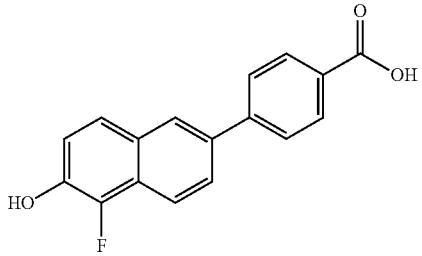 [SMILES: O=C(O)c1ccc(-c2ccc3c(F)c(O)ccc3c2)cc1]

Followed the coupling procedure described in Example 29 starting from 6-bromo-1-fluoronaphthalen-2-ol (Intermediate 13) and 4-boronobenzoic acid. $^1$H-NMR (DMSO-d$_6$, 300 MHz, TMS): δ 13.04 (b, 1H), 10.23 (b, 1H), 8.29 (s, 1H), 7.91-8.01 (m, 7H), 7.74 (d, 1H). MS (ESI): m/z=281.26 [M−1]$^−$.

Example 31

3-fluoro-4-(5-fluoro-6-hydroxynaphthalen-2-yl)benzoic acid

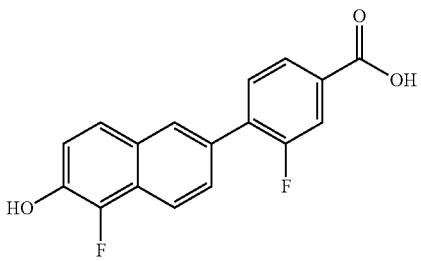 [SMILES: O=C(O)c1ccc(-c2ccc3c(F)c(O)ccc3c2)c(F)c1]

Followed the coupling procedure described in Example 29 starting from 6-bromo-1-fluoronaphthalen-2-ol (Intermediate 13) and 4-borono-3-fluorobenzoic acid. $^1$H-NMR (DMSO-d$_6$, 300 MHz, TMS): δ 13.32 (b, 1H), 10.28 (b, 1H), 8.14 (s, 1H), 7.98 (d, 1H), 7.78 (d, 1H), 7.73-7.76 (m, 4H), 7.32 (t, 1H), MS (ESI): m/z=299.40 [M−1]$^−$.

Example 32

4-(5-fluoro-6-hydroxynaphthalen-2-yl)-3-methylbenzoic acid

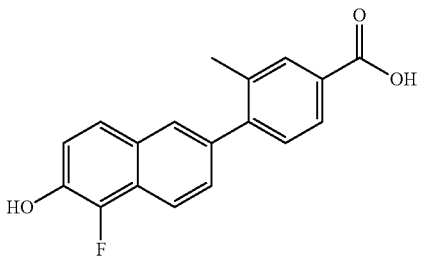 [SMILES: Cc1cc(C(=O)O)ccc1-c1ccc2c(F)c(O)ccc2c1]

Followed the coupling procedure described in Example 29 starting from 6-bromo-1-fluoronaphthalen-2-ol (Intermediate 13) and methyl 3-methyl-4-(4,4,5,5-tetramethyl-1,3,2-dioxaborolan-2-yl)benzoate. $^1$H-NMR (DMSO-d$_6$, 300 MHz, TMS): δ 12.90 (b, 1H), 10.17 (b, 1H), 7.84-7.97 (m, 4H), 7.70 (d, 1H), 7.54 (d, 1H), 7.41 (d, 1H), 7.30 (t, 1H), 2.33 (s, 3H). MS (ESI): m/z=295.25 [MA]$^−$.

Example 33

4-(6-hydroxynaphthalen-2-yl)benzoic acid

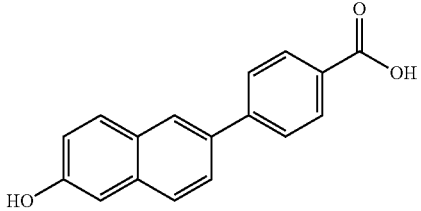 [SMILES: O=C(O)c1ccc(-c2ccc3cc(O)ccc3c2)cc1]

Followed the coupling procedure described in Example 3, starting from 6-bromonaphthalen-2-ol and 4-boronobenzoic acid, where the reaction was heated at 85° C. for 8 h. After the prep-HPLC purification, a further purification by silica gel column (PE:EA=7:1 to 4:1) gave the compound as a yellow solid (26 mg, 7%). $^1$H NMR (DMSO-d6 500 MHz TMS): δ 12.97 (brs, 1H), 9.91 (brs, 1H), 8.19 (s, 1H), 8.04 (d, J=8.0 Hz, 2H), 7.87-7.92 (m, 3H), 7.80 (m, 2H), 7.13-7.16 (m, 2H); MS (ESI): m/z 265.1 [M+1]$^+$.

Example 34

Synthesis of Intermediates

Intermediate 1: methyl 3-cyano-4-(trifluoromethylsulfonyloxy)benzoate

Step 1: Synthesis of methyl 3-cyano-4-hydroxybenzoate: A mixture of methyl 3-bromo-4-hydroxybenzoate (2.50 g, 10.8 mmol) and CuCN (1.10 g, 12.3 mmol) in NMP (10 mL) was stirred at 200° C. under $N_2$ atmosphere for 3 hours. The reaction mixture was cooled to room temperature and filtered. The filtrate was diluted in ethyl acetate (100 mL) and washed with water (50 mL×3) and brine (50 mL), then dried over anhydrous $Na_2SO_4$ and concentrated in vacuo. The residue was purified by column chromatography on silica gel (PE/EtOAc=8/1).

Step 2: Synthesis of Intermediate 1: To a mixture of crude methyl 3-cyano-4-hydroxybenzoate (2.50 g) from above and $Et_3N$ (1.31 g, 13.0 mmol) in anhydrous DCM (20 mL) was added $Tf_2O$ (1.82 g, 6.50 mmol) dropwise and then the reaction mixture was stirred at 30° C. for 2 hours. The resulting mixture was suspended in water (50 mL) and extracted with DCM (50 mL×3), dried over anhydrous $Na_2SO_4$ and concentrated in vacuo. The residue was purified by column chromatography on silica gel (PE/EtOAc=10/1) to give Intermediate 1 (550 mg, 2-step yield: 28%) as a colorless oil. $^1$H NMR (CDCl$_3$ 300 MHz): δ 8.43 (d, J=2.1 Hz, 1H), 8.37 (dd, J=8.7, 2.1 Hz, 1H), 7.59 (d, J=8.7 Hz, 1H), 3.98 (s, 3H).

Intermediate 2: 1-bromo-6-methoxynaphthalen-2-yl trifluoromethanesulfonate

Step 1: Synthesis of 1-bromo-6-methoxynaphthalen-2-ol: To a solution of 6-methoxynaphthalen-2-ol (2.00 g, 11.5 mmol) in DMF (20 mL) was added NBS (2.15 g, 12.1 mmol) and the reaction mixture was stirred at 25° C. for 4 hours. The resulting mixture was diluted with EtOAc (300 mL), washed with $H_2O$ (100 mL×5) and brine (100 mL), dried over anhydrous $Na_2SO_4$ and concentrated in vacuo to give the crude product, which was purified by silica gel column (PE/EtOAc=20/1) to give the product (2.10 g, yield 72%).

Step 2: Synthesis of 1-bromo-6-methoxynaphthalen-2-yl trifluoromethanesulfonate: To a solution of above product (2.70 g, 10.7 mmol) and TEA (1.41 g, 13.9 mmol) in anhydrous DCM (30 mL) was added $Tf_2O$ (3.33 g, 11.8 mmol) at −50° C. and the reaction mixture was stirred at the same temperature for 0.5 hour. The resulting mixture was quenched with brine (150 mL), extracted with DCM (50 mL×3). The combined organic layers were washed with brine (50 mL), dried over anhydrous $Na_2SO_4$ and concentrated in vacuo to give crude Intermediate 2 (3.80 g) as a solid. $^1$H NMR (CDCl$_3$ 400 MHz): δ 8.17 (d, J=9.6 Hz, 1H), 7.74 (d, J=9.2 Hz, 1H), 7.36 (d, J=9.2 Hz, 1H), 7.31 (dd, J=9.2, 2.4 Hz, 1H), 7.14 (d, J=2.8 Hz, 1H), 3.93 (s, 3H).

Intermediate 3: 6-bromo-7-methoxynaphthalen-2-ol

Step 1: Synthesis of 3-bromonaphthalene-2,7-diol: To a solution of naphthalene-2,7-diol (5.00 g, 31.3 mmol) in AcOH (25 mL) was added $Br_2$ (3.3 mL, 62.6 mmol) in AcOH (25 mL) dropwise over 15 minutes at 10-15° C., then mixture was stirred at 10-15° C. for 1 hour. Sn powder (7.75 g, 64.6 mmol) and $H_2O$ (20 mL) was added and the mixture was heated to 80° C. for 1 hour. The mixture was diluted with ice-water (50 mL), the extracted with EtOAc (30 mL×3), organic was washed with brine (50 mL), dried over $Na_2SO_4$, filtered and concentrated. Purification by column chromatography on silica gel (PE/EtOAc=15/1) and further prep-HPLC (0.1% TFA as additive) gave the product (2.0 g, yield 27%) as a solid.

Step 2: Synthesis of 6-bromo-7-methoxynaphthalen-2-ol: To a solution of above product (500 mg, 2.08 mmol) in DMF (12 mL) was added $K_2CO_3$ (579 mg, 4.17 mmol). The mixture was stirred at 25° C. for 20 minutes under $N_2$. A solution of $CH_3I$ (260 mg, 1.83 mmol) in DMF (1 mL) was added via syringe pump over 2 hours. The mixture was stirred at 25° C. for 30 minutes. The mixture was acidified with 2M HCl to pH=5. The mixture was extracted with DCM (20 mL×3). The combined organic layers were washed with brine (50 mL), dried over anhydrous $Na_2SO_4$ and concentrated in vacuo, then purified by column chromatography on silica gel (PE/EtOAc=10/1) to give Intermediate 3 (260 mg, yield 49%) as a white solid. $^1$H NMR (CDCl$_3$ 400 MHz): δ 7.96 (s, 1H), 7.59 (d, J=8.4 Hz, 1H), 7.05 (d, J=2.4 Hz, 1H), 7.00 (s, 1H), 6.97 (dd, J=8.8, 2.4 Hz, 1H), 5.05 (s, 1H), 3.91 (s, 3H).

Intermediate 4: 1-chloro-6-methoxynaphthalen-2-yl trifluoromethanesulfonate Step 1: Synthesis of 1-chloro-6-methoxynaphthalen-2-ol: To a solution of 6-methoxynaphthalen-2-ol (1.00 g, 5.74 mmol) in DMF (15 mL) was added NCS (843 mg, 6.31 mmol). The reaction mixture was stirred at 25° C. for 16 hours. Diluted the reaction with EtOAc, washed with $H_2O$ and brine, dried over anhydrous $Na_2SO_4$, filtered and concentrated in vacuo. Purification by silica gel column (PE/EtOAc=100/1) gave the product (940 mg, yield 87%).

Step 2: Synthesis of 1-chloro-6-methoxynaphthalen-2-yl trifluoromethanesulfonate: Followed procedure described in Step 2 of Intermediate 2. $^1$H NMR (CDCl$_3$ 400 MHz): δ 8.21 (d, J=9.2 Hz, 1H), 7.71 (d, J=9.2 Hz, 1H), 7.39 (d, J=9.2 Hz, 1H), 7.34 (dd, J=9.2, 2.4 Hz, 1H), 7.16 (d, J=2.4 Hz, 1H), 3.95 (s, 3H).

Intermediate 5: methyl 4-(4,4,5,5-tetramethyl-1,3,2-dioxaborolan-2-yl)-3-(trifluoromethyl)benzoate To a mixture of methyl 4-bromo-3-(trifluoromethyl)benzoate (2.00 g, 7.07 mmol), bis(pinacolato)diboron (3.60 g, 14.1 mmol), and KOAc (2.08 g, 21.2 mmol) in DMSO (30 mL) was added Pd(PPh$_3$)$_4$ (1.63 g, 1.41 mmol) under $N_2$ atmosphere. Then the mixture was heated to 120° C. for 3 hours. The reaction mixture was diluted with EtOAc (150 mL). The organic phase was separated, washed with $H_2O$ (50 mL×3) and brine (50 mL), dried over anhydrous $Na_2SO_4$, filtered and concentrated to give the crude product (5.2 g) as a yellow oil.

Intermediate 6: 3-fluoro-2-iodo-6-methoxynaphthalene

Step 1: Synthesis of tert-butyl (7-methoxynaphthalen-2-yl)carbamate: A mixture of 7-methoxynaphthalen-2-amine (84.0 g, 485 mmol) and Boc$_2$O (116 g, 534 mmol) in THF (500 mL) was stirred at 65° C. overnight. The mixture was concentrated. Purification by silica gel column (PE/EtOAc=50/1) gave the product (95.0 g, yield 71%) as off-white solid.

Step 2: To a mixture of the above product (20.0 g, 73.2 mmol) in anhydrous THF (1000 mL) was added t-BuLi (350 mL, 455 mmol, 1.3 M in pentane) dropwise at −20° C. under $N_2$ atmosphere. The reaction mixture was stirred at −10° C. for 30 minutes. Then 1,2-diiodoethane (51.6 g, 183 mmol)

was added and the mixture was stirred at 20° C. for 1 hour. The mixture was quenched with water (1000 mL) and extracted with ethyl acetate (1000 mL×3). The combined organic layers were dried over anhydrous $Na_2SO_4$, concentrated, and then purified by silica gel column (PE/EtOAc=200/1~5/1) to give tert-butyl (6-iodo-7-methoxynaphthalen-2-yl)carbamate (8.15 g, yield 28%) and a mixture of isomers (8.55 g) as off-white solid.

Step 3: Synthesis of 3-iodo-7-methoxynaphthalen-2-amine: A mixture of tert-butyl (6-iodo-7-methoxynaphthalen-2-yl)carbamate with other isomer (8.00 g from above) and TFA (30 mL) in DCM (90 mL) was stirred at 20° C. for 3 hours, then concentrated. Aqueous saturated $NaHCO_3$ (200 mL) was added, then extracted with ethyl acetate (200 mL×3). The combined organic layers were dried over anhydrous $Na_2SO_4$ and concentrated. Purification by silica gel column (PE/EtOAc=5/1) gave the product (3.50 g, 2-step yield 16%) as off-white solid.

Step 4: Synthesis of Intermediate 6: To a solution of the above product (1.50 g, 5.01 mmol) in water (20 mL) and conc. HCl (20 mL) was added a solution of $NaNO_2$ (345 mg, 5.01 mmol) in water (10 mL) dropwise at 0° C. The reaction was stirred at 0° C. for 1 hour. Then $HBF_4$ (10 mL) was added and the mixture was stirred for 10 minutes. The mixture was filtered and the solid was washed with water (50 mL), dried under reduced pressure. The solid was dissolved in xylene (20 mL) and refluxed for 1 hour. The mixture was cooled to room temperature, diluted with water (50 mL), extracted with ethyl acetate (50 mL×3). The combined organic layers were dried over anhydrous $Na_2SO_4$ and concentrated in vacuo. The residue was purified by silica gel column (PE/EtOAc=100/1) to give the product (1.20 g, 79%). $^1$H NMR ($CDCl_3$ 400 MHz TMS): δ 8.19 (d, J=6.0 Hz, 1H), 7.63 (d, J=9.2 Hz, 1H), 7.38 (d, J=9.2 Hz, 1H), 7.10 (dd, J=9.2, 2.4 Hz, 1H), 7.03 (d, J=2.4 Hz, 1H), 3.92 (s, 3H).

Intermediate 7,
3-chloro-2-iodo-6-methoxynaphthalene

To a solution of 3-iodo-7-methoxynaphthalen-2-amine (see Intermediate 6, product of step 3) (1.0 g, 3.34 mmol) in water (20 mL) and conc. HCl (20 mL) was added a solution of $NaNO_2$ (230 mg, 3.34 mmol) in water (10 mL) dropwise at 0° C. and the reaction was stirred at 0° C. for 1 hour. Then CuCl (400 mg, 4.04 mmol) was added and the mixture was stirred at 20° C. for 2 hours. An aqueous/EtOAc workup was followed by purification by silica gel column (PE/EtOAc=100/1) to give 3-chloro-2-iodo-6-methoxynaphthalene (900 mg, yield 85%) as off-white solid. $^1$H NMR ($CDCl_3$ 300 MHz TMS): δ 8.29 (s, 1H), 7.84 (s, 1H), 7.60 (d, J=9.0 Hz, 1H), 7.13 (dd, J=9.0, 2.7 Hz, 1H), 6.99 (d, J=2.4 Hz, 1H), 3.91 (s, 3H).

Intermediate 8, MPHT

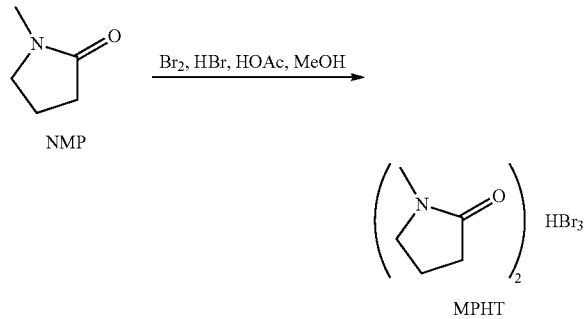

To MeOH (200 mL) was added HBr (97.2 g, 1.20 mol) in HOAc (120 mL) dropwise followed by the addition of $Br_2$ (190 g, 1.20 mol). The mixture was stirred at 10° C. for 10 minutes. Then NMP (257 g, 2.60 mol) was added dropwise. The reaction mixture was stirred at 10° C. for 1 hour. Then the mixture was filtered. The solid was washed with MTBE (200 mL) and dried under vacuum to give MPHT (361 g, yield 41%) as an orange solid. $^1$H NMR ($CDCl_3$ 400 MHz): δ 3.72 (t, J=7.2 Hz, 4H), 3.07 (s, 6H), 2.92 (t, J=8.0 Hz, 4H), 2.32-2.18 (m, 4H).

Intermediate 9,
6-(benzyloxy)-2-bromo-1-methoxynaphthalene

Step 1: Synthesis of 6-(benzyloxy)-3,4-dihydronaphthalen-1(2H)-one: A mixture of 6-hydroxy-1-tetralone (50.0 g, 308 mmol), $K_2CO_3$ (64.0 g, 434 mmol) and BnBr (58.0 g, 340 mmol) in DMF (400 mL) was stirred at 25° C. for 16 hours. The mixture was diluted in water (1000 mL), extracted with EtOAc (1000 mL×3). The combined organic layers were washed with brine (500 mL×3), dried over anhydrous $Na_2SO_4$ and concentrated under reduced pressure to give the product as a brown solid (54.0 g, yield 69%).

Step 2: Synthesis of 6-(benzyloxy)-2,2-dibromo-3,4-dihydronaphthalen-1(2H)-one: To a mixture of the above product (10.1 g, 40.0 mmol) in MeCN (20 mL) was added a solution of MPHT (Intermediate 8) (35.1 g, 80.0 mmol) in MeCN (130 mL) dropwise at 80° C. Then the reaction mixture was stirred at 80° C. for 1.5 hours. The mixture was quenched with aqueous saturated $Na_2S_2O_3$ (200 mL) and extracted with EtOAc (300 mL×3). The combined organic layers were washed with 5% aqueous HCl (100 mL×3), dried over anhydrous $Na_2SO_4$ and concentrated in vacuo. The residue was purified by silica gel column (PE/EtOAc=50/1) to give the product (7.18 g, yield 44%) as a white solid.

Step 3: Synthesis of 6-(benzyloxy)-2-bromonaphthalen-1-ol: A mixture of the above product (7.18 g, 17.5 mmol) and TEA (50 mL) in anhydrous $CHCl_3$ (30 mL) was stirred at 25° C. for 4 hours. The mixture was quenched with aqueous saturated $Na_2S_2O_3$ (200 mL) and extracted with DCM (300 mL×3). The combined organic layers were washed with 5% aqueous HCl (100 mL×3), dried over anhydrous $Na_2SO_4$ and concentrated in vacuo. The residue was purified by silica gel column (PE) to give the product (450 mg, yield 8%) as a white solid.

Step 4: Synthesis of Intermediate 9: A mixture of the above product (500 mg, 1.51 mmol), $K_2CO_3$ (415 mg, 3.00 mmol) and $CH_3I$ (0.75 mL, 14.8 mmol, 2.80 g/mL) in DMF (10 mL) under $N_2$ atmosphere was stirred at 25° C. for 18 hours. The mixture was diluted in water (50 mL) and extracted with EtOAc (50 mL×3), dried over anhydrous $Na_2SO_4$ and concentrated. The residue was purified by prep-TLC (PE/EtOAc=100/1) to give 6-(benzyloxy)-2-bromo-1-methoxynaphthalene (321 mg, yield 59%) as an off-white solid. $^1$H NMR ($CDCl_3$ 300 MHz TMS): δ 8.04 (d, J=9.0 Hz, 1H), 7.56-7.46 (m, 3H), 7.46-7.34 (m, 4H), 7.30-7.24 (m, 1H), 7.19 (d, J=2.4 Hz, 1H), 5.17 (s, 2H), 3.99 (s, 3H).

Intermediate 10, 1-fluoro-6-methoxynaphthalen-2-yl trifluoromethanesulfonate

Step 1: Synthesis of 1-bromo-6-methoxy-2-(methoxymethoxy)naphthalene: To a solution of 1-bromo-6-methoxynaphthalen-2-ol (described in U.S. 61/423,799) (2.90 g, 11.5 mmol) in MeOH (20 mL) and THF (20 mL) was added $K_2CO_3$ (3.18 g, 23.0 mmol) and MOMCl (1.10 g, 13.8 mmol). The resulting mixture was stirred at 20° C. for 48 hours and stirred at 30-40° C. for 5 days. An aqueous/EtOAc workup was followed by purification by silica gel column chromatography (PE to PE/EtOAc=200/1) to give the product (1.90 g, yield 56%) as an off-white solid.

Step 2: Synthesis of 1-fluoro-6-methoxy-2-(methoxymethoxy)naphthalene: To a solution of the above product (1.00 g, 3.38 mmol) in anhydrous THF (20 mL) was added n-BuLi (1.62 mL, 4.06 mmol, 2.50 M in hexane) dropwise at 0° C. The mixture was stirred at 0° C. for 30 min then cooled to −78° C. A solution of N-fluorobenzenesulfonimide (1.28 g, 4.06 mmol) in anhydrous THF (5 mL) was added to the reaction mixture. The resulting mixture was stirred at −78° C. for 1 hour, then stirred at 25° C. for 12 hours. The reaction mixture was quenched with aq. $NH_4Cl$ (60 mL), and extracted with EtOAc (20 mL×2). The combined organic layers were washed with $H_2O$ (20 mL) and brine (20 mL), dried over anhydrous $Na_2SO_4$, filtered and concentrated under reduced pressure. The crude product was purified by silica gel column (PE to PE/EtOAc=200/1) to give the product (280 mg, yield 35%) as an off-white solid.

Step 3: Synthesis of 1-fluoro-6-methoxynaphthalen-2-ol: A mixture of the above product (770 mg, 3.26 mmol) in HCl/dioxane (15 mL) was stirred at 25° C. for 2 hours. The reaction mixture was neutralized with aqueous NaOH (2M) to pH=7, followed by an aqueous/EtOAc workup. The crude product was purified by silica gel column (PE/EtOAc=200/1 to 100/1) to give the product (380 mg, yield 61%) as an off-white solid.

Step 4: Synthesis of Intermediate 10: To a solution of the above product (50.0 mg, 0.260 mmol) and TEA (34.2 mg, 0.338 mmol) in anhydrous DCM (10 mL) was added $Tf_2O$ (80.7 mg, 0.286 mmol) at −50° C. The reaction mixture was stirred at −50° C. for 0.5 hour. The resulting mixture was quenched with brine (30 mL) and extracted with DCM (20 mL×3). The combined organic layers were washed with $H_2O$ (20 mL) and brine (20 mL), dried over anhydrous $Na_2SO_4$, filtered and concentrated under reduced pressure to give Intermediate 10 (80 mg, yield 95%) as an off-white solid. $^1H$ NMR ($CDCl_3$ 400 MHz): δ 8.04 (d, J=9.2 Hz, 1H), 7.55 (d, J=8.8 Hz, 1H), 7.38-7.21 (m, 2H), 7.15 (s, 1H), 3.94 (s, 3H).

Intermediate 11, 6-(benzyloxy)-2-bromo-3-(methoxymethoxy)naphthalene

Step 1: Synthesis of 3-bromonaphthalene-2,7-diol: To a solution of 2,7-dihydroxynaphthalene (8.00 g, 50.0 mmol) in AcOH (30 mL) was added $Br_2$ (16.0 g, 100 mmol) in AcOH (30 mL) dropwise over 20 min. at 10-15° C. The mixture was stirred at this temperature for 1 hour. Sn powder (12.4 g, 130 mmol) and $H_2O$ (25 mL) were added and the mixture was stirred at 80° C. for 1 hour. After an aqueous/EtOAc workup, the crude was purified by column chromatography on silica gel (PE/EtOAc=5/1) and then prep-HPLC (0.1% TFA as additive) to give 3-bromonaphthalene-2,7-diol (8.2 g, yield 68%) as off-white solid.

Step 2: Synthesis of 6-bromo-7-(methoxymethoxy)naphthalen-2-ol: To a solution of the above product (4.00 g, 16.7 mmol) in MeCN (40 mL) was added $K_2CO_3$ (2.02 g, 14.5 mmol). The mixture was degassed for three times and MOMCl (1.87 g, 23.4 mmol) was added at −18° C. over 2 hours via syringe pump. The mixture was stirred at −18° C. for 2 hours and then quenched with water (50 mL). The mixture was acidified with aqueous HCl (2M) until pH=6 and extracted with EtOAc (50 mL×3), washed with brine (100 mL), dried over $Na_2SO_4$ and concentrated to give the crude product, which was purified by column chromatography on silica gel (PE/EtOAc=10/1) to give the product (1.5 g, yield 32%) as off-white solid.

Step 3: Synthesis of Intermediate 11: To a solution of the above product (1.50 g, 5.30 mmol) in DMF (15 mL) was added $K_2CO_3$ (1.47 g, 10.6 mmol) and BnBr (1.18 g, 6.89 mmol). The mixture was stirred at 80° C. overnight. Water (5 mL) was added and the mixture was acidified with aqueous HCl (0.1M) until pH=7 carefully and extracted with EtOAc (30 mL×3). The combined organic layers were washed with brine (50 mL), dried over $Na_2SO_4$ and concentrated in vacuo to give (1.98 g, yield 100%) as yellow solid.

Intermediate 12, 1-cyano-6-methoxynaphthalen-2-yl trifluoromethanesulfonate

Step 1: Synthesis of 1-bromo-6-methoxynaphthalen-2-ol: To a mixture of 6-methoxynaphthalen-2-ol (20 g, 114.8 mmol) in DMF (250 mL) was added a solution of NBS (21.5 g, 120 mmol) in DMF (50 mL) over a 30 min period. The reaction mixture was stirred for 45 min and poured into water. The precipitate was collected by filtration and dried to give the desired product (25.5 g, 87%) as white solid.

Step 2: Synthesis of 2-hydroxy-6-methoxy-1-naphthonitrile: A mixture of the above product (400 mg, 1.58 mol), $Zn(CN)_2$ (742 mg, 6.32 mmol), $Pd(PPh_3)_4$ (913 mg, 0.79 mmol) in DMF (20 mL) was heated in a microwave reactor at 140° C. for 10 min. The reaction mixture was cooled and treated with water (30 mL), extracted with EtOAc. The combined organic layers were dried over $MgSO_4$, filtered and concentrated. The residue was purified by silica gel chromatography (EA/PE=1/3) to give the product (240 mg, 76%) as white solid.

Step 3: Synthesis of Intermediate 12: To a solution of the above product (2.7 g, 13.5 mmol) and DIPEA (2.8 g, 27.1 mmol) in DCM (15 mL) at −78° C. was added trifluoromethanesulfonic anhydride (7.6 g, 27.1 mmol) dropwise. The mixture was allowed to slowly warm to 0° C. The resulting mixture was concentrated and purified by silica gel chromatography (EtOAc/PE=1/5) to give Intermediate 12 (4.0 g, 90%) as white solid. MS (ESI): m/z 332 $[M+1]^+$.

Intermediate 13: 6-bromo-1-fluoronaphthalen-2-ol

To a solution of 6-bromonaphthalen-2-ol (2.23 g, 10.0 mmol) in $CH_3CN$ (50 mL) was added Selectfluor (4.20 g, 12.0 mmol). The reaction mixture was heated at 60° C. overnight and concentrated. The residue was partitioned between water (50 mL) and EtOAc (100 mL). The aqueous phase was separated and extracted with ethyl acetate. The combined organic layers were washed with brine, dried over $Na_2SO_4$, filtered and concentrated. The residue was purified by silica gel chromatography to give 6-bromo-1-fluoronaphthalen-2-ol using ethyl acetate and hexanes as solvents (2.0 g, 83% yield).

Example 35

GSNOR Assays

Various compounds were tested in vitro for their ability to inhibit GSNOR activity. GSNOR inhibitor compounds in Examples 1-33 had an $IC_{50}$ of about <5 μM. GSNOR inhibitor compounds in Examples 1-3, 5, 6, 12, 15, 17, 18, 20-33 had an $IC_{50}$ of about <0.1 μM. GSNOR inhibitor compounds in Examples 1, 2, 6, 12, 15, 17, 21-23, 25, 27-32 had an $IC_{50}$ of about <0.05 μM.

GSNOR expression and purification is described in Biochemistry 2000, 39, 10720-10729.

GSNOR Fermentation: Pre-cultures were grown from stabs of a GSNOR glycerol stock in 2XYT media containing 100 ug/ml ampicillin after an overnight incubation at 37° C. Cells were then added to fresh 2XYT (4 L) containing ampicillin and grown to an OD ($A_{600}$) of 0.6-0.9 at 37° C. before induction. GSNOR expression was induced with 0.1% arabinose in an overnight incubation at 20° C.

GSNOR Purification: *E. coli* cell paste was lysed by nitrogen cavitation and the clarified lysate purified by Ni affinity chromatography on an AKTA FPLC (Amersham Pharmacia). The column was eluted in 20 mM Tris pH 8.0/250 mM NaCl with a 0-500 mM imidazole gradient. Eluted GSNOR fractions containing the Smt-GSNOR fusion were digested overnight with Ulp-1 at 4° C. to remove the affinity tag then re-run on the Ni column under the same conditions. GSNOR was recovered in the flowthrough fraction and for crystallography is further purified by Q-Sepharose and Heparin flowthrough chromatography in 20 mM Tris pH 8.0, 1 mM DTT, 10 uM $ZnSO_4$.

GSNOR Assay: GSNO and enzyme/NADH Solutions are made up fresh each day. The solutions are filtered and allowed to warm to room temperature. GSNO solution: 100 mM $NaPO_4$ (pH 7.4), 0.480 mM GSNO. 396 μL of GSNO Solution is added to a cuvette followed by 8 μL of test compound in DMSO (or DMSO only for full reaction control) and mixed with the pipette tip. Compounds to be tested are made up at a stock concentration of 10 mM in 100% DMSO. 2 fold serial dilutions are done in 100% DMSO. 8 μL of each dilution are added to an assay so that the final concentration of DMSO in the assay is 1%. The concentrations of compounds tested range from 100 to 0.003 μM. Enzyme/NADH solution: 100 mM $NaPO_4$ (pH 7.4), 0.600 mM NADH, 1.0 μg/mL GSNO Reductase. 396 μL of the Enzyme/NADH solution is added to the cuvette to start the reaction. The cuvette is placed in the Cary 3E UV/Visible Spectrophotometer and the change in 340 nm absorbance/min at 25° C. is recorded for 3 minutes. The assays are done in triplicate for each compound concentration. $IC_{50}$'s for each compound are calculated using the standard curve analysis in the Enzyme Kinetics Module of SigmaPlot.

Final assay conditions: 100 mM $NaPO_4$, pH 7.4, 0.240 mM GSNO, 0.300 mM NADH, 0.5 μg/mL GSNO Reductase, and 1% DMSO. Final volume: 800 μL/cuvette.

Example 36

Efficacy of GSNORi in Experimental Asthma

Experimental Asthma Model:
A mouse model of ovalbumin (OVA)-induced asthma was used to screen GSNOR inhibitors for efficacy against methacholine (MCh)-induced bronchoconstriction/airway hyper-responsiveness. This is a widely used and well characterized model that presents with an acute, allergic asthma phenotype with similarities to human asthma. Efficacy of GSNOR inhibitors was assessed using a protocol in which GSNOR inhibitors were administered after OVA sensitization and airway challenge, and prior to challenge with MCh. Bronchoconstriction in response to challenge with increasing doses of MCh was assessed using whole body plethysmography ($P_{enh}$; Buxco). The amount of eosinophil infiltrate into the bronchoaveolar lavage fluid (BALF) was also determined as a measure of lung inflammation. The effects of GSNOR inhibitors were compared to vehicles and to Combivent (inhaled; 1H) as the positive control.

Materials and Method
Allergen Sensitization and Challenge Protocol
OVA (500 μg/ml) in PBS was mixed with equal volumes of 10% (w/v) aluminum potassium sulfate in distilled water and incubated for 60 min. at room temperature after adjustment to pH 6.5 using 10 N NaOH. After centrifugation at 750×g for 5 min, the OVA/alum pellet was resuspended to the original volume in distilled water. Mice received an intraperitoneal (IP) injection of 100 μg OVA (0.2 mL of 500 μg/mL in normal saline) complexed with alum on day 0. Mice were anesthetized by IP injection of a 0.2-mL mixture of ketamine and xylazine (0.44 and 6.3 mg/mL, respectively) in normal saline and were placed on a board in the supine position. Two hundred fifty micrograms (100 μl of a 2.5 mg/ml) of OVA (on day 8) and 125 μg (50 μl of 2.5 mg/ml) OVA (on days 15, 18, and 21) were placed on the back of the tongue of each animal.

Pulmonary Function Testing (Penh)
In vivo airway responsiveness to methacholine was measured 24 h after the last OVA challenge in conscious, freely moving, spontaneously breathing mice with whole body plethysmography using a Buxco chamber (Wilmington, N.C.). Mice were challenged with aerosolized saline or increasing doses of methacholine (5, 20, and 50 mg/mL) generated by an ultrasonic nebulizer for 2 min. The degree of bronchoconstriction was expressed as enhanced pause ($P_{enh}$), a calculated dimensionless value, which correlates with the measurement of airway resistance, impedance, and intrapleural pressure in the same mouse. $P_{enh}$ readings were taken and averaged for 4 min. after each nebulization challenge. $P_{enh}$ is calculated as follows: $P_{enh}=[T_e/T_r-1]\times(PEF/PIF)]$, where $T_e$ is expiration time, $T_r$ is relaxation time, PEF is peak expiratory flow, and PIF is peak inspiratory flow×0.6 coefficient. The time for the box pressure to change from a maximum to a user-defined percentage of the maximum represents the relaxation time. The $T_r$ measurement begins at the maximum box pressure and ends at 40%.

Eosinophil Infiltrate in BALF
After measurement of airway hyper-reactivity, the mice were exsanguinated by cardiac puncture, and then BALF was collected from either both lungs or from the right lung after tying off the left lung at the mainstem bronchus. Total BALF cells were counted from a 0.05 mL aliquot, and the remaining fluid was centrifuged at 200×g for 10 min at 4° C. Cell pellets were resuspended in saline containing 10% BSA with smears made on glass slides. Eosinophils were stained for 5 min. with 0.05% aqueous eosin and 5% acetone in distilled water, rinsed with distilled water, and counterstained with 0.07% methylene blue. Alternatively, eosinophils and other leukocytes were stained with DiffQuik.

GSNOR Inhibitors and Controls
GSNOR inhibitors were reconstituted in phosphate buffered saline (PBS), pH 7.4, or 0.5% w/v carboxy methylcellulose at concentrations ranging from 0.00005 to 3 mg/mL. GSNOR inhibitors were administered to mice (10 mL/kg) as a single dose or multiple dose either intravenously (IV) or orally via gavage. Dosing was performed from 30 min. to 72 h prior to MCh challenge. Effects of GSNOR inhibitors were compared to vehicle dosed in the same manner.

Combivent was used as the positive control in all studies. Combivent (Boehringer Ingelheim) was administered to the lung using the inhaler device supplied with the product, but adapted for administration to mice, using a pipet tip. Combivent was administered 48 h, 24 h, and 1 h prior to MCh challenge. Each puff (or dose) of Combivent provides a dose of 18 μg ipatropium bromide (IpBr) and 103 μg albuterol sulfate or approximately 0.9 mg/kg IpBr and 5 mg/kg albuterol.

Statistical Analyses

Area under the curve values for $P_{enh}$ across baseline, saline, and increasing doses of MCh challenge were calculated using GraphPad Prism 5.0 (San Diego, Calif.) and expressed as a percent of the respective (IV or orally administered) vehicle control. Statistical differences among treatment groups and the respective vehicle control group within each study were calculated using one-way ANOVA, Dunnetts or Bonferroni post-hoc tests or t-test (JMP 8.0, SAS Institute, Cary, N.C. or Microsoft Excel). A p value of <0.05 among the treatment groups and the respective vehicle control group was considered significantly different.

Results

In the OVA model of asthma, the compound of Example 1 significantly (p<0.05) decreased eosinophil infiltration in BAL by 44% of vehicle control when given via three oral doses of 10 mg/kg at 48 h, 24 h, and 1 h prior to assessment.

Example 37

Mouse Pharmacokinetic (PK) Study

Experimental Model

The mouse was used to determine the pharmacokinetics of compounds of the invention. This species is widely used to assess the bioavailability of compounds by administering both oral (PO) and intravenous (IV) test articles. Efficacy of the compounds of the invention was compared by assessing plasma exposure in male BALB/c mice either via IV or PO administration at the times of peak activity.

Materials and Methods

IV Administration of Compounds of the Invention

Compounds of the invention were reconstituted in a phosphate buffered saline (PBS)/10% Solutol (HS 15) clear solution resulting in a concentration of 0.2 mg/mL and administered to mice (2 mg/kg) as a single IV dose. Animals were dosed via the lateral tail vein. Blood samples were collected at designated time points (0.083, 0.25, 0.5, 1, 2, 4, 8, 16, 24 hours) by cardiac puncture under isoflurane anesthesia (up to 1 mL blood per animal). The blood was collected into tubes containing Li-Heparin. The blood samples were kept on ice until centrifugation within approximately 30 minutes of collection. The plasma was transferred into labeled polypropylene tubes and frozen at −70° C. until analyzed by LC/MS/MS.

PO Administration of Compounds of the Invention

The compounds of the invention were reconstituted in 40% Propylene Glycol/40% Propylene Carbonate/20% of a 5% Sucrose clear solution resulting in a concentration of 2 mg/mL and administered to mice (10 mg/kg) as a single oral dose via gavage. Blood samples were collected at 0.25, 0.5, 1, 2, 4, 8, 12, 16, 20 and 24 hours post dose by cardiac puncture under isoflurane anesthesia. The blood was collected in tubes containing Li-Heparin. The blood samples were kept on ice until centrifugation within approximately 30 minutes of collection. The plasma was transferred into labeled polypropylene tubes and frozen at −70° C. until analyzed by LC/MS/MS.

LC/MS/MS Analysis

Plasma samples at each timepoint were analyzed using a LC-MS/MS with a lower limit of quantification (LLOQ) of 1 ng/mL. Plasma was analyzed to determine the amount of the compound of the invention in each sample and regression curves generated for each compounds of the invention in the relevant matrixes.

WinNonlin analysis was used for calculating PK parameters for both the IV and PO administrations:

PK parameters for IV portion–$AUC_{last}$;$AUC_{INF}$;T1/2; Cl;Vss;$C_{max}$;MRT PK parameters for PO portion–$AUC_{last}$;$AUC_{INF}$;T1/2; $C_{max}$;Cl,MRT.

In addition to the above PK parameters, bioavailability (% F) was calculated.

Results

The compound of Example 1 and the compound of Example 2 were tested and both had an oral bioavailability of greater than 40%.

Example 38

Efficacy of GSNOR Inhibitors in Experimental Inflammatory Bowel Disease (IBD)

Overview of the Models:

Acute and chronic models of dextran sodium sulfate (DSS)-induced IBD in mice were used to explore efficacy of GSNORi against this disease. Acute and chronic DSS-induced IBD are widely used and well characterized models that induce pathological changes in the colon similar to those observed in the human disease. In these models and in human disease, epithelial cells within the crypts of the colon are disrupted, leading to dysfunction of the epithelial barrier and the ensuing tissue inflammation, edema, and ulceration. GSNORi therapy may benefit IBD by restoring s-nitrosoglutathione (GSNO) levels, and thus prevent or reverse the epithelial barrier dysfunction.

Acute Prophylactic Model:

Experimental IBD was induced by administration of DSS in the drinking water of male C57B1/6 mice (N=8 to 10 mice per group) for 6 consecutive days. GSNORi was dosed orally at doses of 0.1 to 10 mg/kg/day for 10 days starting two days prior to and continuing two days post DSS exposure. Two days post DSS exposure, the effect of GSNORi was assessed in a blinded fashion via endoscopy and histopathology using a five point scale ranging from a score=0 (normal tissue) through a score=4 (ulcerative tissue damage and marked pathological changes). Levels of circulating cytokines involved in inflammatory pathways were also assessed. The effect of GSNORi was compared to vehicle treated controls. The corticosteroid, prednisolone, was used as the positive control in this study and was administered daily at 3 mg/kg/day via oral dosing. Naïve mice (N=5) were also assessed as a normal tissue control.

Chronic Treatment Model:

Experimental IBD was induced by administration of DSS in the drinking water of male C57B1/6 mice (N=10 to 12 mice per group) for 6 consecutive days. GSNORi was dosed orally at doses of 10 mg/kg/day for 14 days starting one day after cessation of DSS exposure. Efficacy of GSNORi was assessed in a blinded fashion via endoscopy after 7 days and 14 days of GSNORi dosing and via histopathology after 14 days of GSNORi dosing using a five point scale ranging from a score=0 (normal tissue) through a score=4 (ulcerative tissue damage and marked pathological changes). Levels of circulating cytokines involved in inflammatory pathways were also assessed. The effect of GSNORi was compared to vehicle treated controls. The corticosteroid, prednisolone, was used as the positive control in this study and was administered daily at 3 mg/kg/day via oral dosing. Naïve mice (N=5) were also assessed as a normal tissue control.

Results:

The compound of Example 1 attenuated colon injury in mouse models of acute and chronic DSS-induced IBD. In the acute model, the percent of mice presenting with severe colon injury scores via endoscopy or histopathology assessment was decreased by 17% or 21%, respectively, of vehicle control after oral treatment with the compound of Example 1 at 1 mg/kg/day for 10 consecutive days using a prophylactic dosing regimen. The compound of Example 1 dosed orally at 10 mg/kg/day for 10 days, significantly ($p<0.05$) decreased the percent of mice presenting with severe endoscopy scores by 72% of vehicle control. In the chronic model, the percent of mice presenting with severe colon injury scores via endoscopy or histopathology assessment was decreased by 50% or 17%, respectively, of vehicle control after oral treatment with the compound of Example 1 at 10 mg/kg/day for up to 14 consecutive days using a treatment dosing regimen.

The compound of Example 2 attenuated colon injury in a mouse model of acute DSS-induced IBD. The percent of mice presenting with severe colon injury scores via endoscopy or histopathology assessments was decreased by 58% ($p<0.05$) or 26%, respectively, of vehicle control after oral treatment with the compound of Example 2 at 10 mg/kg/day for 10 consecutive days using a prophylactic dosing regimen.

Example 39

Efficacy of GSNOR Inhibitors in Experimental Chronic Obstructive Pulmonary Disease (COPD)

Short Duration Cigarette Smoke COPD Models

The efficacy of GSNOR inhibitors was assessed in a mouse model of chronic obstructive pulmonary disease (COPD) induced by short duration (4 days or 11 days) of exposure to cigarette smoke. Infiltration of inflammatory cells into the bronchoalveolar lavage fluid (BALF) and BALF levels of chemokines involved in inflammation and tissue turnover/repair were measured to assess the influences of GSNOR inhibitors on some of the early events associated with the initiation and progression of COPD.

Overview of the Models:

Efficacy of GSNOR inhibitors against COPD was explored using acute (4 day) and subchronic (11 day) models of cigarette smoke-induced COPD in mice. Exposure of animals to cigarette smoke provides a model of COPD in which injury is induced by the same causative agent as in human disease and in which injury exhibits similarities to the human disease, including airway obstruction, airspace enlargement, and involvement of inflammatory responses in these pathologies. In animal models, changes in lung pathology are only evident after extended (several months) duration of exposure to cigarette smoke, thus making chronic models prohibitive as effective screening tools. More recently, models exploring inflammatory responses after short duration (2 weeks or less) of smoke exposure in mice have been utilized as tools for screening efficacy and mechanisms of action of novel therapeutics against COPD. The key roles of inflammation in the initiation and progression of COPD, make these short duration models relevant for initial tests of efficacy of novel therapeutics.

Acute (4 Day) Smoke Exposure Model: Female C57B1/6 mice (N=8 per group) were exposed to cigarette smoke using a whole body exposure chamber. Mice were exposed daily for 4 consecutive days to 4 cycles of smoke from 6 sequential cigarettes (Kentucky 3R4F without filter) with a 30 minute smoke free interval between cycles. GSNOR inhibitors were administered daily via oral dosing at 10 mg/kg/day for 7 days starting 2 days prior to smoke exposure and continuing 1 day post-exposure. The effects of GSNOR inhibitors were assessed by quantitating the numbers of total cells, leukocytes, and leukocytes differentials in the BALF via light microscopy and the levels of BALF chemokines via ELISA at approximately 24 h after the last smoke exposure. The effect of GSNOR inhibitors were compared to vehicle treated controls. The PDE4 inhibitor, roflumilast, was used as the positive control for the study. A group of naïve mice (N=8) was exposed to air and used as a negative control for the study.

Subchronic (11 Day) Smoke Exposure Model: Female C57B1/6 mice (N=10 per group) were exposed to cigarette smoke generated from Marlboro 100 cigarettes without filters. Exposure times were 25 min. on study day 1, 35 min. on study day 2, and 45 min. on study days 3 to 11. GSNOR inhibitors were administered one hour prior to smoke exposure on each day. GSNOR inhibitors were dosed orally at 1 to 10 mg/kg/day for 11 days. The effects of GSNOR inhibitors were assessed by quantitating the number of total cells, and leukocytes differentials in the BALF via light microscopy at 24 h after the last exposure. The effect of GSNOR inhibitors were compared to vehicle treated controls and expressed as percent inhibition of the cigarette smoke induced increases in BALF cell numbers. Roflumilast was used as the positive control for the study and was dosed at 5 mg/kg/day. A group of naïve mice (N=10) was exposed to air and dosed with vehicle as a negative control for the study.

Results:

The compound of Example 1 inhibited the smoke-induced increase in total cells ($p<0.05$), macrophages ($p<0.05$), neutrophils ($p<0.05$), and lymphocytes in BAL by 40%, 40%, 49%, and 41%, respectively, when dosed orally at 10 mg/kg/day for 11 days in the subchronic 11 day model. These effects of the compound of Example 1 were comparable to those of roflumilast.

Example 40

An Exploratory Mouse Study of Acetaminophen Toxicity

S-nitrosoglutathione reductase (GSNOR) inhibition has been previously shown in our hands to ameliorate the negative manifestations of gastrointestinal injury in animal models. As an extension of these observations, the effects of S-nitrosoglutathione (GSNO) or GSNOR inhibitors (GSNORi) on acetaminophen (ACAP) induced liver toxicity can be evaluated in a mouse model of liver injury. Blood samples are collected for liver function assays and tissue samples are collected at the end of the study for histopathologic examination.

Materials and Methods

GSNORi, GSNO, acetaminophen (ACAP, Sigma) Vehicles (½ cc syringes for dosing), Isoflurane, 18 1 cc syringes w/26 g needles for blood collection, 90 serum separator tubes for clinical chemistry.

General Study Design: Animals (5/group) are acclimated for at least 3 days prior to dosing. On Study Day 1, acetaminophen treatment (300 mg/kg PO) was given a single time=0 to fasted animals. Two hours later, GSNORi (10 mg/kg/dose) or GSNO (5 mg/kg/dose) are intravenously administered to the treatment groups. GSNORi or GSNO are given at 24 and 48 hours-post their initial administration to the treatment groups. Mice are observed for signs of clinical toxicity and blood was collected at 6, 24, and 72 hours post-ACAP administration for liver function tests: Alkaline phosphatase (ALK); Alanine aminotransferase (ALT); Aspartate aminotransferase (AST); Gamma glutamyltransferase (GGT) and Total bilirubin (TBILI). Livers are collected at 72 hours for histopathologic examination.

Study Outline

| Group | Treatment | Dose | Drug Concentration | N |
|---|---|---|---|---|
| 1 | ACAP PO | 300 mg/kg | 10 ml/kg | 5 |
| 2 | Saline PO | 0 mg/kg | 10 ml/kg | 5 |
| 3 | GSNORi IV | 10 mg/kg | 1 mg/mL | 5 |
| 4 | GSNO IV | 5 mg/kg | 1 mg/mL | 5 |
| 5 | GSNORi IV + ACAP | 10 m/k/300 m/k | 1 mg/mL | 5 |
| 6 | GSNO IV + ACAP | 5 m/k/300 m/k | 1 mg/mL | 5 |

Study Calendar:

| Day-6 | Receive mice and place in regular cages |
|---|---|
| Day-1 | Fast animals overnight |
| Day 0 | Weigh, PO ACAP time = 0, time = 2 IV GSNO or GSNORi bleed all groups at 6 hr post-ACAP |
| Day 1 | Weigh, bleed all groups for 24 hr LFTs, IV GSNO or GSNORi |
| Day 2 | Weigh, IV GSNO or GSNORi |
| Day 3 | Bleed for 72 hr LFTs, collect livers for weight and histology |

Vehicle, GSNO and GSNORi Preparation

The vehicle control article is Phosphate Buffered Saline (PBS) (not containing calcium, potassium, or magnesium) adjusted to pH 7.4. The vehicle components are weighed into a container on a tared balance and brought to volume with purified water (w/v). The 10× stock solution is mixed using a magnetic stirrer, as necessary. Thereafter, the 10× stock solution is diluted with deionized water at a ratio of 1:9 (v/v). GSNO is warmed to room temperature before preparation of solutions. Prior to use, the PBS solution is nitrogen sparged. 1 mg/mL GSNO solutions are kept cold (i.e., kept on an ice bath) and protected from light and used within 4 hours of preparation. GSNORi Preparation, the 1 mg/mL concentration is reconstituted in phosphate buffered saline (PBS), pH 7.4. GSNORi is administered to mice (10 mL/kg) as a single (IV) daily dose. Dosing is performed 2 hours post-ACAP administration and then 26 and 50 hours later. Effects of GSNO or GSNORi are compared to ACAP and saline vehicle dosed in the same manner.

Calculations: Mean body weights, mean liver organ weights and clinical pathology endpoints (+/−SD) with T-test and ANOVA (alpha=0.05) comparison to vehicle control group. The clinical pathology data are prepared as mean values unless the data are not normally distributed, in which case, median values can be presented with the minimum and maximum value range.

Example 41

An Exploratory Study to Assess the Anti NASH Fibrotic Activity of GSNORi in STAM Mice S-nitrosoglutathione reductase (GSNOR) inhibition has been previously shown in our hands to ameliorate the negative manifestations of gastrointestinal injury and ACAP injury in mouse models. As an extension of these observations, the effects of GSNOR inhibitors (GSNORi) ability to reverse fibrotic activity in nonalcoholic steatohepatitis (NASH)-induced liver disease is evaluated in STAM (signal transducing adaptor molecule) mice. In these mice sequential changes are seen from liver steatosis to fibrosis within two weeks and there are close similarities to human NASH histopathology.

Materials and Methods

GSNORi, Telmisartan, Vehicles (½ cc syringes for dosing), Isoflurane, 18 1 cc syringes w/26 g needles for blood collection, 90 serum separator tubes for clinical chemistry.

General Study Design: Animals (6/group) are acclimated prior to beginning the Study. At 4 weeks of age the animals are put on a diet, group 1 (normal mice) receives a normal diet while groups 2-4 (STAM mice) are put on a high fat diet for the duration of the Study. At Study Week 7 the mice begin oral daily dosing with GSNORi and are sacrificed at Study Week 9. Mice are observed for signs of clinical toxicity and blood/tissue is collected for liver analyses: Plasma triglycerides (TG); Alanine aminotransferase (ALT); Aspartate aminotransferase (AST); Gene Expression: Timp-1, α-SMA, collagen 3, TNF-α and MCP-1 as well as histopathologic examination using HE staining for (NAFLD) activity score and Sirius-red staining (fibrosis area).

Study Outline

| Group | Treatment | Diet | Dose | Drug Concentration | N |
|---|---|---|---|---|---|
| 1 | normal | ND | 0 mg/kg | 0 ml/kg | 6 |
| 2 | STAM + vehicle | HFD | 10 mg/kg | 1 mg/mL | 6 |
| 3 | STAM + GSNORi IV | HFD | 10 mg/kg | 1 mg/mL | 6 |
| 4 | STAM + Telmisarten | HFD | 10 mg/kg | 1 mg/mL | 6 |

ND: normal diet, HFD: high fat diet

Calculations: Mean body weights, mean liver organ weights and clinical pathology endpoints (+/−SD) with T-test and ANOVA (alpha=0.05) comparison to vehicle control group. The clinical pathology data are prepared as mean values unless the data are not normally distributed, in which case, median values were presented with the minimum and maximum value range.

\* \* \*

It will be apparent to those skilled in the art that various modifications and variations can be made in the methods and compositions of the present invention without departing from the spirit or scope of the invention.

What is claimed is:

1. The compound of Formula 1:

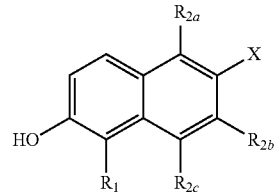

Formula 1 wherein $R_1$ is selected from the group consisting of H, F, and Cl;

$R_{2a}$ and $R_{2b}$ are independently selected from the group consisting of H, F, Cl, Br, Me, $OCH_3$, and cyano;

$R_{2c}$ is selected from the group consisting of H, F, Cl, Br, Me, and $OCH_3$;

X is selected from the group consisting of

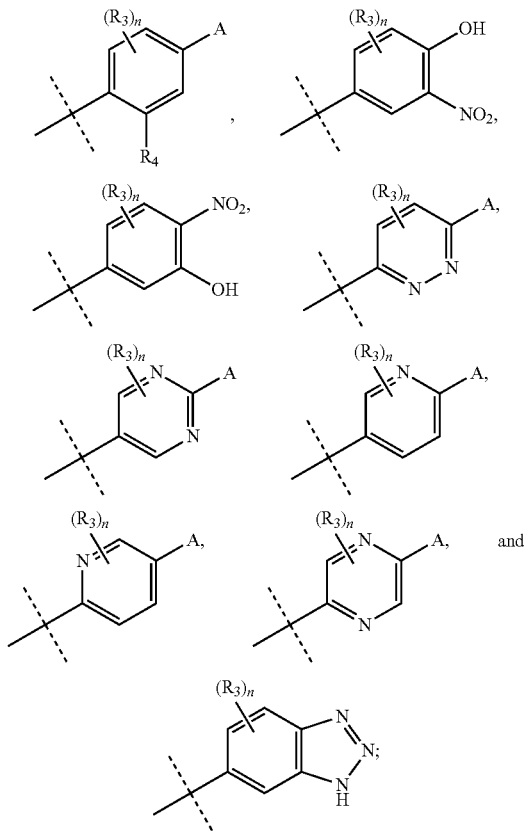

A is selected from the group consisting of

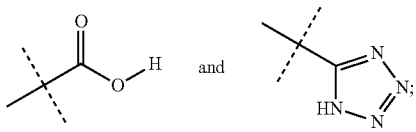

$R_3$ is selected from the group consisting of F, Cl, Br, $CH_3$, $CF_3$, $OCH_3$, cyano, $N(CH_3)_2$, and morpholino;

n is selected from the group consisting of 0, 1, and 2;

$R_4$ is selected from the group consisting of H, F, Cl, Br, $CH_3$, $CF_3$, $OCH_3$, cyano, $N(CH_3)_2$, and morpholino;

with the proviso that when X is

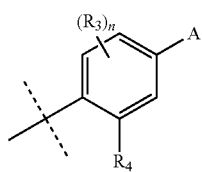

and A is COOH, then at least one of $R_1$, $R_{2a}$, $R_{2b}$, $R_{2c}$, and $R_4$ is not hydrogen, or n must be >0, and $R_3$ when meta to naphthalene, cannot be $CH_3$.

2. The compound of claim 1 wherein X is

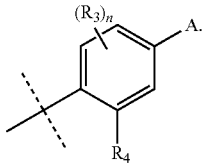

3. The compound of claim 2 wherein $R_{2c}$ is hydrogen.
4. The compound of claim 2 where $R_{2b}$ is hydrogen.
5. The compound of claim 1 wherein the compound is a compound of Formula 2

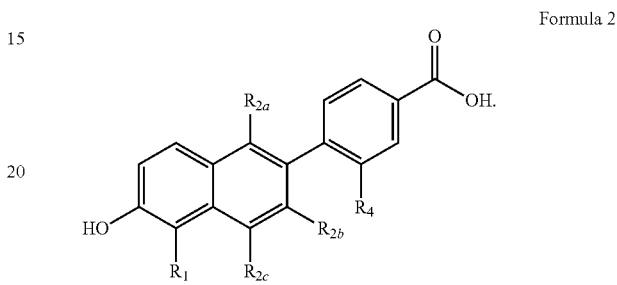

Formula 2

6. The compound of claim 5 wherein
   $R_1$ is selected from the group consisting of H and F;
   $R_{2a}$ is selected from the group consisting of H, F, Cl, Br, and cyano;
   $R_{2b}$ is selected from the group consisting of H, F, and Cl;
   $R_{2c}$ is H; and
   $R_4$ is selected from the group consisting of H, F, Cl, and cyano.

7. The compound of claim 5 wherein Ri is selected from the group consisting of F and Cl.

8. The compound of claim 5 wherein $R_{2a}$ is selected from the group consisting of F, Cl, Br, Me, $OCH_3$, and cyano.

9. The compound of claim 5 wherein $R_{2b}$ is selected from the group consisting of F, Cl, Br, Me, $OCH_3$, and cyano.

10. The compound of claim 5 wherein $R_{2c}$ is selected from the group consisting of F, Cl, Br, Me, and $OCH_3$.

11. The compound of claim 5 wherein $R_4$ is selected from the group consisting of F, Cl, Br, $CH_3$, $CF_3$, $OCH_3$, cyano, $N(CH_3)_2$, and morpholino.

12. The compound of claim 1 wherein the compound is a compound of Formula 3

Formula 3

13. The compound of claim 12 wherein X is

14. The compound of claim 13 where A is COOH.

15. The compound of claim 12 wherein the compound is a compound of Formula 4

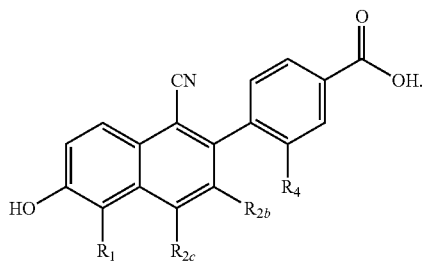

Formula 4

16. The compound of claim 15 wherein $R_{2c}$ is H.
17. The compound of claim 15 wherein $R_{2b}$ is H.
18. The compound of claim 15 wherein
$R_1$ is selected from the group consisting of H and F;
$R_{2b}$ is selected from the group consisting of H, F, and Cl;
$R_{2c}$ is H; and
$R_4$ is selected from the group consisting of H, F, Cl, and cyano.
19. The compound of claim 1 wherein the compound is a compound of Formula 5

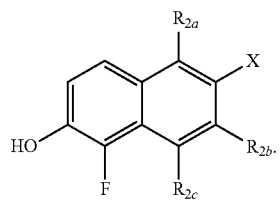

Formula 5

20. The compound of claim 19 wherein X is

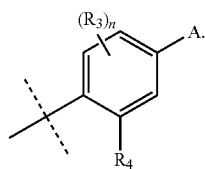

21. The compound of claim 20 wherein A is COOH.
22. The compound of claim 19 wherein the compound is a compound of Formula 6

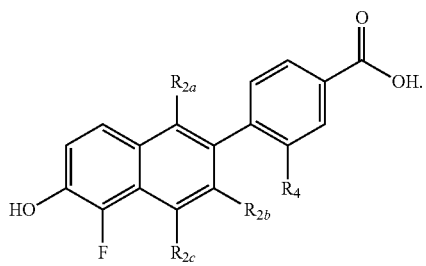

Formula 6

23. The compound of claim 22 wherein $R_{2c}$ is H.

24. The compound of claim 22 wherein $R_{2b}$ is H.
25. The compound of claim 22 wherein
$R_{2a}$ is selected from the group consisting of H, F, Cl, Br, and cyano;
$R_{2b}$ is selected from the group consisting of H, F, and Cl;
$R_{2c}$ is H; and
$R_4$ is selected from the group consisting of H, F, Cl, and cyano.
26. The compound of claim 1 wherein the compound is selected from the group consisting of
3-chloro-4-(6-hydroxynaphthalen-2-yl)benzoic acid;
3-fluoro-4-(6-hydroxynaphthalen-2-yl)benzoic acid;
4-(6-hydroxynaphthalen-2-yl)-3-methoxybenzoic acid;
3-(dimethylamino)-4-(6-hydroxynaphthalen-2-yl)benzoic acid;
3-cyano-4-(6-hydroxynaphthalen-2-yl)benzoic acid;
4-(6-hydroxynaphthalen-2-yl)-3-morpholinobenzoic acid;
4-(1-bromo-6-hydroxynaphthalen-2-yl)benzoic acid;
4-(6-hydroxy-1-methylnaphthalen-2-yl)benzoic acid;
4-(1-cyano-6-hydroxynaphthalen-2-yl)benzoic acid;
4-(6-hydroxy-3-methoxynaphthalen-2-yl)benzoic acid;
4-(1-chloro-6-hydroxynaphthalen-2-yl)benzoic acid;
6-(4-(1H-tetrazol-5-yl)phenyl)naphthalen-2-ol;
5-(6-hydroxynaphthalen-2-yl)picolinic acid;
6-(6-hydroxynaphthalen-2-yl)nicotinic acid;
5-(6-hydroxynaphthalen-2-yl)pyrazine-2-carboxylic acid;
6-(6-hydroxynaphthalen-2-yl)pyridazine-3-carboxylic acid;
5-(6-hydroxynaphthalen-2-yl)pyrimidine-2-carboxylic acid;
6-(1H-benzo[d][1,2,3]triazol-6-yl)naphthalen-2-ol;
4-(6-hydroxynaphthalen-2-yl)-3-(trifluoromethyl)benzoic acid;
3-chloro-4-(3-fluoro-6-hydroxynaphthalen-2-yl)benzoic acid;
4-(3-chloro-6-hydroxynaphthalen-2-yl)benzoic acid;
4-(3-fluoro-6-hydroxynaphthalen-2-yl)benzoic acid;
4-(6-hydroxy-1-methoxynaphthalen-2-yl)benzoic acid;
4-(1-fluoro-6-hydroxynaphthalen-2-yl)benzoic acid;
4-(6-hydroxy-3-methylnaphthalen-2-yl)benzoic acid;
4-(1-cyano-5-fluoro-6-hydroxynaphthalen-2-yl)benzoic acid;
4-(1-cyano-6-hydroxynaphthalen-2-yl)-3-fluorobenzoic acid;
3-chloro-4-(5-fluoro-6-hydroxynaphthalen-2-yl)benzoic acid;
4-(5-fluoro-6-hydroxynaphthalen-2-yl)benzoic acid;
3-fluoro-4-(5-fluoro-6-hydroxynaphthalen-2-yl)benzoic acid; and
4-(5-fluoro-6-hydroxynaphthalen-2-yl)-3-methylbenzoic acid.
27. A pharmaceutical composition comprising a therapeutically effective amount of a compound according to claim 1 together with a pharmaceutically accepted carrier or excipient.
28. A method of treatment of a disease or condition which comprises administering a therapeutically effective amount of a compound of Formula 1 as defined in claim 1 to a patient in need thereof, wherein the disease or condition is selected from asthma, COPD or inflammatory bowel disease (IBD).
29. A method of making a pharmaceutical composition comprising combining a compound of Formula 1 as defined in claim 1 with a pharmaceutically acceptable carrier or excipient.

* * * * *